(12) United States Patent
Chetham et al.

(10) Patent No.: US 9,504,406 B2
(45) Date of Patent: Nov. 29, 2016

(54) MEASUREMENT APPARATUS

(75) Inventors: Scott Chetham, Del Mar, CA (US); Christopher Newton Daly, Newport (AU); Ian John Bruinsma, Kings Langley (AU)

(73) Assignee: Impedimed Limited, Pinkenba, Queensland (AU)

( * ) Notice: Subject to any disclaimer, the term of this patent is extended or adjusted under 35 U.S.C. 154(b) by 1537 days.

(21) Appl. No.: 12/516,876

(22) PCT Filed: Nov. 29, 2007

(86) PCT No.: PCT/AU2007/001847
§ 371 (c)(1),
(2), (4) Date: Sep. 30, 2009

(87) PCT Pub. No.: WO2008/064426
PCT Pub. Date: Jun. 5, 2008

(65) Prior Publication Data
US 2010/0168530 A1 Jul. 1, 2010

(30) Foreign Application Priority Data

Nov. 30, 2006 (AU) ............................... 2006906726
Nov. 5, 2007 (AU) ............................... 2007906049

(51) Int. Cl.
*A61B 5/053* (2006.01)
*A61B 6/00* (2006.01)
*A61B 5/00* (2006.01)

(52) U.S. Cl.
CPC ........... *A61B 5/0537* (2013.01); *A61B 5/4872* (2013.01); *A61B 5/6843* (2013.01); *A61B 6/482* (2013.01); *A61B 6/505* (2013.01); *A61G 2210/20* (2013.01)

(58) Field of Classification Search
CPC .. A61B 5/4872; A61B 5/6843; A61B 6/505; A61G 2210/20
USPC ......................................... 600/300, 301, 442
See application file for complete search history.

(56) References Cited

U.S. PATENT DOCUMENTS

| 3,316,896 A | 5/1967 | Thomasset |
| 3,834,374 A | 9/1974 | Ensanian et al. |

(Continued)

FOREIGN PATENT DOCUMENTS

| CA | 2231038 A1 | 11/1999 |
| CA | 2613524 A1 | 1/2007 |

(Continued)

OTHER PUBLICATIONS

U.S. Appl. No. 13/128,631, Essex et al.

(Continued)

*Primary Examiner* — Gary Jackson
*Assistant Examiner* — Boniface N Nganga
(74) *Attorney, Agent, or Firm* — Hahn & Associates PLLC; Roger C. Hahn

(57) ABSTRACT

A method for determining biological indicators, the method including, in a processing system causing at least one radiation attenuation measurement to be performed and determining at least one first biological indicator using determined radiation attenuation. In addition to this, method includes causing at least one impedance measurement to be performed and determining at least one second biological indicator using a determined impedance measurement.

35 Claims, 30 Drawing Sheets

(56) References Cited

U.S. PATENT DOCUMENTS

| | | |
|---|---|---|
| 3,851,641 A | 12/1974 | Toole et al. |
| 3,871,359 A | 3/1975 | Pacela |
| 4,008,712 A | 2/1977 | Nyboer |
| 4,034,854 A | 7/1977 | Bevilacqua |
| 4,144,878 A | 3/1979 | Wheeler |
| RE30,101 E | 9/1979 | Kubicek et al. |
| 4,184,486 A | 1/1980 | Papa |
| 4,291,708 A | 9/1981 | Frei et al. |
| 4,314,563 A | 2/1982 | Wheeler |
| 4,353,372 A | 10/1982 | Ayer |
| 4,365,634 A | 12/1982 | Bare et al. |
| 4,401,356 A | 8/1983 | Bare |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,638,807 A | 1/1987 | Ryder |
| 4,646,754 A | 3/1987 | Seale |
| 4,686,477 A | 8/1987 | Givens et al. |
| 4,688,580 A | 8/1987 | Ko et al. |
| 4,695,955 A | 9/1987 | Faisandier |
| 4,763,660 A | 8/1988 | Kroll et al. |
| 4,793,362 A | 12/1988 | Tedner |
| 4,832,608 A | 5/1989 | Kroll |
| 4,890,630 A | 1/1990 | Kroll et al. |
| 4,895,163 A | 1/1990 | Libke et al. |
| 4,905,705 A | 3/1990 | Kizakevich et al. |
| 4,911,175 A | 3/1990 | Shizgal |
| 4,924,875 A | 5/1990 | Chamoun |
| 4,942,880 A | 7/1990 | Slovak |
| 4,951,682 A | 8/1990 | Petre |
| 5,025,784 A | 6/1991 | Shao et al. |
| 5,063,937 A | 11/1991 | Ezenwa et al. |
| 5,078,134 A | 1/1992 | Heilman et al. |
| 5,086,781 A | 2/1992 | Bookspan |
| 5,101,828 A | 4/1992 | Welkowitz et al. |
| 5,143,079 A | 9/1992 | Frei et al. |
| 5,197,479 A | 3/1993 | Hubelbank et al. |
| 5,199,432 A | 4/1993 | Quedens et al. |
| 5,246,008 A | 9/1993 | Mueller |
| 5,280,429 A | 1/1994 | Withers |
| 5,305,192 A | 4/1994 | Bonte et al. |
| 5,309,917 A | 5/1994 | Wang et al. |
| 5,311,878 A | 5/1994 | Brown et al. |
| 5,372,141 A | 12/1994 | Gallup et al. |
| 5,415,164 A | 5/1995 | Faupel et al. |
| 5,421,344 A | 6/1995 | Popp |
| 5,423,326 A | 6/1995 | Wang et al. |
| 5,449,000 A | 9/1995 | Libke et al. |
| 5,454,377 A | 10/1995 | Dzwonczyk et al. |
| 5,465,730 A | 11/1995 | Zadehkoochak et al. |
| 5,469,859 A | 11/1995 | Tsoglin et al. |
| 5,503,157 A | 4/1996 | Sramek |
| 5,505,209 A | 4/1996 | Reining |
| 5,511,553 A | 4/1996 | Segalowitz |
| 5,526,808 A | 6/1996 | Kaminsky |
| 5,529,072 A | 6/1996 | Sramek |
| 5,544,662 A | 8/1996 | Saulnier et al. |
| 5,557,242 A | 9/1996 | Wetherell |
| 5,562,607 A | 10/1996 | Gyory |
| 5,588,429 A | 12/1996 | Isaacson et al. |
| 5,596,283 A | 1/1997 | Mellitz et al. |
| 5,626,146 A | 5/1997 | Barber et al. |
| 5,679,022 A | 10/1997 | Cappa et al. |
| 5,704,355 A | 1/1998 | Bridges |
| 5,718,231 A | 2/1998 | Dewhurst et al. |
| 5,732,710 A | 3/1998 | Rabinovich et al. |
| 5,735,284 A | 4/1998 | Tsoglin et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,876,353 A | 3/1999 | Riff |
| 5,906,614 A | 5/1999 | Stern et al. |
| 5,919,142 A | 7/1999 | Boone et al. |
| 5,957,861 A | 9/1999 | Combs et al. |
| 6,006,125 A | 12/1999 | Kelly et al. |
| 6,011,992 A | 1/2000 | Hubbard et al. |
| 6,015,389 A | 1/2000 | Brown |
| 6,018,677 A | 1/2000 | Vidrine et al. |
| 6,026,323 A | 2/2000 | Skladnev et al. |
| 6,122,544 A | 9/2000 | Organ |
| 6,125,297 A | 9/2000 | Siconolfi |
| 6,142,949 A | 11/2000 | Ubby |
| 6,151,520 A | 11/2000 | Combs |
| 6,151,523 A | 11/2000 | Ferrer et al. |
| 6,173,003 B1 | 1/2001 | Whikehart et al. |
| 6,208,890 B1 | 3/2001 | Sarrazin et al. |
| 6,228,033 B1 | 5/2001 | Koobi et al. |
| 6,233,473 B1 | 5/2001 | Shepherd |
| 6,236,886 B1 | 5/2001 | Cherepenin et al. |
| 6,248,083 B1 | 6/2001 | Smith et al. |
| 6,256,532 B1 | 7/2001 | Cha |
| 6,292,690 B1 | 9/2001 | Petrucelli et al. |
| 6,339,722 B1 | 1/2002 | Heethaar et al. |
| 6,354,996 B1 | 3/2002 | Drinan et al. |
| 6,358,208 B1 * | 3/2002 | Lang et al. .................. 600/438 |
| 6,469,732 B1 | 10/2002 | Chang et al. |
| 6,472,888 B2 | 10/2002 | Oguma et al. |
| 6,496,725 B2 | 12/2002 | Kamada et al. |
| 6,497,659 B1 | 12/2002 | Rafert |
| 6,511,438 B2 | 1/2003 | Bernstein et al. |
| 6,512,949 B1 | 1/2003 | Combs et al. |
| 6,532,384 B1 | 3/2003 | Fukuda |
| 6,551,252 B2 | 4/2003 | Sackner et al. |
| 6,556,001 B1 | 4/2003 | Wiegand et al. |
| 6,560,480 B1 | 5/2003 | Nachaliel et al. |
| 6,561,986 B2 | 5/2003 | Baura et al. |
| 6,569,160 B1 | 5/2003 | Goldin et al. |
| 6,584,348 B2 | 6/2003 | Glukhovsky |
| 6,602,201 B1 | 8/2003 | Hepp et al. |
| 6,615,077 B1 | 9/2003 | Zhu et al. |
| 6,618,616 B2 | 9/2003 | Iijima et al. |
| 6,623,312 B2 | 9/2003 | Merry et al. |
| 6,625,487 B2 | 9/2003 | Herleikson |
| 6,631,292 B1 | 10/2003 | Liedtke |
| 6,633,777 B2 | 10/2003 | Szopinski |
| 6,636,754 B1 | 10/2003 | Baura et al. |
| 6,643,543 B2 | 11/2003 | Takehara et al. |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,725,089 B2 | 4/2004 | Komatsu et al. |
| 6,753,487 B2 | 6/2004 | Fujii et al. |
| 6,760,617 B2 | 7/2004 | Ward et al. |
| 6,768,921 B2 | 7/2004 | Organ et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,845,264 B1 | 1/2005 | Skladnev et al. |
| 6,870,109 B1 | 3/2005 | Villarreal |
| 6,875,176 B2 * | 4/2005 | Mourad et al. ............... 600/442 |
| 6,906,533 B1 | 6/2005 | Yoshida |
| 6,922,586 B2 | 7/2005 | Davies |
| 6,980,852 B2 | 12/2005 | Jersey-Willuhn et al. |
| 7,096,061 B2 | 8/2006 | Arad |
| 7,122,012 B2 | 10/2006 | Bouton et al. |
| 7,130,680 B2 | 10/2006 | Kodama |
| 7,148,701 B2 | 12/2006 | Park et al. |
| 7,149,573 B2 | 12/2006 | Wang |
| 7,164,522 B2 | 1/2007 | Kimura et al. |

(56) References Cited

U.S. PATENT DOCUMENTS

| | | | |
|---|---|---|---|
| 7,169,107 B2 | 1/2007 | Jersey-Willuhn et al. | |
| 7,184,820 B2 | 2/2007 | Jersey-Willuhn et al. | |
| 7,184,821 B2 | 2/2007 | Belalcazar et al. | |
| 7,186,220 B2 | 3/2007 | Stahmann et al. | |
| 7,206,630 B1 | 4/2007 | Tarler | |
| 7,212,852 B2 | 5/2007 | Smith et al. | |
| 7,214,107 B2 | 5/2007 | Powell et al. | |
| 7,233,823 B2 | 6/2007 | Simond et al. | |
| 7,251,524 B1 | 7/2007 | Hepp et al. | |
| 7,270,580 B2 | 9/2007 | Bradley et al. | |
| D557,809 S | 12/2007 | Neverov | |
| 7,353,058 B2 | 4/2008 | Weng et al. | |
| 7,390,303 B2 | 6/2008 | Dafni | |
| 7,457,660 B2 | 11/2008 | Smith et al. | |
| 7,477,937 B2 | 1/2009 | Iijima et al. | |
| D603,051 S | 10/2009 | Causevic | |
| 7,657,292 B2 * | 2/2010 | Baker et al. | 600/310 |
| 7,706,872 B2 | 4/2010 | Min et al. | |
| 7,733,224 B2 | 6/2010 | Tran | |
| 7,749,013 B2 | 7/2010 | Sato et al. | |
| 7,860,557 B2 * | 12/2010 | Istvan et al. | 600/509 |
| 7,907,997 B2 | 3/2011 | Stahmann et al. | |
| D641,886 S | 7/2011 | Causevic | |
| D647,208 S | 10/2011 | Rothman | |
| 8,233,974 B2 * | 7/2012 | Ward et al. | 600/547 |
| D669,186 S | 10/2012 | Gozani | |
| D669,187 S | 10/2012 | Gozani | |
| D674,096 S | 1/2013 | Gaw | |
| 8,467,865 B2 | 6/2013 | Gregory | |
| 8,744,564 B2 * | 6/2014 | Ward | A61B 5/0537 600/547 |
| D718,458 S | 11/2014 | Vosch | |
| D719,660 S | 12/2014 | Vosch | |
| D728,801 S | 5/2015 | Machon | |
| 2001/0007056 A1 | 7/2001 | Linder et al. | |
| 2001/0007924 A1 | 7/2001 | Kamada et al. | |
| 2001/0020138 A1 | 9/2001 | Ishigooka et al. | |
| 2001/0021799 A1 | 9/2001 | Ohlsson | |
| 2001/0025139 A1 | 9/2001 | Pearlman | |
| 2001/0049479 A1 | 12/2001 | Szopinski | |
| 2001/0051774 A1 | 12/2001 | Littrup et al. | |
| 2002/0022787 A1 | 2/2002 | Takehara et al. | |
| 2002/0035334 A1 | 3/2002 | Meij | |
| 2002/0072682 A1 | 6/2002 | Hopman et al. | |
| 2002/0072686 A1 | 6/2002 | Hoey et al. | |
| 2002/0079910 A1 | 6/2002 | Fukuda | |
| 2002/0093992 A1 | 7/2002 | Plangger | |
| 2002/0109621 A1 | 8/2002 | Khair et al. | |
| 2002/0111559 A1 | 8/2002 | Kurata | |
| 2002/0123694 A1 | 9/2002 | Organ et al. | |
| 2002/0138019 A1 | 9/2002 | Wexler et al. | |
| 2002/0161311 A1 | 10/2002 | Ward et al. | |
| 2002/0163408 A1 | 11/2002 | Fujii et al. | |
| 2002/0194419 A1 | 12/2002 | Rajput et al. | |
| 2003/0004403 A1 | 1/2003 | Drinan et al. | |
| 2003/0004433 A1 | 1/2003 | Hirschman | |
| 2003/0023184 A1 | 1/2003 | Pitts-Crick et al. | |
| 2003/0028221 A1 | 2/2003 | Zhu et al. | |
| 2003/0036713 A1 * | 2/2003 | Bouton et al. | 600/587 |
| 2003/0050570 A1 | 3/2003 | Kodama | |
| 2003/0068914 A1 | 4/2003 | Merry et al. | |
| 2003/0073916 A1 | 4/2003 | Yonce | |
| 2003/0105411 A1 | 6/2003 | Smallwood et al. | |
| 2003/0120170 A1 | 6/2003 | Zhu et al. | |
| 2003/0120182 A1 | 6/2003 | Wilkinson et al. | |
| 2003/0173976 A1 | 9/2003 | Wiegand et al. | |
| 2003/0216661 A1 | 11/2003 | Davies | |
| 2003/0216664 A1 | 11/2003 | Suarez | |
| 2004/0015095 A1 | 1/2004 | Li et al. | |
| 2004/0019292 A1 | 1/2004 | Drinan et al. | |
| 2004/0054298 A1 | 3/2004 | Masuo et al. | |
| 2004/0059220 A1 * | 3/2004 | Mourad et al. | 600/442 |
| 2004/0059242 A1 | 3/2004 | Masuo et al. | |
| 2004/0073127 A1 | 4/2004 | Istvan et al. | |
| 2004/0073130 A1 | 4/2004 | Bohm et al. | |
| 2004/0077944 A1 | 4/2004 | Steinberg | |
| 2004/0116819 A1 | 6/2004 | Alt | |
| 2004/0127793 A1 * | 7/2004 | Mendlein et al. | 600/442 |
| 2004/0158167 A1 | 8/2004 | Smith et al. | |
| 2004/0167423 A1 | 8/2004 | Pillon et al. | |
| 2004/0171961 A1 | 9/2004 | Smith | |
| 2004/0171963 A1 | 9/2004 | Takehara | |
| 2004/0181164 A1 | 9/2004 | Smith et al. | |
| 2004/0186392 A1 | 9/2004 | Ward et al. | |
| 2004/0204658 A1 | 10/2004 | Dietz et al. | |
| 2004/0210150 A1 | 10/2004 | Virtanen | |
| 2004/0210158 A1 | 10/2004 | Organ et al. | |
| 2004/0234113 A1 | 11/2004 | Miga | |
| 2004/0236202 A1 | 11/2004 | Burton | |
| 2004/0242987 A1 * | 12/2004 | Liew et al. | 600/407 |
| 2004/0242989 A1 | 12/2004 | Zhu et al. | |
| 2004/0252870 A1 | 12/2004 | Reeves et al. | |
| 2004/0253652 A1 | 12/2004 | Davies | |
| 2004/0260167 A1 | 12/2004 | Leonhardt et al. | |
| 2004/0267344 A1 | 12/2004 | Stett et al. | |
| 2005/0033281 A1 | 2/2005 | Bowman et al. | |
| 2005/0039763 A1 | 2/2005 | Kraemer et al. | |
| 2005/0070778 A1 | 3/2005 | Lackey et al. | |
| 2005/0080460 A1 | 4/2005 | Wang et al. | |
| 2005/0098343 A1 | 5/2005 | Fukuda | |
| 2005/0101875 A1 | 5/2005 | Semler et al. | |
| 2005/0107719 A1 | 5/2005 | Arad (Abboud) et al. | |
| 2005/0113704 A1 | 5/2005 | Lawson et al. | |
| 2005/0117196 A1 | 6/2005 | Kimura et al. | |
| 2005/0124908 A1 | 6/2005 | Belalcazar et al. | |
| 2005/0137480 A1 | 6/2005 | Alt et al. | |
| 2005/0151545 A1 | 7/2005 | Park | |
| 2005/0177062 A1 | 8/2005 | Skrabal et al. | |
| 2005/0192488 A1 | 9/2005 | Bryenton et al. | |
| 2005/0192511 A1 | 9/2005 | Shiokawa | |
| 2005/0201598 A1 | 9/2005 | Harel et al. | |
| 2005/0203435 A1 | 9/2005 | Nakada | |
| 2005/0203436 A1 | 9/2005 | Davies | |
| 2005/0215918 A1 | 9/2005 | Frantz et al. | |
| 2005/0228309 A1 | 10/2005 | Fisher et al. | |
| 2005/0251004 A1 * | 11/2005 | Istvan et al. | 600/395 |
| 2005/0261743 A1 | 11/2005 | Kroll | |
| 2005/0283091 A1 | 12/2005 | Kink et al. | |
| 2006/0004300 A1 | 1/2006 | Kennedy | |
| 2006/0041280 A1 | 2/2006 | Stahmann et al. | |
| 2006/0047189 A1 | 3/2006 | Takehara | |
| 2006/0064029 A1 | 3/2006 | Arad (Abboud) et al. | |
| 2006/0070623 A1 * | 4/2006 | Wilkinson et al. | 128/204.23 |
| 2006/0085048 A1 | 4/2006 | Cory et al. | |
| 2006/0085049 A1 | 4/2006 | Cory et al. | |
| 2006/0100532 A1 | 5/2006 | Bae | |
| 2006/0110962 A1 | 5/2006 | Powell et al. | |
| 2006/0111652 A1 | 5/2006 | McLeod | |
| 2006/0116599 A1 | 6/2006 | Davis | |
| 2006/0122523 A1 | 6/2006 | Bonmassar et al. | |
| 2006/0122540 A1 | 6/2006 | Zhu et al. | |
| 2006/0128193 A1 | 6/2006 | Bradley et al. | |
| 2006/0135886 A1 | 6/2006 | Lippert et al. | |
| 2006/0151815 A1 | 7/2006 | Graovac et al. | |
| 2006/0197509 A1 | 9/2006 | Kanamori et al. | |
| 2006/0200033 A1 | 9/2006 | Keren et al. | |
| 2006/0224079 A1 | 10/2006 | Washchuk | |
| 2006/0224080 A1 | 10/2006 | Oku | |
| 2006/0241513 A1 | 10/2006 | Hatlestad et al. | |
| 2006/0241719 A1 | 10/2006 | Foster et al. | |
| 2006/0247543 A1 | 11/2006 | Cornish et al. | |
| 2006/0247739 A1 | 11/2006 | Wahlstrand et al. | |
| 2006/0252670 A1 * | 11/2006 | Fiorucci et al. | 514/3 |
| 2006/0253016 A1 * | 11/2006 | Baker et al. | 600/410 |
| 2006/0253107 A1 * | 11/2006 | Hashimshony et al. | 606/1 |
| 2006/0258952 A1 | 11/2006 | Stahmann et al. | |
| 2006/0264775 A1 | 11/2006 | Mills et al. | |
| 2006/0264776 A1 | 11/2006 | Stahmann et al. | |
| 2006/0270942 A1 | 11/2006 | McAdams | |
| 2006/0293609 A1 | 12/2006 | Stahmann et al. | |
| 2007/0007975 A1 | 1/2007 | Hawkins et al. | |
| 2007/0010758 A1 | 1/2007 | Matthiessen et al. | |
| 2007/0027402 A1 | 2/2007 | Levin et al. | |
| 2007/0043303 A1 | 2/2007 | Osypka et al. | |

(56) References Cited

U.S. PATENT DOCUMENTS

| | | | |
|---|---|---|---|
| 2007/0049993 A1 | 3/2007 | Hofmann et al. | |
| 2007/0087703 A1 | 4/2007 | Li | |
| 2007/0106342 A1 | 5/2007 | Schumann | |
| 2007/0118027 A1* | 5/2007 | Baker et al. | 600/310 |
| 2007/0156061 A1 | 7/2007 | Hess | |
| 2008/0001608 A1 | 1/2008 | Saulnier et al. | |
| 2008/0002873 A1 | 1/2008 | Reeves et al. | |
| 2008/0004904 A1 | 1/2008 | Tran | |
| 2008/0009757 A1 | 1/2008 | Tsoglin et al. | |
| 2008/0009759 A1 | 1/2008 | Chetham | |
| 2008/0039700 A1 | 2/2008 | Drinan et al. | |
| 2008/0048786 A1* | 2/2008 | Feldkamp et al. | 331/16 |
| 2008/0064981 A1 | 3/2008 | Gregory | |
| 2008/0146906 A1* | 6/2008 | Baker et al. | 600/407 |
| 2008/0205717 A1 | 8/2008 | Reeves et al. | |
| 2008/0221411 A1* | 9/2008 | Hausmann et al. | 600/310 |
| 2008/0252304 A1 | 10/2008 | Woo et al. | |
| 2008/0262375 A1 | 10/2008 | Brown | |
| 2008/0270051 A1* | 10/2008 | Essex | A61B 5/0537 702/65 |
| 2008/0287823 A1 | 11/2008 | Chetham | |
| 2008/0319336 A1 | 12/2008 | Ward et al. | |
| 2009/0043222 A1 | 2/2009 | Chetham | |
| 2009/0054952 A1 | 2/2009 | Glukhovsky et al. | |
| 2009/0076343 A1 | 3/2009 | James et al. | |
| 2009/0076345 A1 | 3/2009 | Manicka et al. | |
| 2009/0076350 A1 | 3/2009 | Bly et al. | |
| 2009/0082679 A1 | 3/2009 | Chetham | |
| 2009/0084674 A1 | 4/2009 | Holzhacker et al. | |
| 2009/0105555 A1 | 4/2009 | Dacso et al. | |
| 2009/0143663 A1 | 6/2009 | Chetham | |
| 2009/0177099 A1 | 7/2009 | Smith et al. | |
| 2009/0209828 A1* | 8/2009 | Musin | 600/301 |
| 2009/0216140 A1* | 8/2009 | Skrabal | 600/509 |
| 2009/0264776 A1 | 10/2009 | Vardy | |
| 2009/0287102 A1 | 11/2009 | Ward | |
| 2009/0306535 A1 | 12/2009 | Davies | |
| 2009/0318778 A1 | 12/2009 | Dacso et al. | |
| 2010/0100003 A1 | 4/2010 | Chetham et al. | |
| 2010/0100146 A1* | 4/2010 | Blomqvist | 607/17 |
| 2010/0109739 A1 | 5/2010 | Ironstone et al. | |
| 2010/0145164 A1 | 6/2010 | Howell | |
| 2010/0168530 A1 | 7/2010 | Chetham et al. | |
| 2010/0234701 A1 | 9/2010 | Cho et al. | |
| 2011/0025348 A1 | 2/2011 | Chetham | |
| 2011/0054343 A1* | 3/2011 | Chetham et al. | 600/547 |
| 2011/0060239 A1 | 3/2011 | Gaw | |
| 2011/0087129 A1* | 4/2011 | Chetham et al. | 600/547 |
| 2011/0118619 A1 | 5/2011 | Burton et al. | |
| 2011/0190655 A1* | 8/2011 | Moissl et al. | 600/547 |
| 2011/0251513 A1 | 10/2011 | Chetham | |

FOREIGN PATENT DOCUMENTS

| | | |
|---|---|---|
| CA | 2615845 A1 | 1/2007 |
| CA | 2638958 | 11/2011 |
| CN | 1180513 A | 5/1998 |
| CN | 1236597 A | 12/1999 |
| CN | 1329875 A | 1/2002 |
| CN | 1366694 A | 8/2002 |
| CN | 101385203 A | 3/2009 |
| DE | 2912349 A1 | 10/1980 |
| EP | 249823 A1 | 12/1987 |
| EP | 339471 A2 | 11/1989 |
| EP | 349043 A2 | 1/1990 |
| EP | 357309 A2 | 3/1990 |
| EP | 377887 A1 | 7/1990 |
| EP | 581073 A2 | 2/1994 |
| EP | 662311 A1 | 7/1995 |
| EP | 865763 | 9/1998 |
| EP | 869360 A2 | 10/1998 |
| EP | 1078597 A2 | 2/2001 |
| EP | 1080686 A1 | 3/2001 |
| EP | 1112715 A1 | 7/2001 |
| EP | 1114610 A1 | 7/2001 |
| EP | 1146344 A1 | 10/2001 |
| EP | 1177760 A1 | 2/2002 |
| EP | 1219937 A1 | 7/2002 |
| EP | 1238630 A2 | 9/2002 |
| EP | 1247487 A1 | 10/2002 |
| EP | 1283539 A1 | 2/2003 |
| EP | 1329190 A1 | 7/2003 |
| EP | 1338246 A1 | 8/2003 |
| EP | 1452131 A1 | 9/2004 |
| EP | 1553871 A1 | 7/2005 |
| EP | 1629772 | 3/2006 |
| EP | 1903938 A1 | 4/2008 |
| EP | 1909642 A1 | 4/2008 |
| EP | 1948017 A1 | 7/2008 |
| FR | 2486386 A1 | 1/1982 |
| FR | 2748928 A1 | 11/1997 |
| GB | 2131558 A | 6/1984 |
| GB | 2260416 A | 4/1993 |
| GB | 2426824 | 12/2006 |
| JP | 04-096733 A | 3/1992 |
| JP | 06-000168 A | 1/1994 |
| JP | 8191808 A | 7/1996 |
| JP | 9051884 A | 2/1997 |
| JP | 9220209 A | 8/1997 |
| JP | 10000185 | 1/1998 |
| JP | 10014898 A | 1/1998 |
| JP | 10014899 A | 1/1998 |
| JP | 10-080406 A | 3/1998 |
| JP | 10-225521 A | 8/1998 |
| JP | 11070090 A | 3/1999 |
| JP | 2000107138 A | 4/2000 |
| JP | 2000139867 A | 5/2000 |
| JP | 2001037735 A | 2/2001 |
| JP | 2001-070273 A | 3/2001 |
| JP | 2001061804 A | 3/2001 |
| JP | 2001-224568 A | 8/2001 |
| JP | 2001321352 A | 11/2001 |
| JP | 2002-350477 | 4/2002 |
| JP | 2002-238870 A | 8/2002 |
| JP | 2002330938 A | 11/2002 |
| JP | 2003116805 A | 4/2003 |
| JP | 2003-230547 A | 8/2003 |
| JP | 2004-61251 A | 2/2004 |
| JP | 2005099186 A | 4/2005 |
| JP | 2005-143786 A | 6/2005 |
| JP | 2008022995 A | 2/2008 |
| NL | 001019789 C2 | 7/2003 |
| RU | 2112416 C1 | 6/1998 |
| RU | 2138193 C1 | 9/1999 |
| SU | 1132911 A1 | 1/1985 |
| WO | 8807392 A1 | 10/1988 |
| WO | 9318821 A1 | 9/1993 |
| WO | 9410922 A1 | 5/1994 |
| WO | 9601586 A1 | 1/1996 |
| WO | 9612439 A1 | 5/1996 |
| WO | 9632652 A1 | 10/1996 |
| WO | 97/11638 | 4/1997 |
| WO | 9714358 A1 | 4/1997 |
| WO | 97/24156 A1 | 7/1997 |
| WO | 9743000 A1 | 11/1997 |
| WO | 9806328 A1 | 2/1998 |
| WO | 98/23204 | 6/1998 |
| WO | 98/33553 | 8/1998 |
| WO | 9851211 A1 | 11/1998 |
| WO | 9854792 A1 | 12/1998 |
| WO | 0019886 A1 | 4/2000 |
| WO | 00/40955 | 7/2000 |
| WO | 00/79255 | 12/2000 |
| WO | 0127605 A1 | 4/2001 |
| WO | 01/50954 A1 | 7/2001 |
| WO | 01/67098 | 9/2001 |
| WO | 01/78831 A2 | 10/2001 |
| WO | 0182323 A1 | 11/2001 |
| WO | 02/47548 A1 | 6/2002 |
| WO | 02-053028 A2 | 7/2002 |
| WO | 02062214 A1 | 8/2002 |
| WO | 02094096 A1 | 11/2002 |
| WO | 02/100267 A1 | 12/2002 |
| WO | 04000115 A1 | 12/2003 |

(56) References Cited

FOREIGN PATENT DOCUMENTS

| | | |
|---|---|---|
| WO | 2004-032738 A1 | 4/2004 |
| WO | 2004026136 A1 | 4/2004 |
| WO | 2004030535 A1 | 4/2004 |
| WO | 2004032738 A1 | 4/2004 |
| WO | 2004-043252 A1 | 5/2004 |
| WO | 2004/047635 | 6/2004 |
| WO | 2004/047636 | 6/2004 |
| WO | 2004-047636 A1 | 6/2004 |
| WO | 2004/048983 | 6/2004 |
| WO | 2004047638 A1 | 6/2004 |
| WO | 2004049936 A2 | 6/2004 |
| WO | 2004083804 A2 | 9/2004 |
| WO | 2004/084723 | 10/2004 |
| WO | 2004/084724 | 10/2004 |
| WO | 2004-098389 A2 | 11/2004 |
| WO | 2005010640 A2 | 2/2005 |
| WO | 2005/027717 | 3/2005 |
| WO | 2005018432 A2 | 3/2005 |
| WO | 2005/051194 A1 | 6/2005 |
| WO | 2005/084539 | 9/2005 |
| WO | 2005/122888 | 12/2005 |
| WO | 2005122881 A1 | 12/2005 |
| WO | 2006/129108 | 12/2006 |
| WO | 2006129116 A1 | 12/2006 |
| WO | 2007/002993 | 1/2007 |
| WO | 2007002991 A1 | 1/2007 |
| WO | 2007002992 A1 | 1/2007 |
| WO | 2007009183 A1 | 1/2007 |
| WO | 2007/014417 | 2/2007 |
| WO | 2007/041783 | 4/2007 |
| WO | 2007-056493 A1 | 5/2007 |
| WO | 2007089278 A1 | 8/2007 |
| WO | 2008064426 A1 | 6/2008 |
| WO | 2008/119166 | 10/2008 |
| WO | 2008138062 A1 | 11/2008 |
| WO | 2009/018620 A1 | 2/2009 |
| WO | 2009036369 A1 | 3/2009 |
| WO | 2009/059351 | 5/2009 |
| WO | 2009/100491 | 8/2009 |
| WO | 2010/051600 | 5/2010 |
| WO | 2010/060152 | 6/2010 |
| WO | 2011022068 A1 | 2/2011 |
| WO | 2011050393 A1 | 5/2011 |
| WO | 2011075769 A1 | 6/2011 |

OTHER PUBLICATIONS

U.S. Appl. No. 13/131,859, Gaw.
U.S. Appl. No. 12/090,078, filed Feb. 12, 2009, Chetham.
European Search Report for EP 07718972.8-1265 / 2020918 (Impedimed, Ltd.), mailed on Mar. 2, 2010, 4 pages.
Brown et al.; Relation between tissue structure and imposed electrical current flow in cervical neoplasis; The Lancet; Mar. 11, 2000; vol. 355, Issue 9207: pp. 892-895.
Ellis et al.; Human hydrometry: comparison of multifrequency biolectrical impedance with 2H2O and bromine dilution; Journal of Applied Physiology; 1998; 85(3): 1056-1062.
Jones et al.; Extracellular fluid volume determined by bioelectric impedance and serum albumin in CAPD patients; Nephrology Dialysis Transplantation; 1998; 13: 393-397.
Thomas B.J.; Future technologies; Asia Pacific Journal Clinical Nutrition; 1995; 4: 157-159.
Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; Oct. 31, 1996; 5: 1934-1935.
Woodrow et al.; Effects of icodextrin in automated peritoneal dialysis on blood pressure and bioelectrical impedance analysis; Nephrology Dialysis Transplantation; 2000; 15: 862-866.
Boulier et al.; Fat-Free Mass Estimation by Two Electrode Impedance Method; American Journal of Clinical Nutrition; 1990; 52: 581-585.
McDougal et al.; Body Composition Measurements from Whole Body Resistance and Reactance; Surgical Forum; 1986; 36: 43-44.
Tedner, B.; Equipment using Impedance Technique for Automatic Recording of Fluid-Volume Changes during Hemodialysis; Medical & Biological Engineering & Computing; 1983; 285-290.
Lukaski et al.; Estimation of Body Fluid Volumes using Tetrapolar Bioelectrical Impedance Measurements; Aviation, Space, and Environmental Medicine; Dec. 1988; 1163-1169.
Lozano et al.; Two-frequency impedance plethysmograph: real and imaginary parts; Medical & Biological Engineering & Computing; Jan. 1990; 28(1): 38-42.
Chaudary et al.; Dielectric Properties of Normal & Malignant Human Breast Tissues at Radiowave and Microwave Frequencies; Indian Journal of Biochemistry & Biophysics; 1984; 21(1): 76-79.
Jossinet et al.; A study for breast imaging with a circular array of impedance electrodes; Proc. Vth Int. Conf. Bioelectrical Impedance, 1981, Tokyo, Japan; 1981; 83-86.
Jossinet et al.; Technical Implementation and Evaluation of a Bioelectrical Breast Scanner; Proc. 10.supth Int. Conf. IEEE Engng. Med. Biol., 1988, New Orleans, USA (Imped. Imaging II); 1988; 1: 289.
Man et al.; Results of Preclinical Tests for Breast Cancer Detection by Dielectric Measurements; XII Int. Conf. Med. Biol. Engng. 1979, Jerusalem, Israel. Springer Int., Berlin; 1980; Section 30.4.
Pethig et al.; The Passive Electrical Properties of Biological Systems: Their Significance in Physiology, Biophysics and Biotechnology; Physics in Medicine and Biology; 1987; 32: 933-970.
Piperno et al.; Breast Cancer Screening by Impedance Measurements; Frontiers of Medical & Biological Engineering; 1990; 2: 111-117.
Skidmore et al.; A Data Collection System for Gathering Electrical Impedance Measurements from the Human Breast; Clinical Physics Physiological Measurement; 1987; 8: 99-102.
Sollish et al.; Microprocessor-assisted Screening Techniques; Israel Journal of Medical Sciences; 1981; 17: 859-864.
Surowiec et al.; Dielectric Properties of Breast Carcinima and the Surrounding Tissues; IEEE Transactions on Biomedical Engineering; 1988; 35: 257-263.
Al-Hatib, F.; Patient Instrument Connection Errors in Bioelectrical Impedance Measurement; Physiological Measurement; May 2, 1998; 19(2): 285-296.
Gersing, E.; Impedance Spectroscopy on Living Tissue for Determination of the State of Organs; Bioelectrochemistry and Bioenergetics; 1998; 45: 145-149.
Mattar, J.A.; Application of Total Body Impedance to the Critically Ill Patient; New Horizons; 1996; 4(4): 493-503.
Ott et al.; Bioelectrical Impedance Analysis as a Predictor of Survival in Patients with Human Immunodeficiency Virus Infection; Journal of Acquired Immune Deficiency Syndromes and Human Retrovirology; 1995; 9: 20-25.
Thomas et al.; Bioelectrical impedance analysis for measurement of body fluid volumes—A review; Journal of Clinical Engineering; 1992; 17(16): 505-510.
Ward et al.; There is a better way to measure Lymphedema; National Lymphedema Network Newsletter; Oct. 1995; 7(4): 89-92.
Cornish et al.; Alteration of the extracellular and total body water volumes measured by multiple frequency bioelectrical impedance analysis; Nutrition Research; 1994; 14(5): 717-727.
Cornish et al.; Early diagnosis of lymphedema using multiple frequency bioimpedance; Lymphology; Mar. 2001; 34: 2-11.
Cornish et al.; Early diagnosis of lymphoedema in postsurgery breast cancer patients; Annals New York Academy of Sciences; May 2000; 571-575.
Brown et al.; Relation between tissue structure and imposed electrical current flow in cervical neoplasia; The Lancet; Mar. 11, 2000; 355 (9207): 892-895.
Iacobellis, G. et al.; Influence of excess fat on cardiac morphology and function: Study in Uncomplicated obesity; Obesity Research; Aug. 8, 2002; 10 (8): 767-773.
Bella, J. N. et al.; Relations of left ventricular mass to fat-free and adipose body mass: The Strong Heart Study; Circulation; Dec. 12, 1998; 98: 2538-2544.

(56) References Cited

OTHER PUBLICATIONS

Yoshinaga, M. et al.; Effect of total adipose weight and systemic hypertension on left ventricular mass in children; American Journal of Cardiology; Oct. 15, 1995; 76: 785-787.

Karason, K. et al.; Impact of blood pressure and insulin on the relationship between body fat and left ventricular structure; European Heart Journal; Jan. 1, 2003; 24: 1500-1505.

Abdullah M. Z.; Simulation of an inverse problem in electrical impedance tomography using resistance electrical network analogues; International Journal of Electrical Engineering Education; Oct. 1999; 36 (4): 311-324.

Dines et al.; Analysis of electrical conductivity imaging; Geophysics; Jul. 1981; 46 (7): 1025-1036.

Osterman et al.; Multifrequency electrical impedance imaging: preliminary in vivo experience in breast; Physiological Measurement; Feb. 2000; 21 (1): 99-109.

Ward et al.; Determination of Cole parameters in multiple frequency bioelectrical impedance analysis using only the measurement of impedances; Four-frequency fitting; Physiological Measurement; Sep. 2006; 27 (9): 839-850.

Bernstein; A new stroke volume equation for thoracic electrical bio impedance; Critical Care Medicine; 1986; vol. 14; pp. 904-909.

McAdams et al.; Tissue Impedance: a historical overview; Physiological Measurement, Institute of Physics Publishing, Bristol, GB; 16 (3A); pp. A1-A13; Aug. 1, 1995.

Forslund et al., Evaluation of modified multicompartment models to calculate body composition in healthy males, Am. J. of Clin. Nutrition, 1996; 63:856-62.

Van Loan et al., Use of bioelectrical impedance spectroscopy (BIS) to measure fluid changes during pregnancy, J. Appl. Physiol., 1995; 78:1037-42.

De Lorenzo et al., Predicting body cell mass with bioimpedance by using theoretical methods: a technological review, J. Appl. Physiol., 1997; 82(5):1542-58.

Zhu et al., Segment-specific resistivity improves body fluid volume estimates from bioimpedance spectroscopy in hemodialysis patients, J. Appl. Physiol., Oct. 27, 2005; 100:717-24.

U.S. Appl. No. 12/302,914, filed Apr. 8, 2010, McGree.

U.S. Appl. No. 12/596,833, filed Jun. 17, 2010, Ward.

U.S. Appl. No. 12/600,224, Chetham.

U.S. Appl. No. 12/672,893, filed Feb. 24, 2011, Cornish.

U.S. Appl. No. 10/767,825, filed Sep. 23, 2004, Ward.

Liu et al., Primary multi-frequency data analyze in electrical impedance scanning, Proceedings of the IEEE-EMBS 2005, 27th Annual Int'l Conference of the Engineering in Med. And Biology Soc., Shanghai, China, Sep. 4, 2005; 1504-1507.

Gudivaka et al., Single- and multifrequency models for bioelectrical impedance analysis of body water compartments, J. Appl. Physiol., 1999; 87(3):1087-96.

Thomas et al., Bioimpedance Spectrometry in the Determination of Body Water Compartments: Accuracy and Clinical Significance, Applied Radiation and Isotopes, 1998; 49(5/6):447-455, Elsevier Science Ltd., Oxford, GB.

Cornish et al., Data analysis in multiple-frequency bioelectrical impedance analysis, Physiological Measurement, 1998; 19(2):275-283, Institute of Physics Publishing, Bristol, GB.

Ulgen et al., Electrical Parameters of Human Blood, Proc. of the 20th Annual Int'l Conference of the IEEE Engineering in Medicine and Biology Soc., 1998; 20(6):2983-2986, IEEE Piscataway, N.J.

Bracco et al., Bedside determination of fluid accumulation after cardiac surgery usign segmental bioelectrical impedance, 1998, Critical Care Medicine, vol. 26 No. 6, pp. 1065-1070.

Chiolero et al., Assessmetn of changes in body water by bioimpedance in acutely ill surgical patients, 1992, Intensive Care Medicine, vol. 18, pp. 322-326.

Chumlea et al., Bioelectrical impedance and body composition: present status and future directions, 1994 Nutrition Reviews, vol. 52, No. 4, pp. 123-131.

Cornish et al., Bioelectrical impedance for monitoring the efficacy of lymphoedema treatment programmes, 1996, Breast Cancer Research and Treatment, vol. 38, pp. 169-176.

Cornish et al., Quantification of lymphoedema using multi-frequency bioimpedance, 1998, Applied Radiation and Isotopes, vol. 49 No. 5/6, pp. 651-652.

De Luca et al., Use of low-frequency electrical impedance mesurements to determine phospholipid content in amniotic fluid, 1996, Physics in Medicine and Biology, vol. 41, pp. 1863-1869.

Derwent Abstract No. 97-474414, JP 09 220209 A (Sekisui Chem Ind Co Ltd) Aug. 26, 1997, see abstract.

Derwent Abstract No. 99-138541, JP 10 014898 A (Sekisui Chem Ind Co Ltd) Jan. 20, 1998, see abstract.

Derwent Abstract No. 99-138542, JP 10 014899 A (Sekisui Chem Ind Co Ltd) Feb. 20, 1998, see abstract.

Derwent Abstract No. 99-247542, JP 11 070090 A (Sekisui Chem Ind Co Ltd) Mar. 16, 1999, see abstract.

Duerenberg et al., Multi-frequency bioelectrical impedance: a comparison between the Cole-Cole modelling and Hanai equations with the classical impedance index approach, 1996, Annals of Human Biology, vol. 23, No. 1, pp. 31-40.

Kim et al., Bioelectrical impedance changes in regional extracellular fluid alterations, 1997, Electromyography and Clinical Neurophysiology, vol. 37, pp. 297-304.

Rigaud et al., Biolectrical impedance techniques in medicine, 1996, Critical Reviews in Biomedical Engineering, vol. 24 (4-6), pp. 257-351.

Steijaert et al., The use of multi-frequency impedance to determine total body water and extracellular water in obese and lean female individuals, 1997, International Journal of Obesity, vol. 21, pp. 930-934.

Ward et al., Multi-frequency bioelectrical impedance augments the diagnosis and management of lymphoedema in post-mastectomy, 1992, European Journal of Clinical Investigation, vol. 22, pp. 751-754.

Gerth et al., A Computer-based Bioelectrical Impedance Spectroscopic System for Noninvasive Assessment of Compartmental Fluid Redistribution, Third Annual IEEE Symposium on Computer-Based Medical Systems Track 6: Clinical Assessment and Risk Evaluation/ Session 13, 1990; 446-453.

Kanai et al., Electrical measurement of fluid distribution in legs and arms, Dept. of Electrical Engineering, Sophia University, 1987; Medical Progress through Technology 12: 159-170, Copyright Martinus Nijhoff Publishers, Boston, MA USA.

d'Entremont et al. "Impedance spectroscopy: an accurate method of differentiating between viable and ischaemic or infarcted muscle tissue" Med. Biol. Eng. Comput., 2002, 40: 380-87.

Zhu et al., "Dynamics of segmental extracellular volumes during changes in body position by bioimpedance analysis"; J. App. Physiol.; 1998, vol. 85, pp. 497-504.

McCullagh, W. A., et al., Bioelectrical impedance analysis measures the ejection fraction of the calf muscle pump, IFMBE Proceedings, 2007; vol. 17, p. 619.

Scharfetter, Effect of postural changes on the reliability of volume estimations from bioimpedance spectroscopy data, Kidney International Apr. 1997, vol. 51, No. 4, pp. 1078-1087.

Ezenwa, Multiple frequency system for body composition measurement, Medical Informatics, Ethics, Cardiology, Instrumentation., Proceedings of the Annual International Conference of the Engineering in Medicine and Biology Society, Oct. 28, 1993, vol. 15, Part 02.

Yamakoshi, Non-Invasive Cardiovascular Hemodynamic Measurements, Sensors in Medicine and Health Care, 2004, pp. 107-160.

Ivorra, Bioimpedance dispersion width as a parameter to monitor living tissues, Physiological Measurement, 2005, vol. 26, S165-S173.

\* cited by examiner

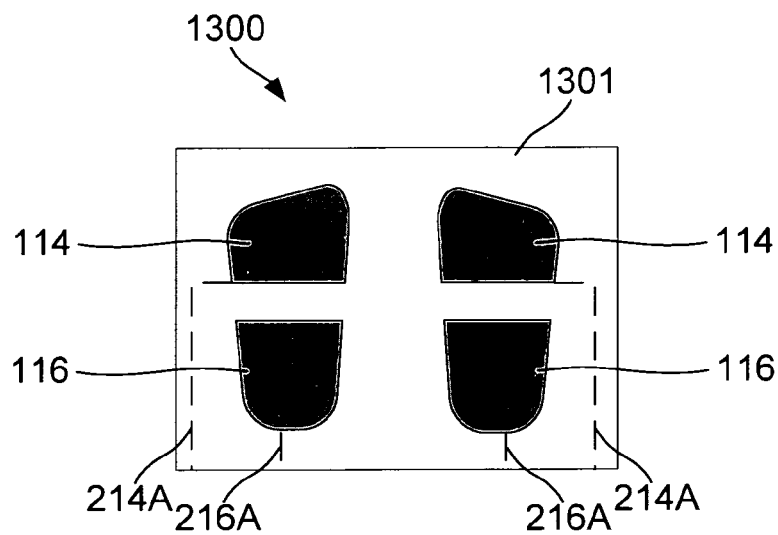
Fig. 13C
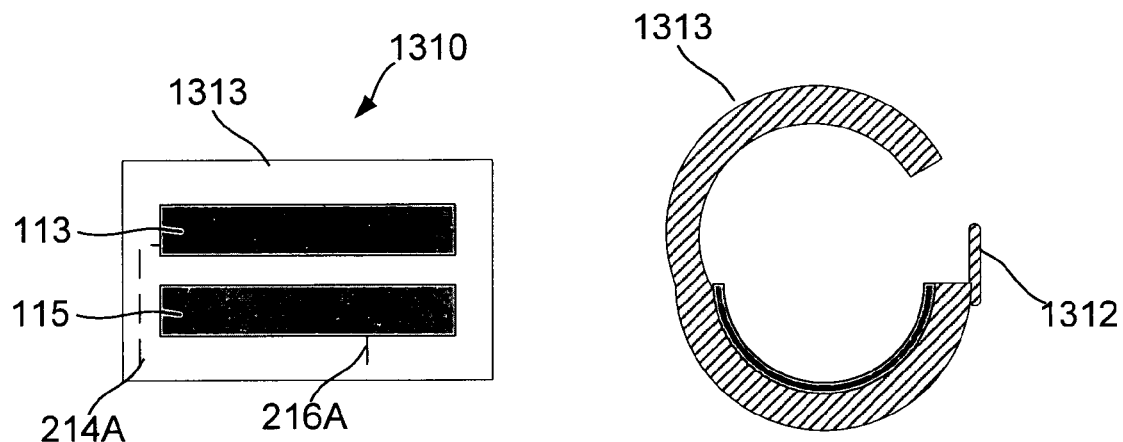
Fig. 13D  Fig. 13E

MEASUREMENT APPARATUS

BACKGROUND OF THE INVENTION

The present invention relates to a method and apparatus for determining biological indicators, and in particular to a method and apparatus for determining biological indicators using radiation attenuation and impedance measurements. The present invention also relates to a method and apparatus for use in performing impedance measurements on a subject.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

DEXA (Dual Energy X-ray Absortiometry) involves X-ray absorption scanning of a subject to determine attenuation of transmitted X-rays, which in turn allows information regarding the subject's body composition to be determined. In particular, DEXA can be used to determine a subject's bone mineral density, also known as the subject's ash weight. When combined with additional information, such as the subject's weight and intra- and extracellular fluid levels, this can be used to derive a subject's fat mass and fat-free mass.

An example DEXA apparatus used for this purpose is described in U.S. Pat. No. 6,233,473. The system described therein produces a fan-shaped distribution of x-rays and uses signal processing that corrects for mass magnification and other effects due to the geometry of the measurement system.

Additionally, DEXA can be used to detect the presence of lymphodema by using DEXA measurements to estimate relative limb volumes. However, the sensitivity of this technique is limited, in particular because changes in relative limb volume are extremely limited during early stage lymphodema. Furthermore, the DEXA procedure only images a subject in a plane, and consequently the limb volume must be derived from a cross sectional image of the limb. As this relies on assumptions regarding the relationships between limb volume and limb cross section, this can introduce additional inaccuracies.

It is also known to use DEXA to estimate visceral fat levels within a subject. However, as DEXA images a subject in a plane, again the accuracy of this technique is severely limited.

Another existing technique for determining biological indicators relating to a subject, such as cardiac function, body composition, and other health status indicators, such as the presence of oedema, involves the use of bioelectrical impedance. This process typically involves using a measuring device to measure the electrical impedance of a subject's body using a series of electrodes placed on the skin surface. Changes in electrical impedance measured at the body's surface are used to determine parameters, such as changes in fluid levels, associated with the cardiac cycle, oedema, or the like.

Impedance measuring apparatus is sometimes sensitive to external factors, including stray capacitances between the subject and the local environment and the measurement apparatus, variations in electrode/tissue interface impedances, also known as electrode impedances, as well as stray capacitances and inductive coupling between the leads used to connect the measuring device to the electrodes.

SUMMARY OF THE PRESENT INVENTION

In a first broad form the present invention provides a method for determining biological indicators, the method including, in a processing system:
   a) causing at least one radiation attenuation measurement to be performed;
   b) determining at least one first biological indicator using determined radiation attenuation;
   c) causing at least one impedance measurement to be performed; and,
   d) determining at least one second biological indicator using a determined impedance measurement.

Typically the method includes, in the processing system, causing the radiation attenuation measurement to be performed by:
   a) causing the subject to be exposed to radiation from a radiation source; and,
   b) determining attenuation of radiation transmitted through the subject.

Typically the method includes, in the processing system:
   a) causing the radiation source to scan along a length of the subject; and,
   b) receiving an indication of radiation attenuation from a detector.

Typically the method includes, in the processing system, causing the impedance measurement to be performed by:
   a) causing one or more electrical signals to be applied to the subject using a first set of electrodes;
   b) determining an indication of electrical signals measured across a second set of electrodes applied to the subject; and,
   c) determining from the indication and the one or more applied signals, at least one second biological indicator.

Typically the method includes, in the processing system:
   a) determining at least one measurement procedure to be performed; and,
   b) performing the radiation attenuation and impedance measurements in accordance with the determined measurement procedure.

Typically the method includes, in the processing system:
   a) selecting instructions corresponding to the measurement procedure; and,
   b) transferring the instructions to a second processing system, the second processing system being for:
      i) generating, using the instructions, control signals, the control signals being used to apply one or more signals to the subject;
      ii) receiving an indication of the one or more signals applied to the subject;
      iii) receiving an indication of one or more signals measured across the subject;
      iv) performing, using the instructions, at least preliminary processing of the indications to thereby allow impedance values to be determined.

Typically the method includes, in the processing system:
   a) determining at least one electrode arrangement associated with the determined measurement procedure;
   b) displaying a representation indicative of the electrode arrangement; and,
   c) causing the impedance measurement to be performed once the electrodes have been arranged in accordance with the displayed representation.

Typically the method includes, in the processing system, using the first and second biological indicators to determine at least one of:
a) an indication of the presence, absence or degree of oedema;
b) an indication of visceral fat levels;
c) an indication of segmental body composition; and,
d) an indication of body composition.

Typically the first biological indicator is indicative of at least one of:
a) the subject's bone mineral density;
b) the subject's ash weight;
c) segment volumes for one or more of the subject's body segments; and,
d) a total fat mass.

Typically the second biological indicator is indicative of fluid levels in the subject.

Typically the at least one second biological indicator is at least one of:
a) an index based on the ratio of extra- to intra-cellular fluid;
b) an index based on an impedance parameter value;
c) an intracellular fluid volume; and,
d) an extracellular fluid volume.

Typically the method includes, in the processing system:
a) comparing the at least one second biological indicator to at least one of:
i) a predetermined reference;
ii) an indicator determined for at least one other body segment; and,
iii) a previously determined indicator; and,
b) determining an indication of the presence, absence or degree of oedema using the results of the comparison.

Typically the reference includes at least one of:
a) a predetermined threshold;
b) a tolerance determined from a normal population;
c) a predetermined range; and,
d) an indicator previously determined for the subject.

Typically the method includes, in the processing system:
a) determining, using the second biological indicators, an indication of subcutaneous fat levels;
b) determining, using the first biological indicators, an indication of total fat levels; and,
c) determining an indication of visceral fat levels using the indication of subcutaneous fat levels and the indication of total fat levels.

Typically the method includes, in the processing system, determining the indication of subcutaneous fat levels using impedance measurements of at least part of the subject's abdomen.

Typically the method includes, in the processing system:
a) determining a first measured impedance indicative of a measured impedance for a first half of a first limb;
b) determining a second measured impedance indicative of a measured impedance for a second half of the first limb;
c) determining a third measured impedance indicative of a measured impedance for the first limb;
d) determining a derived impedance indicative of an impedance for the first half of the first limb using the second and third measured impedances; and,
e) comparing the first measured impedance and the derived impedance.

Typically the method includes, in the processing system:
a) determining if an electrodes are incorrectly positioned in accordance with the results of the comparison of the first measured impedance and the derived impedance; and,
b) generating an indication of any incorrectly positioned electrodes.
c) impedance measurement to be performed; and,
d) determining the impedance of at least part of the subject's abdomen; and,
e) determining the indication of subcutaneous fat levels using the impedance of at least part of the subject's abdomen.

Typically the method includes, in the processing system:
a) determining a measured impedance value for at least one body segment;
b) for each body segment, and using the measured impedance values, determining at least one impedance parameter value; and,
c) using each determined impedance value to determine the second biological indicator.

Typically the method includes, in the processing system:
a) determining at least one impedance parameter value using each determined impedance value; and,
b) determining the second biological indicator using the at least one impedance parameter value.

Typically the method includes, in the processing system:
a) determining a plurality of measured impedance values for each body segment, each measured impedance value being measured at a corresponding measurement frequency; and,
b) determining impedance parameter values based on the plurality of measured impedance values.

Typically the parameter values include $R_0$ and $R_\infty$, wherein:
$R_0$ is the resistance at zero frequency; and,
$R_\infty$ is the resistance at infinite frequency.

Typically the method includes:
a) monitoring changes over time for at least one of:
i) $R_0$;
ii) $R_\infty$;
iii) a difference between $R_0$ and $R_\infty$;
b) a vector indication of an impedance measurement.

Typically the method includes, in the processing system:
a) determining values for parameters $R_0$ and $R_\infty$ from the measured impedance values; and,
b) determining the indicator by calculating the index (I) using the equation:

$$I = \frac{R_\infty}{R_0 - R_\infty}$$

Typically the method includes, in the processing system, determining the parameter values using the equation:

$$Z = R_\infty + \frac{R_0 - R_\infty}{1 + (j\omega\tau)^{(1-\alpha)}}$$

where:
Z is the measured impedance at angular frequency $\omega$,
$\tau$ is a time constant, and
$\alpha$ has a value between 0 and 1.

Typically the method includes, in the processing system, determining the second biological indicator as an extracellular fluid volume using the equation:

$$ECV_{Segment} = C_{Segment} \rho_{Segment} \left( \frac{L_{Segment}^2}{R_{Segment}} \right)$$

Where ECV=Extracellular fluid volume
$C_{Segment}$=Geometry Constant which is 1 for an arm or leg and 4 for the thoracic cavity
$L_{Segment}$=Length of the segment in cm
$R_{Segment}$=Resistance of the segment in Ohm
$\rho_{Segment}$=Resistivity coefficient which is nominally 47 Ohm/cm Typically the method includes, in the processing system, determining an extracellular fluid volume for the entire body the equation:

$$ECV_{Total} = 2(ECV_{arm} + ECV_{leg}) + ECV_{trunk}$$

Typically the method includes, in the processing system, causing the at least one impedance measurement to be performed by:
a) causing a first signal to be applied to the subject;
b) determining an indication of a second signal measured across the subject;
c) using the indication of the second signal to determine any imbalance;
d) determining a modified first signal in accordance with the imbalance; and,
e) causing the modified first signal to be applied to the subject to thereby allow at least one impedance measurement to be performed.

Typically the method includes, in the processing system, determining the modified first signal so as to minimise the imbalance.

Typically the method is performed using apparatus including:
a) at least two electrode systems, each electrode system including:
  i) a signal generator for applying a first signal to be applied to the subject;
  ii) a sensor for sensing a second signal across the subject;
  iii) a first electrode for coupling the signal generator to the subject; and,
  iv) a second electrode for coupling the sensor to the subject; and,
b) a measuring device for controlling the electrode systems to allow impedance measurements to be performed; and,
c) at least two leads for connecting the measuring device to the electrode systems, and wherein the method includes, arranging the leads to at least one of:
  i) extend from the measuring device in different directions to thereby reduce inductive coupling therebetween; and,
  ii) minimise the lead length.

In a second broad form the present invention provides apparatus for determining biological indicators, the apparatus including a processing system for:
a) causing at least one radiation attenuation measurement to be performed;
b) determining at least one first biological indicator using determined radiation attenuation;
c) causing at least one impedance measurement to be performed; and,
d) determining at least one second biological indicator using a determined impedance measurement.

Typically the apparatus includes:
a) a radiation source for exposing the subject to radiation; and,
b) a detector for detecting radiation transmitted through the subject.

Typically the apparatus includes a drive system for moving the radiation source and detector relative to the subject, to thereby expose the subject to the radiation.

Typically the apparatus includes:
a) a support surface for supporting the subject; and,
b) one or more leads at least partially embedded within the support surface, the leads being for use in performing the impedance measurement procedure.

Typically the apparatus includes:
a) an arm for supporting a detector; and,
b) one or more leads at least partially embedded within the arm, the leads being for use in performing the impedance measurement procedure.

Typically the leads are radiolucent.

Typically the apparatus includes electrodes provided as part of at least one of:
a) a foot plate;
b) a hand plate;
c) a band electrode; and,
d) a cuff.

Typically the apparatus includes:
a) a signal generator for applying one or more electrical signals to the subject using a first set of electrodes;
b) a sensor for measuring electrical signals measured across a second set of electrodes; and,
c) a controller for:
  i) controlling the signal generator; and,
  ii) determining the indication of the measured electrical signals.

Typically the controller is for:
a) receiving instructions from the processing system;
b) generating, using the instructions, control signals, the control signals being used to apply one or more signals to the subject;
c) receiving an indication of the one or more signals applied to the subject;
d) receiving an indication of one or more signals measured across the subject;
e) performing, using the instructions, at least preliminary processing of the indications to thereby allow impedance values to be determined.

In a third broad form the present invention provides a method for use in determining visceral fat levels, the method including, in a processing system:
a) causing at least one radiation attenuation measurement to be performed;
b) determining at least one first biological indicator using determined radiation attenuation;
c) causing at least one impedance measurement to be performed;
d) determining at least one second biological indicator using a determined impedance measurement; and,
e) determining visceral fat levels using the first and second indicators.

In a fourth broad form the present invention provides a method for use in determining body composition, the method including, in a processing system:
a) causing at least one radiation attenuation measurement to be performed;
b) determining at least one first biological indicator using determined radiation attenuation;
c) causing at least one impedance measurement to be performed;

d) determining at least one second biological indicator using a determined impedance measurement; and,
e) determining body composition using the first and second indicators.

In a fifth broad form the present invention provides a method for use in diagnosing the presence, absence or degree of oedema, the method including, in a processing system:
a) causing at least one radiation attenuation measurement to be performed;
b) determining at least one first biological indicator using determined radiation attenuation;
c) causing at least one impedance measurement to be performed;
d) determining at least one second biological indicator using a determined impedance measurement; and,
e) diagnosing the presence, absence or degree of oedema using the first and second indicators.

In a sixth broad form the present invention provides apparatus for determining biological indicators, the apparatus including:
a) a radiation source for exposing a subject to radiation;
b) a detector for detecting radiation transmitted through the subject;
c) a signal generator for applying one or more electrical signals to the subject using a first set of electrodes;
d) a sensor for measuring electrical signals across a second set of electrodes; and,
e) a controller for:
    i) controlling the radiation source and the signal generator; and,
    ii) determining an indication of the radiation transmitted through the subject and the measured electrical signals.

In a seventh broad form the present invention provides a method for use in performing impedance measurements on a subject, wherein the method includes, in a processing system:
a) causing a first signal to be applied to the subject;
b) determining an indication of a second signal measured across the subject;
c) using the indication of the second signal to determine any imbalance;
d) determining a modified first signal in accordance with the imbalance;
e) causing the modified first signal to be applied to the subject to thereby allow at least one impedance measurement to be performed.

Typically the second signal is a voltage sensed at respective second electrodes; and wherein the method includes, in the processing system:
a) determining the voltage sensed at each of the second electrodes;
b) determining a first voltage using the voltage sensed at each of the second electrodes; and,
c) determining the imbalance using the first voltage.

Typically the first voltage is a common mode signal.

Typically the method includes, in the processing system, determining the modified first signal so as to minimise the imbalance.

Typically the first signal is a voltage applied to the subject using the first electrodes and the second signal is a voltage sensed at respective second electrodes, and wherein the method includes, in the processing system, performing the impedance measurement by:
a) determining a current flow caused by applying the first signal to the subject;
b) determining the voltage sensed at each of the second electrodes;
c) determining a second voltage using the voltage sensed at each of the second electrodes;
d) determining an impedance parameter using the determined current flow and the second voltage.

Typically the second voltage is a differential voltage.

Typically the first signal is a voltage applied to the subject using the first electrodes, and wherein the method includes, in the processing system, performing the impedance measurement by:
a) determining a current flow caused by applying the first signal to the subject;
b) comparing the current flow to a threshold; and,
c) selectively halting application of the first signal to the subject depending on the results of the comparison.

Typically the method includes, in the processing system, performing impedance measurements at each of a number of frequencies by:
a) causing a first signal to be applied to the subject at a first frequency;
b) determining an indication of a second signal measured across the subject;
c) using the indication of the second signal to determine an imbalance;
d) determining a modified first signal in accordance with the imbalance;
e) causing the modified first signal to be applied to the subject to thereby allow at least one impedance measurement to be performed at the first frequency; and,
f) repeating steps a) to e) for at least one second frequency.

Typically the method includes, in the processing system:
a) generating control signals, the control signals being used to apply one or more signals to the subject;
b) receiving an indication of the one or more signals applied to the subject;
c) receiving an indication of one or more signals measured across the subject; and,
d) performing at least preliminary processing of the indications to thereby allow impedance values to be determined.

In an eighth broad form the present invention provides apparatus for performing impedance measurements, the apparatus including a processing system for:
a) causing a first signal to be applied to the subject;
b) determining an indication of a second signal measured across the subject;
c) using the indication of the second signal to determine an imbalance;
d) determining a modified first signal in accordance with the imbalance;
e) causing the modified first signal to be applied to the subject to thereby allow at least one impedance measurement to be performed.

Typically the processing system is for:
a) generating control signals, the control signals being used to apply one or more signals to the subject;
b) receiving an indication of the one or more signals applied to the subject;
c) receiving an indication of one or more signals measured across the subject; and,
d) performing at least preliminary processing of the indications to thereby allow impedance values to be determined.

Typically the apparatus includes at least one signal generator for:

a) receiving one or more control signals;
b) amplifying the control signals to thereby generate the first signal;
c) applying the first signal to the subject via a first electrode; and,
d) providing an indication of a parameter relating to the first signal applied to the subject.

Typically the apparatus includes a respective signal generator for each first electrode.

Typically the first signal is a voltage, and wherein the signal generator is for providing an indication of the current flow through the subject.

Typically the apparatus includes at least one sensor for measuring the second signals via second electrodes.

Typically the apparatus includes a respective sensor for each second electrode.

Typically the apparatus includes a differential amplifier for amplifying second signals measured at each of two second electrodes.

Typically the differential amplifier generates at least one of:
a) a differential voltage indicative of the voltage measured at the second electrodes; and,
b) a common mode signal indicative of any imbalance.

Typically the apparatus includes an electrode system including:
a) a first substrate having the signal generator and sensor mounted thereon; and,
b) a second substrate having at least two conductive pads mounted thereon, the conductive pads being for coupling the signal generator and the sensor to a subject in use.

Typically the apparatus includes at least one lead for at least partially connecting a measuring device to first and second electrodes, the lead including:
a) at least two connections for connecting the measuring device and the signal generator, and the measuring device and the sensor; and,
b) a shield for each of the at least two connections, the shields being electrically connected, and connected to a reference potential in each of the measuring device and the electrode system.

Typically the apparatus includes:
a) at least two electrode systems, each electrode system including:
 i) a signal generator for applying a first signal to be applied to the subject;
 ii) a sensor for sensing a second signal across the subject;
 iii) a first electrode for coupling the signal generator to the subject; and,
 iv) a second electrode for coupling the sensor to the subject; and,
b) a measuring device for controlling the electrode systems to allow impedance measurements to be performed; and,
c) at least two leads for connecting the measuring device to the electrode systems, the leads being arranged to at least one of:
 i) extend from the measuring device in different directions to thereby reduce inductive coupling therebetween; and,
 ii) minimise the lead length.

Typically the apparatus includes an interface for coupling the processing system to a computer system, the processing system being for:

a) generating control signals in accordance with commands received from the computer system; and,
b) providing data indicative of measured impedance values to the computer system to allow impedance values to be determined.

Typically the processing system is an FPGA.

Typically the computer system is for:
a) generating commands for controlling the processing system;
b) receiving data indicative of measured impedance values from the processing system; and,
c) determining impedance values using the data.

In a ninth broad form the present invention provides apparatus for use in performing impedance measurements on a subject, wherein the apparatus includes leads for connecting a measuring device to an electrode system, the electrode system including a signal generator and a sensor, the leads including:
a) at least two connections for connecting the measuring device and the signal generator, and the measuring device and the sensor; and,
b) a shield for each of the at least two connections, the shields being electrically connected, and connected to a reference potential in each of the measuring device and the electrode system.

Typically the reference potential is a ground potential.

Typically the leads include:
a) a first cable for coupling the measuring device to the signal generator to thereby allow the measuring device to control the signal generator to apply a first signal to the subject;
b) a second cable for coupling the measuring device to the signal generator to thereby allow the measuring device to determine a parameter relating to the first signal applied to the subject; and,
c) a third cable for coupling the measuring device to the sensor generator to thereby allow the measuring device to determine a voltage measured at the subject.

Typically the electrode system includes:
a) a first substrate having the signal generator and sensor mounted thereon; and,
b) a second substrate having at least two conductive pads mounted thereon, the conductive pads being for coupling the signal generator and the sensor to a subject in use.

In a tenth broad form the present invention provides apparatus for use in performing impedance measurements on a subject, wherein the apparatus includes:
a) at least two electrode systems, each electrode system including:
 i) a signal generator for applying a first signal to be applied to the subject;
 ii) a sensor for sensing a second signal across the subject;
 iii) a first electrode for coupling the signal generator to the subject; and,
 iv) a second electrode for coupling the sensor to the subject; and,
b) a measuring device for controlling the electrode systems to allow impedance measurements to be performed; and,
c) at least two leads for connecting the measuring device to the electrode systems, the leads being arranged to at least one of:
 i) extend from the measuring device in different directions to thereby reduce inductive coupling therebetween; and, ii) minimise the lead length.

Typically the apparatus includes:
a) four electrode systems; and,
b) four leads extending from the measuring device in four different directions.

Typically the apparatus includes a support for supporting a subject's limbs to thereby position the measuring device substantially between the subject's knees.

Typically each lead includes:
a) a first cable for coupling the measuring device to the signal generator to thereby allow the measuring device to control the signal generator to apply a first signal to the subject;
b) a second cable for coupling the measuring device to the signal generator to thereby allow the measuring device to determine a parameter relating to the first signal applied to the subject; and,
c) a third cable for coupling the measuring device to the sensor generator to thereby allow the measuring device to determine a voltage measured at the subject.

Typically the electrode system includes:
a) a first substrate having the signal generator and sensor mounted thereon; and,
b) a second substrate having at least two conductive pads mounted thereon, the conductive pads being for coupling the signal generator and the sensor to a subject in use.

In an eleventh broad form the present invention provides a method of using apparatus for performing impedance measurements on a subject, wherein the apparatus includes:
a) at least two electrode systems, each electrode system including:
  i) a signal generator for applying a first signal to be applied to the subject;
  ii) a sensor for sensing a second signal across the subject;
  iii) a first electrode for coupling the signal generator to the subject; and,
  iv) a second electrode for coupling the sensor to the subject; and,
b) a measuring device for controlling the electrode systems to allow impedance measurements to be performed; and,
c) at least two leads for connecting the measuring device to the electrode systems, wherein the method includes, arranging the leads to at least one of:
  i) extend from the measuring device in different directions to thereby reduce inductive coupling therebetween; and,
  ii) minimise the lead length.

In a twelfth broad form the present invention provides a method for use in determining visceral fat levels, the method including, in a processing system:
a) causing a first signal to be applied to the subject;
b) determining an indication of a second signal measured across the subject;
c) using the indication of the second signal to determine any imbalance;
d) determining a modified first signal in accordance with the imbalance;
e) causing the modified first signal to be applied to the subject to thereby allow at least one impedance measurement to be performed.

In a thirteenth broad form the present invention provides a method of using apparatus for use in determining visceral fat levels, wherein the apparatus includes:
a) at least two electrode systems, each electrode system including:
  i) a signal generator for applying a first signal to be applied to the subject;
  ii) a sensor for sensing a second signal across the subject;
  iii) a first electrode for coupling the signal generator to the subject; and,
  iv) a second electrode for coupling the sensor to the subject; and,
b) a measuring device for controlling the electrode systems to allow impedance measurements to be performed; and,
c) at least two leads for connecting the measuring device to the electrode systems, and wherein the method includes, arranging the leads to at least one of:
  i) extend from the measuring device in different directions to thereby reduce inductive coupling therebetween; and,
  ii) minimise the lead length.

In a fourteenth broad form the present invention provides a method for use in determining body composition, the method including, in a processing system:
a) causing a first signal to be applied to the subject;
b) determining an indication of a second signal measured across the subject;
c) using the indication of the second signal to determine any imbalance;
d) determining a modified first signal in accordance with the imbalance;
e) causing the modified first signal to be applied to the subject to thereby allow at least one impedance measurement to be performed.

In a fifteenth broad form the present invention provides a method of using apparatus for use in determining body composition, wherein the apparatus includes:
a) at least two electrode systems, each electrode system including:
  i) a signal generator for applying a first signal to be applied to the subject;
  ii) a sensor for sensing a second signal across the subject;
  iii) a first electrode for coupling the signal generator to the subject; and,
  iv) a second electrode for coupling the sensor to the subject; and,
b) a measuring device for controlling the electrode systems to allow impedance measurements to be performed; and,
c) at least two leads for connecting the measuring device to the electrode systems, and wherein the method includes, arranging the leads to at least one of:
  i) extend from the measuring device in different directions to thereby reduce inductive coupling therebetween; and,
  ii) minimise the lead length.

In a sixteenth broad form the present invention provides a method for use in diagnosing the presence, absence or degree of oedema, the method including, in a processing system:
a) causing a first signal to be applied to the subject;
b) determining an indication of a second signal measured across the subject;
c) using the indication of the second signal to determine any imbalance;
d) determining a modified first signal in accordance with the imbalance;

e) causing the modified first signal to be applied to the subject to thereby allow at least one impedance measurement to be performed.

In a seventeenth broad form the present invention provides a method of using apparatus for use in determining oedema, wherein the apparatus includes:
a) at least two electrode systems, each electrode system including:
   i) a signal generator for applying a first signal to be applied to the subject;
   ii) a sensor for sensing a second signal across the subject;
   iii) a first electrode for coupling the signal generator to the subject; and,
   iv) a second electrode for coupling the sensor to the subject; and,
b) a measuring device for controlling the electrode systems to allow impedance measurements to be performed; and,
c) at least two leads for connecting the measuring device to the electrode systems, and wherein the method includes, arranging the leads to at least one of:
   i) extend from the measuring device in different directions to thereby reduce inductive coupling therebetween; and,
   ii) minimise the lead length.

It will be appreciated that the broad forms of the invention may be used individually or in combination, and may be used for diagnosis of the presence, absence or degree of a range of conditions and illnesses, including, but not limited to visceral fat, oedema, pulmonary oedema, lymphodema, body composition, cardiac function, and the like.

BRIEF DESCRIPTION OF THE DRAWINGS

An example of the present invention will now be described with reference to the accompanying drawings, in which:

FIG. 13C is a schematic diagram of the foot plate of FIGS. 13A and 13B;

FIGS. 13D and 13E are schematic diagrams of plan and side views of an example of the cuff of FIGS. 13A and 13B; and, FIGS. 14A and 14B are schematic diagrams of an example of apparatus for determining biological indicators using multiple electrode configurations.

DETAILED DESCRIPTION OF THE PREFERRED EMBODIMENTS

Figure 1A:
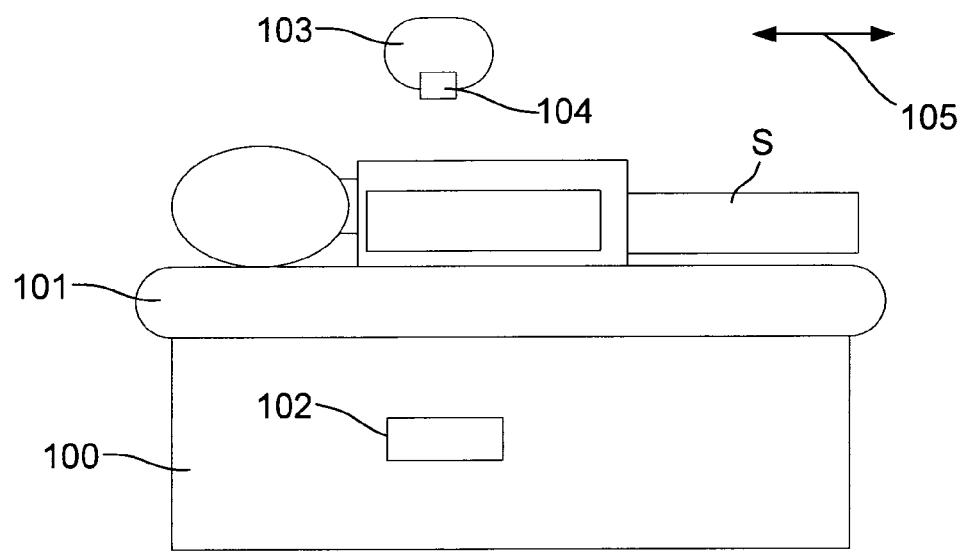
FIGS. 1A and 1B are schematic diagrams of side and plan views of an example of apparatus for determining biological indicators.

An example of apparatus for performing combined radiation attenuation and impedance measurements will now be described with reference to FIGS. 1A, 1B and 2.

The apparatus is generally formed from a base 100 having a support surface 101 for supporting a subject S in a supine position. The apparatus includes a radiation source 102 for generating radiation, such as X-rays, at at least two different energies. An arm 103 is positioned above the surface 101, aligned with the radiation source 102 allowing radiation transmitted through the subject S to be detected, using a detector 104.

The apparatus includes radiation attenuation measuring apparatus formed generally from a processing system 200, coupled to the detector 104, and a signal generator 201, which is in turn connected to a drive system 202, and the radiation source 102.

The processing system 200 is also coupled to an impedance measuring device 203, having a controller 210 coupled to a signal generator 211 and a sensor 212. In use the signal generator 211 and the sensor 212 are coupled to respective electrodes 113, 114, 115, 116 positioned on the subject S, via respective leads 213, 214, 215, 216. The connection may be via a switching device 218, such as a multiplexer, allowing the leads 213, 214, 215, 216 to be selectively interconnected to signal generator 211 and the sensor 212, as will be described in more detail below.

In use, the processing system 200 controls the signal generator 201 to cause control signals to be applied to the drive system 202. This allows the drive system 202 to be used to control the position of the radiation source 102 and the arm 103, and in particular, for allowing the radiation source 102 and the arm 103 to be moved along the length of the subject S in the direction of the arrow 105.

The processing system 200 also uses the signal generator 201 to control the radiation source 102, allowing the subject to be exposed to radiation, with an indication of the intensity of transmitted radiation being returned to the processing system 200 by the detector 104, for analysis.

The processing system 200 can also be used to control the measuring device 203, which in one example is achieved by having the processing system 200 transfer instructions indicative of an impedance measurement procedure to the controller 210. The controller 210 then causes one or more impedance measurements to be performed, returning an indication of the measured impedances, or derived impedance parameter values, to the processing system 200 for analysis.

Accordingly, it will be appreciated that the processing system may be any form of processing system which is suitable for controlling the radiation attenuation and impedance measuring apparatus and at least partially analysing measured results.

In this example, the processing system 200 includes a processor 240, a memory 241, an input/output (I/O) device 242, such as a keyboard and display, and an external interface 243, coupled together via a bus 244. It will be appreciated that the processing system 200 may therefore be a suitably programmed computer system, such as a laptop, desktop, PDA, smart phone or the like. Alternatively the processing system 200 may be formed from specialised hardware, or the like.

The external interface 243 can be used to couple the processing system 200 to the signal generator 201 and the detector 104, as well as the measuring device 203. In addition to this, the external interface 243 may be used to couple the processing system 200 to one or more peripheral devices, such as an external database or computer system or network, barcode scanner, or the like.

In use, the controller 210 is adapted to control the signal generator 211, thereby causing the signal generator 211 to generate one or more alternating signals, such as voltage or current signals, which can be applied to a subject S, via the electrodes 113, 114. The sensor 212 then determines the voltage across or current through the subject S using the electrodes 115, 116 and transfers appropriate signals to the controller 210.

Accordingly, it will be appreciated that the controller 210 may be any form of processing system, which is suitable for generating appropriate control signals and at least partially interpreting measured signals to thereby determine the subject's bioelectrical impedance, and optionally other information such as information relating to body composition, the presence, absence or degree of lymphodema, or the like.

The controller 210 may therefore be a suitably programmed computer system, but is typically formed from specialised hardware as will be described in more detail below. However, it will also be appreciated that the controller 210 may be wholly or partially implemented within the processing system 200, and that the use of a separate processing system 200 and controller 210 is for the purpose of example only.

The controller 210, the signal generator 211 and the sensor 212 may be integrated into a common housing and therefore form an integrated device. Alternatively, the controller 210 may be connected to the signal generator 211 and the sensor 212 via wired or wireless connections. This allows the controller 210 to be provided remotely to the signal generator 211 and the sensor 212. Thus, the signal generator 211 and the sensor 212 may be provided in a unit near, or worn by the subject S, whilst the controller 210 is situated remotely to the subject S.

Similarly, the controller 210 may be coupled to the processing system 200 via a wired or wireless connection, depending on the implementation, allowing the measuring device 203 to be provided remotely to the processing system 200.

In use, once the electrodes 113, 114, 115, 116 are positioned at a suitable location on the subject S, an alternating signal generated by the signal generator 211 is applied to the subject S. This may be performed either by applying an alternating signal at a plurality of frequencies simultaneously, or by applying a number of alternating signals at different frequencies sequentially. The frequency range of the applied signals may also depend on the analysis being performed.

In one example, the applied signal is a frequency rich current from a current source clamped, or otherwise limited, so it does not exceed the maximum allowable subject auxiliary current. However, alternatively, voltage signals may be applied, with a current induced in the subject being measured. The signal can either be constant current, impulse function or a constant voltage signal where the current is measured so it does not exceed the maximum allowable subject auxiliary current.

Alternatively however, an applied signal at a single frequency can be used, with the frequency of the selected signal being selected dependent on the nature of the analysis to be performed. It will be appreciated that whilst single frequency analysis is not generally as accurate, the equipment is generally less complex, and therefore cheaper, and can produce sufficiently accurate results for some circumstances.

A potential difference and/or current are measured between an inner pair of electrodes 115, 116. The acquired signal and the measured signal will be a superposition of potentials generated by the human body, such as the ECG, and potentials generated by the applied current.

Optionally the distance between the electrodes 115, 116 may be measured and recorded. Similarly, other parameters relating to the subject may be recorded, such as the height, weight, age, sex, health status, any interventions and the date and time on which they occurred. Other information, such as current medication, may also be recorded. This can be provided either to the processing system 200 or the measuring device 203, as will be described in more detail below.

To assist accurate measurement of the impedance, buffer circuits may be placed in connectors that are used to connect the voltage sensing electrodes 115, 116 to the leads 215, 216. This ensures accurate sensing of the voltage response of the subject S, and in particular helps eliminate contributions to the measured voltage due to the response of the leads 215, 216, and reduces signal loss. This in turn greatly reduces artefacts caused by movement of the leads 215, 216.

A further option is for the voltage to be measured differentially, meaning that the sensor used to measure the potential at each electrode 115 only needs to measure half of the potential, relative to the common or reference, as compared to a single ended system.

The current measurement system may also have buffers placed in the connectors between the electrodes 113, 114 and the leads 213, 214. In one example, current can also be driven or sourced through the subject S differentially, which again greatly reduced the parasitic capacitances by halving the common-mode current. Another particular advantage of using a symmetrical system is that the micro-electronics built into the connectors for each electrode 113, 114 also removes parasitic capacitances that arise and change when the subject S, and hence the leads 213, 214 move.

The acquired signal is demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a processing technique such as multiplying the measured signal with a reference sine wave and cosine wave derived from the signal generator, or with measured sine and cosine waves, and integrating over a whole number of cycles. This process rejects any harmonic responses and significantly reduces random noise.

Other suitable digital and analog demodulation techniques will be known to persons skilled in the field.

Impedance or admittance measurements are determined from the signals at each frequency by comparing the recorded voltage and current signal. The demodulation algorithm will produce an amplitude and phase signal at each frequency.

Figure 3:
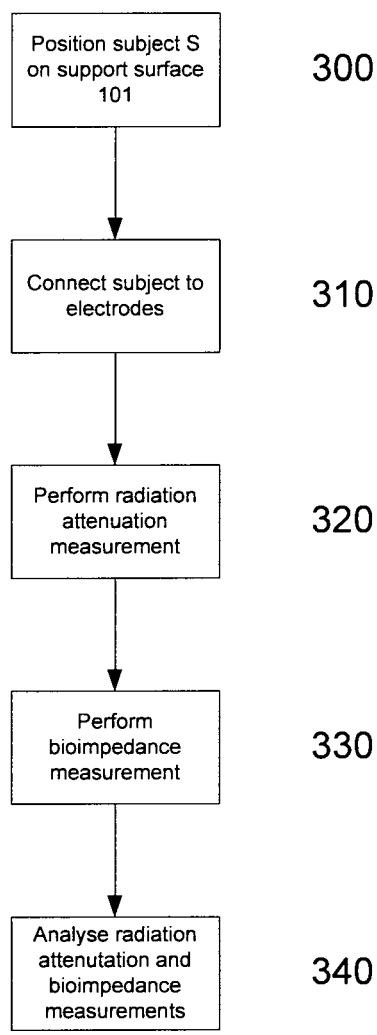
FIG. 3 is a flowchart of an example of a process for performing radiation attenuation and impedance measurements.

An example of the operation of the apparatus will now be described with reference to FIG. 3.

At step 300, the subject S is positioned on the support surface 101, with electrodes 113, 114, 115, 116 being positioned on the subject S at step 310. The electrodes 113, 115, may be provided on the subject's wrist, with the electrodes 114, 116 being provided on the subject's ankle, as shown in FIG. 1B. However, any suitable electrode configuration can be used depending on the nature of the impedance measurement being performed, as will be described in more detail below.

At step 320, radiation attenuation measurements are performed, with impedance measurements being performed at step 330. The radiation attenuation and impedance measurements are then analysed at step 340, to allow first and second biological indicators indicative of the subject's health status or body composition to be determined.

In one example, the radiation attenuation measurement is used to derive the subject's bone density and/or fat mass, with the impedance measurements being used to derive information regarding the subject's fluid levels. This in turn allows a body composition model, such as a five or six compartment model of body composition to be determined for the subject.

In another example, the impedance measurements are used to measure fluid levels within the subject's limbs and/or other body segments. This in turn allows oedema, and in particular, lymphodema to be detected. Furthermore, by performing a limb volume analysis using the radiation attenuation measurements, this allows further refinement of the lymphodema detection process.

In a further example, the impedance measurements are used to derive information regarding the subject's subcutaneous fat levels. By using the radiation attenuation measurement to derive a subject's total fat mass, this allows an indication of the subject's visceral mass to be determined.

By performing the measurements in the order described above, this has a number of benefits. Firstly, this allows the operator to prepare the subject S in a single stage, by having the subject S lie down on the support surface 101, and then attaching the electrodes. The analysis can then be performed in sequence by simply selecting a suitable measurement procedure using the processing system 200. This can allow the radiation attenuation and impedance measurements to be performed automatically without requiring further intervention.

Furthermore, by performing the radiation attenuation measurement first, this ensures the subject S remains substantially static for a period of time, allowing fluids within the subject to reach a natural homeostatic distribution, which in turn improves the accuracy of the impedance measurements. Additionally, the radiation-attenuation measurement generates a significant quantity of electrical noise, and accordingly, performing the measurements separately prevents radiation attenuation measurement from affecting the accuracy of the impedance measurements.

A specific example of the impedance measuring device 203 will now be described in more detail with respect to FIG. 4.

In this example, the controller 210 includes a second processing system 417, in the form of a processing module. A controller 419, such as a micrologic controller, may also be provided to control activation of the second processing system 417.

In use, the first processing system 200 controls the operation of the second processing system 417 to allow different impedance measurement procedures to be implemented, whilst the second processing system 417 performs specific processing tasks, to thereby reduce processing requirements on the first processing system 200.

In one example, the generation of the control signals, as well as the processing to determine instantaneous impedance values can be performed by the second processing system 417, which may therefore be formed from custom hardware, or the like. In one particular example, the second processing system 417 is formed from a Field Programmable Gate Array (FPGA), although any suitable processing module, such as a magnetologic module, may be used.

The operation of the first and second processing systems 200, 417, and the controller 419 is typically controlled using one or more sets of appropriate instructions. These could be in any suitable form, and may therefore include, software, firmware, embedded systems, or the like.

In one example, once the processing system 200 activates the measuring device 203, the controller 419 detects device activation, and executes predefined instructions, which in turn causes activation of the second processing system 417.

The first processing system 200 can then operate to control the instructions, such as the firmware, implemented by the second processing system 417, which in turn alters the operation of the second processing system 417. Additionally, the first processing system 200 can operate to analyse impedance values determined by the second processing system 417, to allow the biological indicators to be determined.

In this example, the second processing system 417 includes a PCI bridge 431 coupled to programmable module 436 and a bus 435, as shown. The bus 435 is in turn coupled to processing modules 432, 433, 434, which interface with ADCs (Analogue to Digital Converters) 437, 438, and a DAC (Digital to Analogue Converter) 439, respectively.

The programmable module 436 is formed from programmable hardware, the operation of which is controlled using the instructions, which are typically downloaded from the first processing system 200. The firmware that specifies the configuration of hardware 436 may reside in flash memory (not shown), in the memory 241, or may be downloaded from an external source via the external interface 243.

Alternatively, the instructions may be stored within inbuilt memory on the second processing system 417. In this example, the first processing system 200 typically selects firmware for implementation, before causing this to be implemented by the second processing system 417. This may be achieved to allow selective activation of functions encoded within the firmware, and can be performed for example using configuration data, such as a configuration file, or instructions representing applications software or firmware, or the like.

In either case, this allows the first processing system 200 to be used to control operation of the second processing system 417 to allow predetermined current sequences to be applied to the subject S. Thus, for example, different firmware would be utilised if the current signal is to be used to analyse the impedance at a number of frequencies simultaneously, for example, by using a current signal formed from a number of superposed frequencies, as compared to the use of current signals applied at different frequencies sequentially. Modifying the firmware in this manner allows a range of different current sequences to be applied to the subject simply by having the operator make an appropriate measurement type selection.

Once the measurement procedure is selected and the firmware configured as required, the FPGA operates to generate a sequence of appropriate control signals $I^+$, $I^-$, which are applied to the subject S. The voltage V induced across the subject is sensed using the sensor 112, allowing the impedance values to be determined and analysed by the second processing system 417.

It will be appreciated that the division of processing between the first processing system 200, and the second processing system 417, is not essential, but there are a number of benefits that will become apparent from the remaining description.

Firstly, the use of a second processing system 417 allows the custom hardware configuration to be adapted through the use of appropriate firmware. This in turn allows a single measuring device 203 to be used to perform a range of different types of analysis.

Secondly, this vastly reduces the processing requirements on the first processing system 200. This in turn allows the first processing system 200 to be implemented using relatively straightforward hardware, whilst still allowing the measuring device to perform sufficient analysis to provide interpretation of the impedance. This can include for example generating a "Complex impedance plot", using the impedance values to determine biological indicators, or the like.

Thirdly, this allows the measuring device 203 to be updated. Thus for example, if an improved analysis algorithm is created, or an improved current sequence determined for a specific impedance measurement type, the measuring device can be updated by downloading new firmware via flash memory (not shown) or the external interface 243.

However, whilst processing is performed partially by the second processing system 417, and partially by the first processing system 200, it is also possible for processing to be performed by a single element, such as an FPGA, or a more generalised processing system.

As the FPGA is a customisable processing system, it tends to be more efficient in operation than a more generic processing system. As a result, if an FPGA alone is used, it is generally possible to use a reduced overall amount of processing, allowing for a reduction in power consumption and size. However, the degree of flexibility, and in particular, the range of processing and analysis of the impedance which can be performed is limited.

Conversely, if only a generic processing system is used, the flexibility is enhanced at the expense of a decrease in efficiency, and a consequent increase in size and power consumption.

Accordingly, the above described example strikes a balance, providing custom processing in the form of an FPGA to perform partial processing. This can allow for example, the impedance values to be determined. Subsequent analysis, which generally requires a greater degree of flexibility can then be implemented with the generic processing system.

Figure 5A:
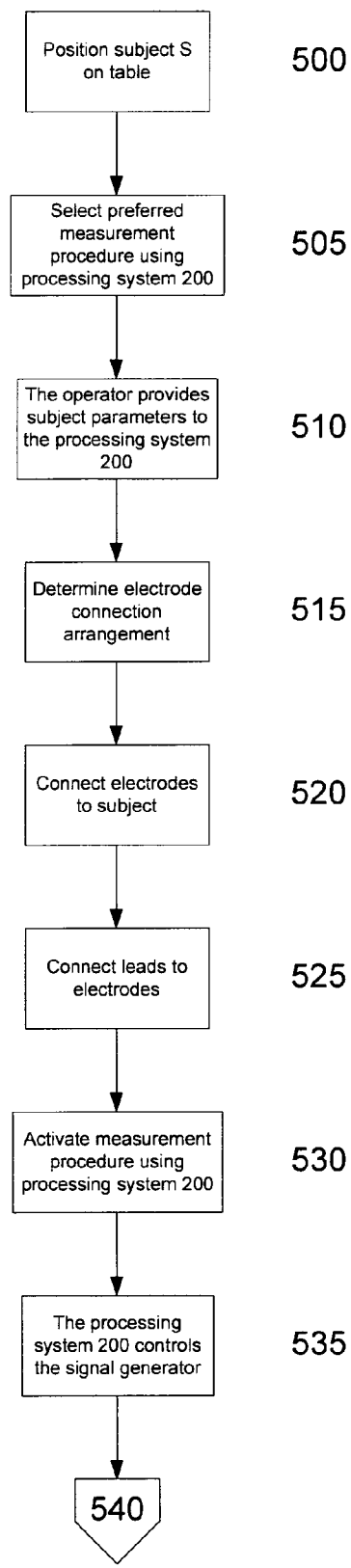
FIGS. 5A and 5B are a flow chart of a second example of a process for performing radiation attenuation and impedance measurements.
Figure 5B:
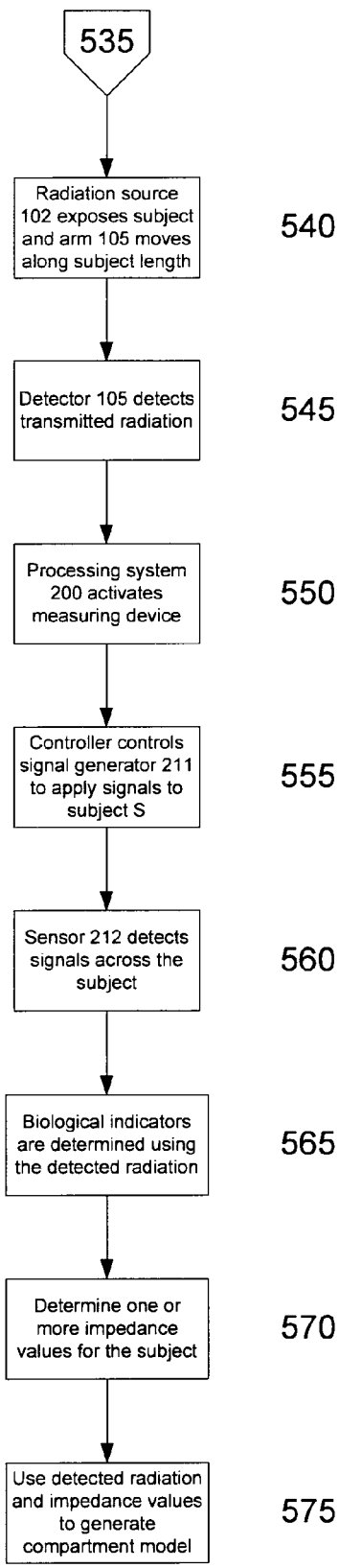

An example of the measurement procedure will now be described in more detail with respect to FIG. 5.

In this example, the subject S is positioned on the support surface 101 at step 500, with a measurement procedure being selected using the processing system 200 at step 505. This is typically achieved by having the processing system 200 display a user interface including a list of available measurement procedures, allowing a desired procedure to be selected using the I/O device 242. Additionally, or alternatively, the operator can define custom procedures.

Available procedures are typically stored as profiles in the memory 241, and describe the sequence of measurements that are to be performed. This includes information regarding the signals that need to be generated by the signal generators 201, 211, and the relative timing with which the signals should be applied. The profiles also include an indication of calculations that need to be performed on recorded measurements, to allow body composition or health status indicators to be determined.

Shown notionally at step 510, but performable at any time, additional information regarding the subject, referred to generally as subject parameters, may be supplied to the processing system 200. This is typically performed by having the processing system determine any information that is required from the profile, and then display a user interface allowing the operator to input the information. This can include but is not limited to parameters such as the height, age, weight, sex, and ethnicity of the subject, as well as details of any medical interventions, such as performed medical procedures. The subject parameters may be used for a number of reasons, such as to allow references to be selected, as will be described in more detail below. This process may be performed simultaneously with the following measurement procedure, allowing the operator to enter the subject parameters whilst the measurements are performed.

At step 515, the processing system 200 displays an indication of an electrode positioning as determined from the profile data. This can be achieved in any suitable manner, but typically involves displaying a visual representation of a subject S with the required electrode positions displayed. At step 520, the operator connects the electrodes to the subject S in accordance with the displayed electrode positioning.

Figure 1B:
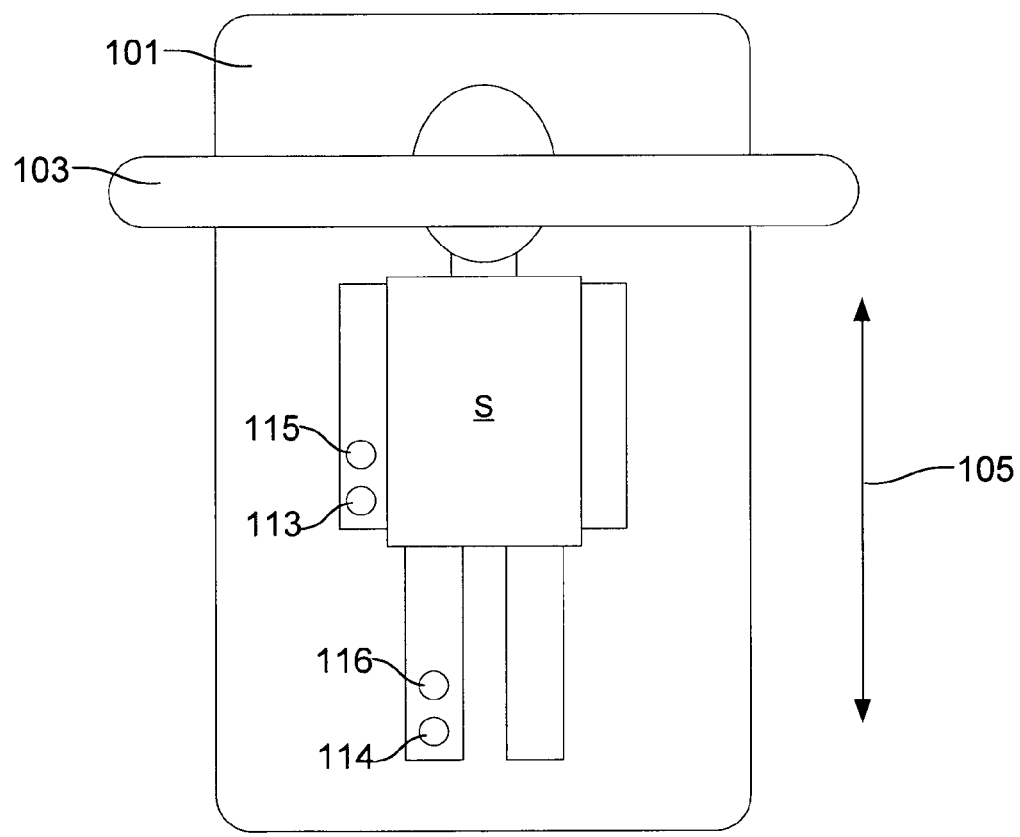

The electrodes 113, 114, 115, 116 may be positioned as shown for example in FIG. 1B, with current supply electrodes 113, 114, being positioned near the hand and foot respectively, whilst the voltage sensing electrodes 115, 116 are positioned inwardly of the current supply electrodes 113, 114, on the wrist and ankle respectively.

However, it may be necessary to record measurements with a number of different electrode configurations. This may be required, for example, to record impedance measurements for a number of different body segments independently. Example configurations are shown in FIGS. 6A to 6D.

In this regard, the electrode configurations shown in FIGS. 6A to 6D involve positioning electrodes on the limbs of the subject S, with the particular electrode placement allowing the impedance of different body segments to be measured.

Figure 6A:
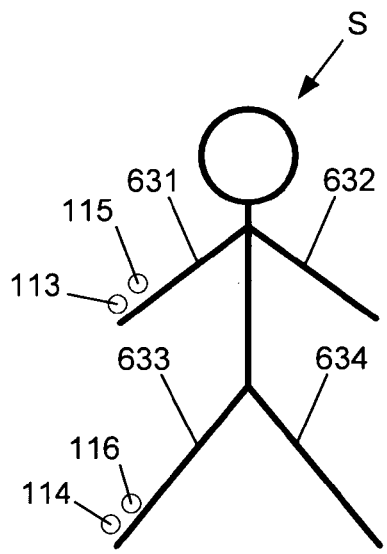
FIGS. 6A to 6D are schematic diagram of examples of different electrode arrangements for use in the process of FIGS. 4A and 4B.
Figure 6B:
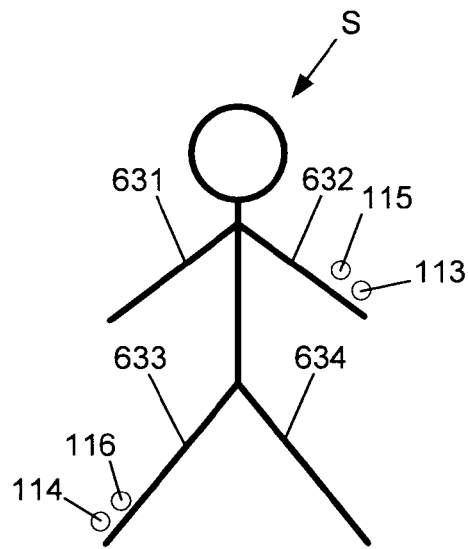
Figure 6C:
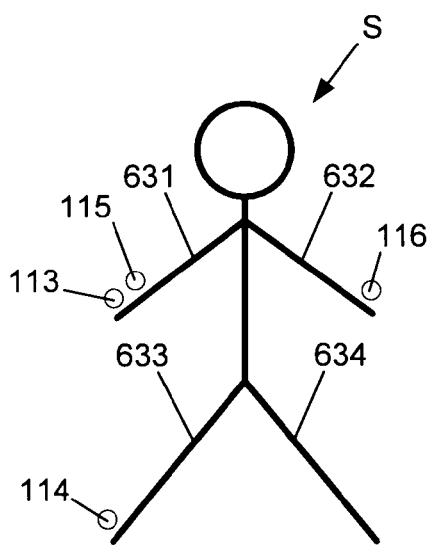
Figure 6D:
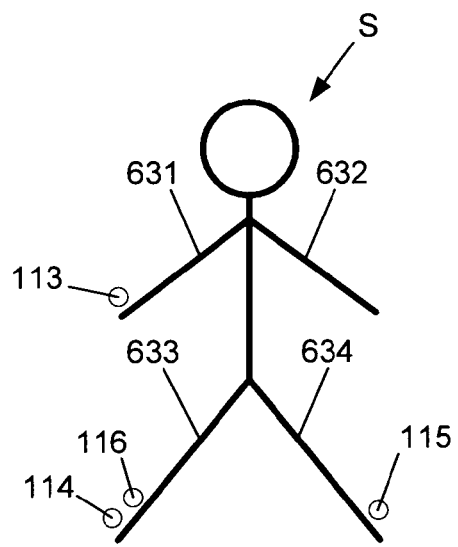

In the examples of FIGS. 6A and 6B, the configuration allows the impedance of the entire subject to be determined, whereas the configurations shown in FIGS. 6C and 6D allow the right arm 631 and the right leg 633 to be measured respectively. It will be appreciated that equivalent electrode arrangements can also be used to measure the left arm 632 and the left leg 634.

In general, when such an electrode arrangement is used, electrodes may be provided in each possible electrode placement position, with leads being connected selectively to the electrodes as required. Alternatively, respective leads may be provided for each electrode with the switching unit 218 operating to selectively connect the electrodes to the signal generator 211 or the sensor 212, thereby allowing a sequence of different measurements to be performed on different subject segments.

It will be appreciated that this configuration uses the theory of equal potentials, allowing the electrode positions to provide reproducible results for impedance measurements. For example when current is injected between electrodes 113 and 114 in FIG. 6C, the electrode 117 could be placed anywhere along the left arm 632, since the whole arm is at an equal potential.

This is advantageous as it greatly reduces the variations in measurements caused by poor placement of the electrodes by the operator. It also greatly reduces the number of electrodes required to perform segmental body measurements, as well as allowing the limited connections shown to be used to measure each of limbs separately.

Figure 6E:
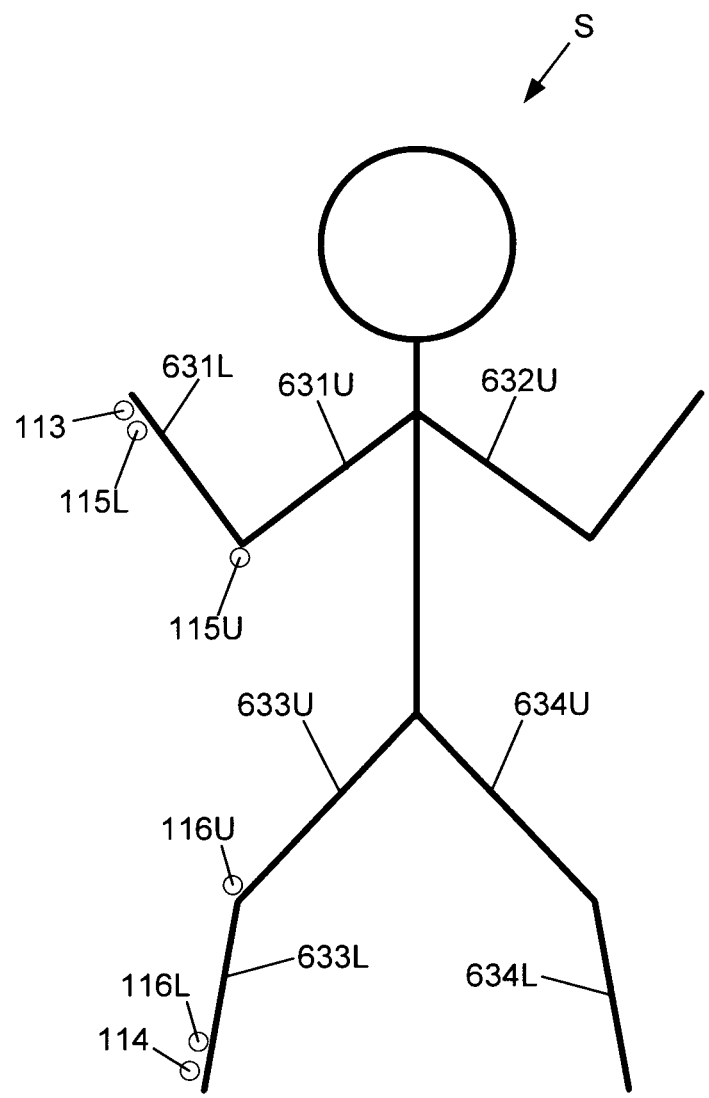
FIG. 6E is a schematic diagram of an example of an electrode arrangements for use measuring half limb segments.

In the above examples, the configurations allow measurements to be made relating to entire limbs. However, additionally and/or alternatively, it may be desirable to measure the impedance of smaller body segments, such as half limbs. An example of the electrode configuration for measuring the impedance of half-limbs will now be described with respect to FIG. 6E.

In this example, the arms 631, 632, and legs 633, 634, are divided into upper and lower sections, by the elbows and knees respectively, with the upper and lower sections being designated by the suffixes u, l respectively.

To allow the impedance of the half limb segments to be measured, additional voltage sensing electrodes 115, 116 are provided. In this example, lower voltage sensing electrodes 115L, 116L are positioned on the wrist and ankle respectively, whilst upper voltage sensing electrodes 115U, 116U are positioned on the subject's elbow and knee respectively.

In this example, if it is desired to measure the lower half limb, such as the lower arm 631L, the voltage induced within the lower arm is measured between the electrodes 115L, 115U. Similarly, if the impedance of the lower leg 633L is to be measured, the induced voltage would be sensed via the electrodes 116U, 116L.

In contrast to this, if the upper half of a limb is to be measured, then utilising the theory of equal potentials, this can be achieved by measuring potential induced between the electrodes 115U, 116L, or the electrodes 115L, 116U, as will be appreciated by persons skilled in the art.

It will be appreciated that in this example electrodes are only provided on limbs on one side of the subject S. However, in practice measurements of contralateral limbs can be made in a similar manner, as will be described in more detail below.

A further variation that can be achieved using the above technique is to compare the results of impedance measurements for half-limbs that are derived via different mechanisms.

For example, the impedance of the lower half limb can be determined by direct measurement of induced voltages using the electrodes 115L, 115U, for the lower arm, or 116L, 116U for the lower leg.

Alternatively, the impedance of a half limb can be determined by measuring the impedance of the entire limb, and then subtracting the impedance of the other half limb. Thus, the impedance of the lower arm could be determined by measuring the impedance of the entire arm, using the electrodes 115L, 116L, and then subtracting the impedance of the upper arm, as determined using the electrodes 115U, 116L.

In theory, assuming the electrodes are correctly positioned, then the impedance determined for a half limb using the two different techniques should be equal. Accordingly, in one example, the processing system 200 operates to determine the impedance of one or more half limbs using both techniques, and then compares the results. In the event that the impedance values determined using the two techniques do not agree, then this indicates that one or more of the electrodes may be incorrectly positioned.

Thus, the processing system 200 cause impedance measurements to be performed to determine first, second and third measured impedance values for a first half of a limb, a second half of the limb and the entire limb, respectively. Once this has been completed, the processing system can determine a derived impedance for the first half of the limb using the second and third measured impedance values, before comparing the first measured impedance value and the derived impedance value. It will be appreciated that the processing system can then use the results of this comparison to determine which of the electrodes, if any, are incorrectly positioned.

Accordingly, in use the processing system 200 can be adapted to perform the impedance measurements for each half limb, and compare the results, to thereby automatically determine if any of the electrodes are positioned incorrectly. In the event that any electrodes are incorrectly positioned, the processing system 200 can then generate an indication of this, allowing the operator to correct the positioning.

In order to prevent the electrodes interfering with the radiation attenuation measurement process, radiolucent electrodes may be used. However, electrodes that are at least partially radiopaque may be used to allow the position of the electrodes to be determined from the radiation transmitted through the subject S, which can be used in the subsequent analysis to help mitigate poor electrode placement, as well as allowing the electrode geometry and in particular the electrode separation to be determined automatically.

Additionally, the result of the radiation attenuation measurement procedure can be used to determine additional subject parameters, such as limb lengths, which can in turn be used in analysing the impedance measurements. This allows a more accurate model of body composition or visceral fat to be determined, as well as allowing for improved lymphodema detection.

Figure 7A:
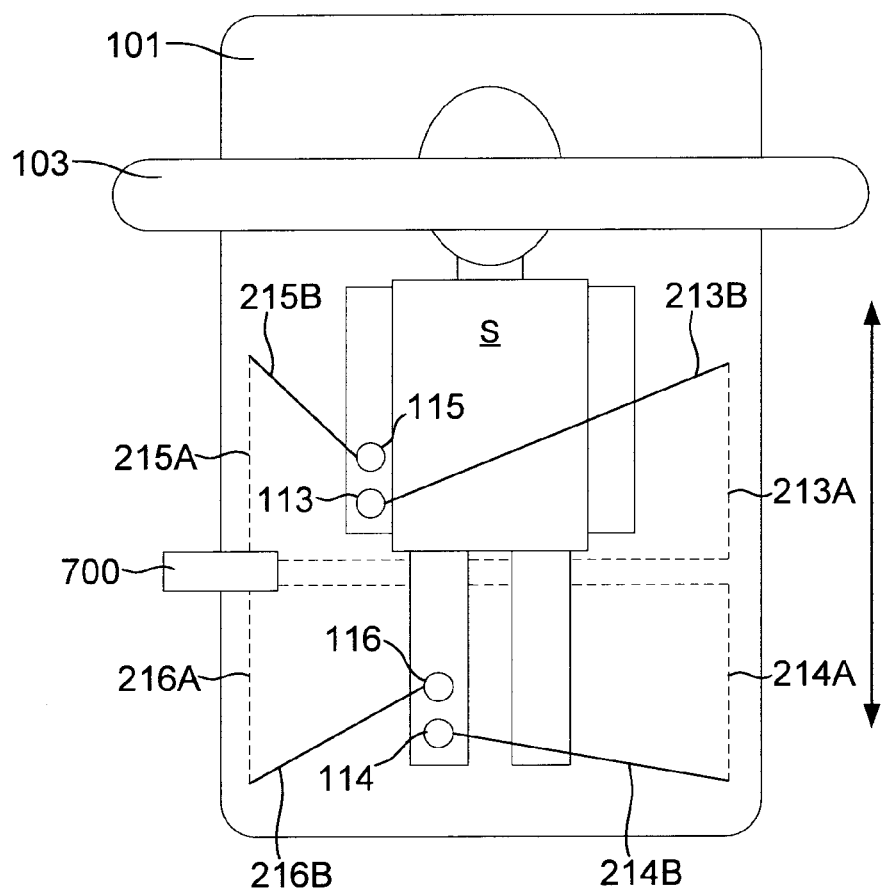
FIGS. 7A and 7B are schematic diagrams of plan and side views of an example of a lead configuration for use in the apparatus of FIGS. 1A and 1B.
Figure 7B:
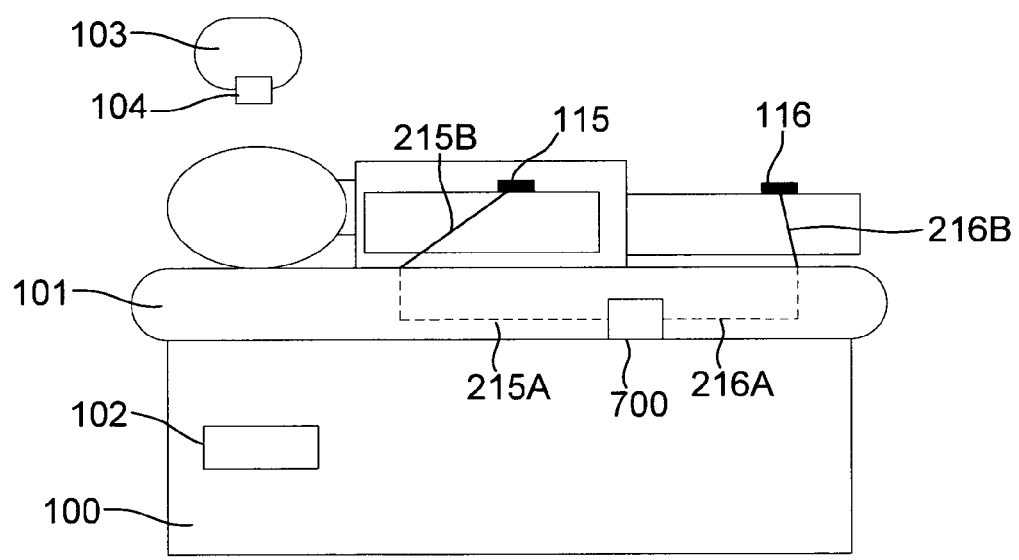

At step 525 the electrodes are connected to the leads 213, 214, 215, 216. An example lead configuration is shown in FIGS. 7A and 7B. In FIG. 7B, only two of the electrodes 115, 116 and corresponding leads 215, 216 are shown for clarity, although it will be appreciated that in practice electrodes 113, 114 and corresponding leads 213, 214 will also be provided in a similar manner.

In this example, a connector 700 is provided, for allowing the measuring device 203 to be connected to the leads 213, 214, 215, 216. This may be in the form of a cradle adapted to receive the measuring device 203, although any suitable connection system may be used. Thus, for example, the connector 700 could be replaced by the measuring device 203, allowing the measuring device 203 to be connected to the leads 213, 214, 215, 216 directly.

In this example, the connector 700 is also coupled to embedded leads 213A, 214A, 215A, 216A integrated into the support surface 101, and which extend under the support surface 101 to four separated locations on the support surface 101. From here, the external leads 213B, 214B, 215B, 216B are used to connect to the electrodes 113, 114, 115, 116. The external leads 213B, 214B, 215B, 216B may be mounted to a retraction mechanism allowing the external leads to be detracted into the support surface 101, when not in use.

By providing a combination of embedded and external leads in this manner has a number of benefits.

Firstly, it makes the process of connecting the electrodes to the leads far easier for the operator, as the operator need simply connect the external leads 213B, 214B, 215B, 216B to the electrodes 113, 114, 115, 116. For example, this avoids problems with leads being incorrectly connected to the measuring device 203. It also allows a visual indication on each external lead 213B, 214B, 215B, 216B, or on the support surface 101 where the external lead is provided, indicating to which electrode 113, 114, 115, 116 each lead 213B, 214B, 215B, 216B should be connected, in turn ensuring correct connection.

Secondly, it helps ensure adequate spacing of the leads, which helps to reduce magnetic coupling between the leads. Such magnetic coupling occurs because the alternating current in the leads 213, 214, generates a changing magnetic field in the vicinity of the current leads 213, 214, which in turn induces a current in the voltage leads 215, 216. Accordingly, maximising the separation of the current and voltage leads, as well as minimising the voltage lead length, can reduce the magnitude of the induced current and hence can improve the accuracy of the impedance measurements.

Further improvement can also be obtained by providing appropriate lead shielding. When shielding the external leads 213B, 214B, 215B, 216B, the level of shielding is limited by the need to maintain lead flexibility to allow connection to the electrodes. Furthermore, in the case of the internal leads, as these are integrated into the support surface 101 the leads do not move and hence can incorporate heavy shielding thereby further reducing magnetic coupling effects.

It will be appreciated that in order to prevent the leads 213, 214, 215, 216 interfering with the radiation attenuation measurement, the leads may be radiolucent. However, alternatively radiopaque leads may be used to allow the lead connections to the electrodes to be viewed using the radiation attenuation measurements.

At step 530, the measurement procedure is activated using the processing system 200. Accordingly, once the operator has connected the leads to the electrodes, and the subject S is ready for the procedure to commence, the operator can use the interface displayed by the processing system 200 to start the procedure.

At step 535, the processing system 200 controls the signal generator 201 causing the signal generator to generate control signals, which are transferred to the radiation source 102 and the drive system 202. At step 540, this causes the radiation source 102 to generate a beam of radiation at at least two predetermined energies. Simultaneously, the drive system 202 causes the detector 102 and the arm 103 to move along the length of the support surface 101, thereby exposing the subject S to the radiation. At step 545, the detector 104 senses the radiation transmitted through the subject S and transfers signals indicative of the sensed radiation to the processing system 200 for analysis, and in particular to allow radiation attenuation to be determined.

At step 550, the processing system 200 activates the measuring device 203 to allow the impedance measurements to be performed. At step 555, the controller 210 controls the signal generator 211 to generate current signals at a number of different frequencies $f_i$. The signals may be formed from superposed signals applied simultaneously or from a sweep through a number of frequencies in turn. Signals indicative of the magnitude of the applied current are typically returned to the controller 210, allowing the controller 210 to determine the magnitude of the applied current signal $C_i$ at each applied frequency $f_i$.

Voltages across the subject S are then measured by the sensor 212 at step 560, with signals indicative of the measured voltages being transferred to the controller 210. The measurement process is controlled by sampling the voltage signals in synchronisation with the applied current signals, so that the controller can determine a respective measured voltage $V_i$ for each applied current signal $C_i$ at each applied frequency $f_i$.

At step 565, the processing system 200 determines one or more first biological indicators from the radiation measured during the radiation attenuation measurement process. The first biological indicators can include the subject's bone density or ash weight, as well as estimations of volumetric information regarding limbs or other segments of the subject. It will be appreciated that again, whilst this is shown at step 565, this process could be performed during the impedance measurement procedure. The manner in which this is achieved is typically controlled using information stored in the profile, and the calculation of such indicators will generally be known to those skilled in the art.

At this stage, the processing system 200 may also analyse the radiation attenuation measurements to determine information regarding electrode positioning, such as electrode separation, as well as to determine information regarding subject parameters such as limb length. This information may then be used by the processing system 200 and/or the processing system 417, during the analysis of the impedance measurements.

At step 570, the processing system 200 or second processing system 417 determines instantaneous impedance values at each frequency $f_i$, allowing impedance parameter values to be determined. This in turn allows second biological indicators to be determined, such as values of $R_0$ and $R_\infty$, the ratio of intracellular fluid to extracellular fluid, or the like, as will be described in more detail below. The manner in which this is achieved is typically controlled using information stored in the profile.

An example of the determination of second biological indicators from the impedance measurements will now be described in more detail. In particular, in one example, the second processing system 417 operates to determine the instantaneous impedance of the body segment being measured, at each frequency, with the first processing system 200 using this information to determine $R_0$ and $R_\infty$ for the body segment.

This can be achieved in a number of manners as will now be described.

Figure 8:
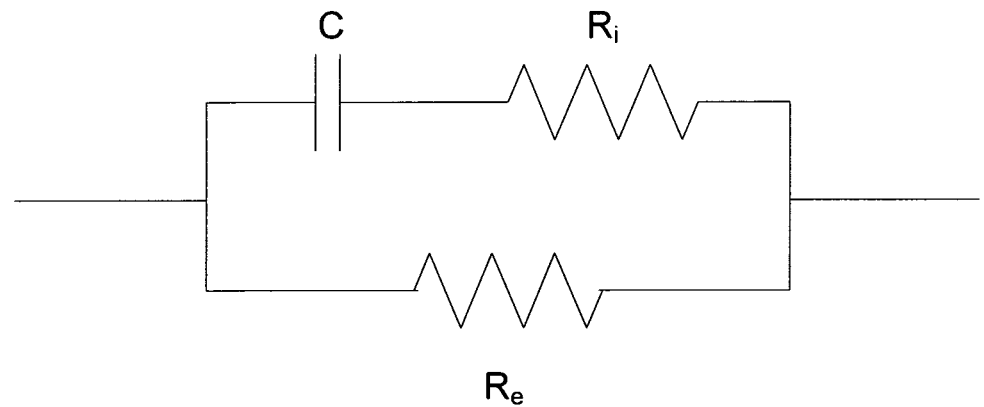
FIG. 8 is a schematic of an example of an equivalence circuit for modelling a subject's impedance response.

In this regard, FIG. 8 is an example of an equivalent circuit that effectively models the electrical behaviour of biological tissue. The equivalent circuit has two branches that represent current flow through extracellular fluid and intracellular fluid. The extracellular component of biological impedance is represented by $R_e$ and the intracellular component is represented by $R_i$. Capacitance associated with the cell membrane is represented by C.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals $R_e$. At infinite frequency the capacitor acts as a perfect conductor and the current passes through the parallel resistive combination. The resistance at infinite frequency is given by $R_\infty = R_i R_e/(R_i + R_e)$.

Accordingly, the impedance of the equivalent circuit of FIG. 8 at an angular frequency ω, where ω=2π*frequency, is given by:

$$Z = R_\infty + \frac{R_0 - R_\infty}{1 + (j\omega\tau)} \quad (1)$$

where: $R_\infty$=impedance at infinite applied frequency=$R_i R_e/(R_i + R_e)$,
$R_0$=impedance at zero applied frequency=$R_e$ and,
τ is the time constant of the capacitive circuit.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^{(1-\alpha)}} \quad (2)$$

where α has a value between 0 and 1 and can be thought of as an indicator of the deviation of a real system from the ideal model.

Figure 9:
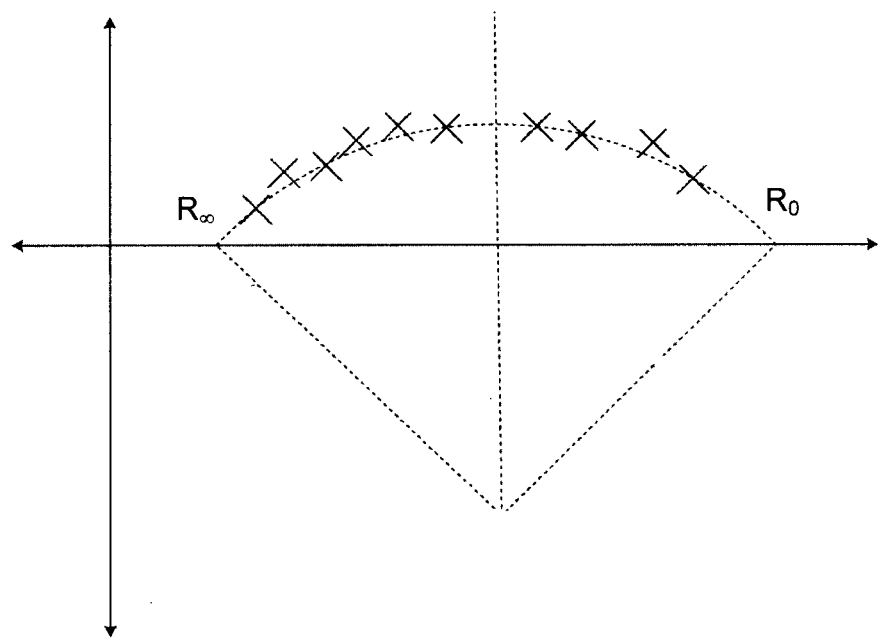
FIG. 9 is an example of a "Complex impedance plot" of a subject's impedance response.

The value of the impedance parameters $R_0$ and $R_\infty$ may be determined in any one of a number of manners such as by:
  solving simultaneous equations based on the impedance values determined at different frequencies;
  using iterative mathematical techniques;
  extrapolation from a "Complex impedance plot" similar to that shown in FIG. 9;
  performing a function fitting technique, such as the use of a polynomial function.

The above described equivalent circuit models the resistivity as a constant value and does not therefore accurately reflect the impedance response of a subject or other relaxation effects. To more successfully model the electrical conductivity of a human, an improved CPE based may alternatively be used.

At this stage the first processing system 200 or second processing system 417 can also be adapted to test adherence of the measurements to the Cole model. In particular, the Cole model assumes that the impedance measurements lie on a semi-circular impedance locus. Accordingly, the first processing system 200 can determine if the measured values fit a semi-circular locus to thereby determine if the Cole model is satisfied. Alternatively, the measured impedance parameter values can be compared to theoretical values derived using the equation (2), to thereby allow the degree of concordance to the Cole model to be determined.

In the event that the Cole model is not satisfied, an indication of this can be provided to the operator allowing an appropriate analysis technique to be utilised.

In any event, it will be appreciated that any suitable technique for determination of the impedance parameter values $R_0$ and $R_\infty$ may be used.

The determination of impedance parameter values may be performed for a single body segment, such as the entire body, using the electrode arrangements shown in FIG. 6A or 6B. Alternatively, the may be performed on a number of smaller body segments, such as the limbs, and/or thoracic cavity separately, using for example the electrode configurations shown in FIGS. 6C to 6D, or half limbs using the electrode configuration of FIG. 6E. A combination of the two approaches may also be used. The electrode configurations can also be selected automatically using a switching device 218.

Once required impedance parameters values such as $R_0$ and $R_\infty$ have been determined all body segments required by the selected measurement procedure, the processing system 200 uses the values together with information obtained from the radiation attenuation measurement procedure.

At step 575, the processing system 200 uses the determined biological indicators to generate a five or six compartment body composition model, or alternatively to perform lymphodema detection as will be described in more detail below.

This process may utilise one or more predetermined references.

The reference can be based on predetermined normal ranges derived, for example, from a study of a number of other individuals. This reference may therefore depend on other factors relating to the subject, such as subject parameters including but not limited to the age, weight, sex, height, ethnicity of the subject, as well as information regarding any medical interventions. In this instance, the processing system 200 can use the subject parameters provided during step 510 above to allow a respective reference to be selected.

To achieve this, the processing system 200 typically accesses a normal population database table, which includes reference values obtained from different subjects. This database table is essentially a single subject database table into which all measurements of normal population subjects are added. This table then acts as a pool of data from which normalised values for bone density and ash weight, as well as raw impedance data and ratios of impedance data can be generated, allowing comparison with measured values for the subject S to be performed.

The reference is then generated by selecting reference values that are relevant to the test subject. The selection is performed based on the subject parameters such as age, sex, height, weight, race, interventions, or the like.

Therefore if the test subject has unilateral lymphoedema of the dominant arm and is female then the normalised data drawn from the normal population database will be calculated from the dominant arm measurements from female subjects that are present in the in the normal population database.

Alternatively, or additionally, a longitudinal analysis is performed, in which determined biological indicators determined for the subject S are compared to a previously determined values for the indicators to determine if there has been a change in body composition or fluid levels, indicating lymphodema.

This is generally achieved by ensuring measurements taken prior to surgery or events that put them at risk of developing lymphoedema. A common example is baseline measurements taken before surgical intervention for breast cancer that can be use to track subjects fluid shifts post surgery by comparison of study measurements to these baseline generated mean values.

Whole Body Body Composition

In the case of performing body composition analysis for the entire subject S, the derived values of $R_0$ and $R_\infty$ are used to determined the total body water for the subject. This can be achieved using equations formulated from Hanai's theory. In particular, this indicates that the total body water is given by:

$$TBW = ecf + icf \quad (3)$$

where: TBW=total body water
ecf=volume of extracellular fluid
icf=volume of intracellular fluid In this regard, the volumes of extracellular and intracellular water can be derived from the values $R_0$, $R_\infty$, as these depend on the values of the extracellular and intracellular resistance, as discussed above.

An example of the process for determining ecf based on the method of Van Loan et al ("*Use of bioelectrical impedance spectroscopy (BIS) to measure fluid changes during pregnancy*"—*J. Appl Physiol.* 78:1037-1042, 1995), modified to take into account body proportion using the formulae of De Lorenzo et al ("*Predicting body cell mass with bioimpedance by using theoretical methods: a technological review*".—*J. Appl. Physiol.* 82(5): 1542-1558, 1997).

In particular, the extracellular fluid is given by:

$$ecf = \frac{\sqrt[3]{\frac{p^2 \rho_{ecw}^2}{d}} \sqrt[3]{\frac{h^4 w}{R_0^2}}}{100} \quad (4)$$

where: h=subject's height
p=subject's body proportion,
d=subject's body density,
$\rho_e$=subject's extracellular resistivity (sex dependent)

$$\rho_{ecw} = \sqrt[3]{\rho_e^2 d}$$

The icf is then given by:

$$\left(1 + \frac{icf}{ecf}\right)^{\frac{5}{2}} = \left(\frac{R_e + R_i}{R}\right)\left(1 + \frac{\rho_i}{\rho_e}\frac{icf}{ecf}\right) \quad (5)$$

where: $\rho_i$=subject's intracellular resistivity

This can be solved by expanding into the form shown in equation (6) and solving iteratively by using various values of x between 0 and 5, until the result is approximately zero (within 0.00001).

$$x^5 + 5x^4 + 10x^3 + \left(10 - \left(\frac{R_0}{R_\infty}\right)^2 \left(\frac{\rho_i}{\rho_e}\right)^2\right)x^2 + \left(5 - 2\left(\frac{R_0}{R_\infty}\right)^2 \left(\frac{\rho_i}{\rho_e}\right)\right)x + 1 - \left(\frac{R_0}{R_\infty}\right)^2 = 0 \quad (6)$$

where:

$$x = \frac{icf}{efc}$$

The icf can then be calculated from x and ecf determined using (4) above, with these being used by the processing system 200 to derive a five or six compartment model of body composition.

Segmental Body Composition

In addition to performing body composition for the entire body as described above, it is also possible to produce a segmental body composition model. In this instance, the composition of different segments of the subject are considered independently.

The procedure typically involves calculating the total and hence, intracellular and extracellular fluid levels for respective body segments, such as the subject's limbs, or half limbs. Once this is complete, a bone density or ash weight is calculated for each limb, before using the limb lengths and derived fluid levels to allow the body composition of each limb to be determined.

Additional details regarding the calculation of segmental body composition models can be found in "*Segment-Specific Resistivity Improves Body Fluid Volume Estimates from Bioimpedance Spectroscopy in Hemodialysis Patients*" by F. Zhu et al, J Appl Physiol (Oct. 27 2005).

Lymphodema Detection

In the case of lymphodema detection, the process used will depend on whether references are available. In particular, if no reference is available, it is typical for the processing system to determine an index for each of a number of different body segments, and then compare the determined indices to determine the presence, absence or degree of odema. However, if a reference is available, the index is typically compared to the reference to allow the presence, absence or degree of oedema to be determined.

Figure 10:
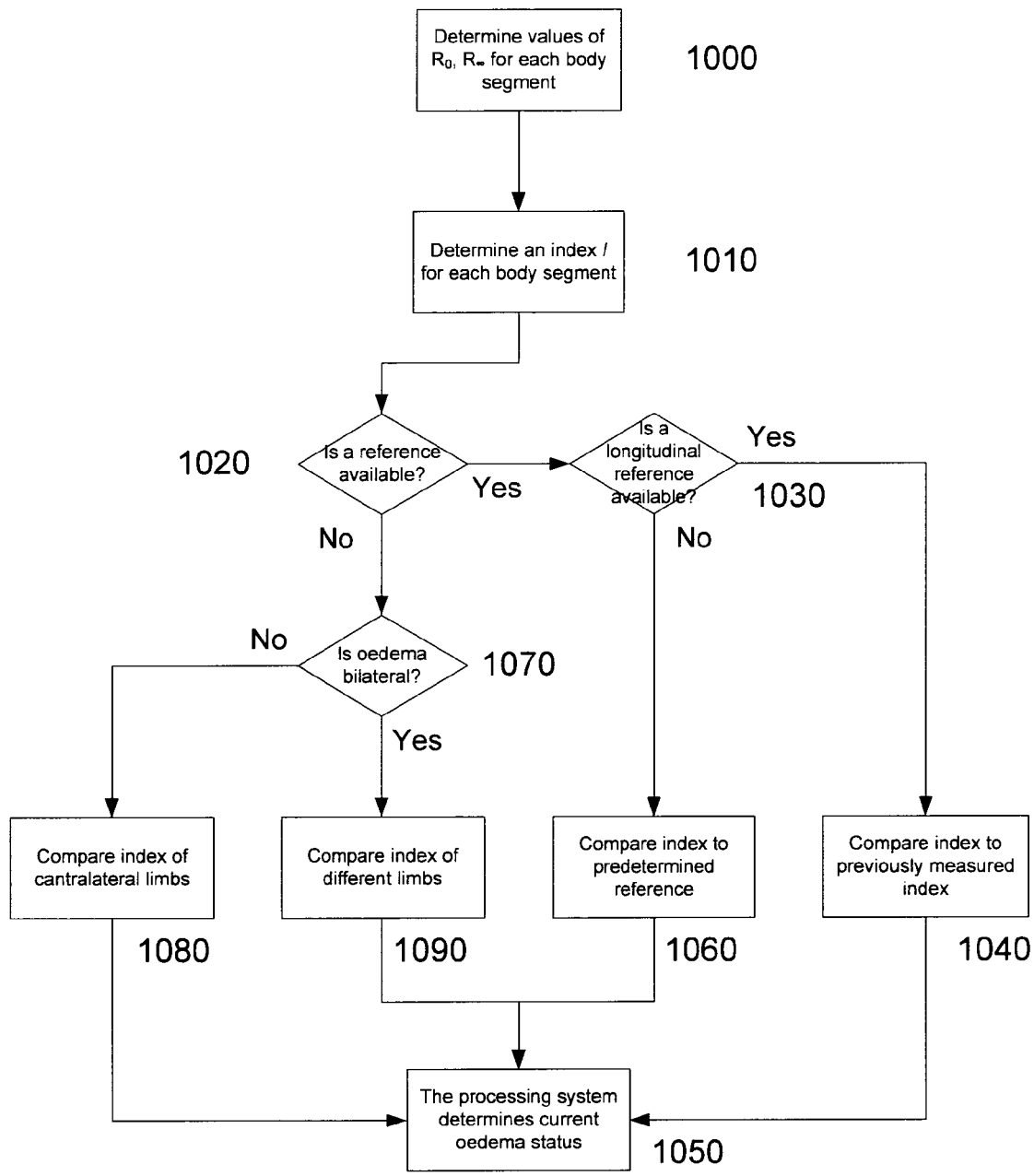
FIG. 10 is a flow chart of an example of the process of determining the presence, absence or degree of lymphodema.

An example of the process for measuring the presence, absence or degree of oedema will now be described with reference to FIG. 10.

In this example, at step 1000, impedance parameter values such as values for $R_0$ and $R_\infty$ are determined, with these values being used to determine an index I. In one example, the index I is given by a ratio of the intra to extra cellular fluid levels. The extracellular fluid resistance $R_e$ is determined from:

$$R_e = R_0$$

and intracellular fluid resistance $R_i$ is determined from:

$$R_i = \frac{R_\infty R_e}{R_e - R_\infty}$$

Thus, in one example, the index I, which is indicative of the ratio of extra- to intra-cellular fluid is given by the equation:

$$I = \frac{R_i}{R_e} = \frac{R_\infty}{R_0 - R_\infty} \quad (7)$$

However, alternatively, the index I can be based on any one or more of the impedance parameter values determined above, and could therefore be formed from either one of, or a combination of the parameter values $R_0$ and $R_\infty$.

As a further option, the index I may be based on a ratio of indices determined for different subject body segments. Thus, for example, the index I could be based on a ratio of indices for the subjects arm and legs, with the index I being given by:

$$I = \frac{I_{leg}}{I_{arm}} \quad (8)$$

The index I can be determined for each body segment, or only for body segments of interested, depending on the preferred implementation.

At step 1020, the processing system 200 determines if a reference is available. In general, comparison of the index I to a reference results in a more accurate lymphoedema detection, and hence is the preferred analysis technique. However, additionally, or alternatively, the index I derived for different body segments can be compared as will be described in more detail below. In any event, if a reference is available the process moves on to step 1030 to determine if the reference is a longitudinal reference.

A longitudinal reference, is a reference previously derived based on impedance measurements performed on the subject, and is therefore typically a previously determined value for the index I, referred to as a reference index $I_{prev}$. Preferably the reference is derived prior to the performance of any medical interventions or other events that may trigger the onset of oedema. Thus, for example, if the subject is to undergo surgery, a value for the index I can be determined in advance of performing the surgery, with subsequent changes in the value of index I being used to determine if lymphoedema is developing.

If a longitudinal reference is available, then at step 1040, the processing system 200 compares the index I to the previously measured index $I_{prev}$ utilising the change in index values to determine the presence, absence or degree of oedema.

In one example, this is achieved by comparing a ratio of the index and reference $I/I_{prev}$ to a predetermined range. Thus, it will be appreciated that if oedema is not present, then the index I and the reference index $I_{prev}$ should be substantially equal, in which case an index ratio $IR=I/I_{prev}$ should have a value substantially equal to one. By comparing the index ratio IR to a predetermined range this can be used to account for changes in fluid levels over time that may be caused by other factors, such as overall hydration levels.

In any event, if the index ratio IR falls outside the predetermined range, then this is used by the processing system 200 to determine the presence of oedema at step 650. Additionally, by assessing the value of the index ratio IR this can be used in assessing the degree of tissue oedema. Thus, for example, a number of value ranges can be defined, with each range corresponding to a different degree of oedema.

If it is determined that no longitudinal reference is available at step 1030, the processing system 200 moves on to step 1060 to compare the index I to a reference derived from sample populations, or the like. The reference can be selected based on the subject parameters, so that the value of the index I is compared to values of the index $I_{sample}$ derived from a study of a sample population of other individuals having similar subject parameters. Again, the comparison can be performed by determining an index ratio $IR=I/I_{sample}$ and comparing the index ratio IR to predetermined ranges. The result of the comparison can then be used to determine the presence, absence or degree of oedema at step 1050, in a manner similar to that described above with respect to the reference population.

In the event that no reference is available, for example because there are no similar nominal populations, or a longitudinal reference has not been generated, then the process moves on to step 1070 to determine if the oedema is bilateral.

In the event that the oedema is only unilateral, then at step 1080 the processing system 200 operates to compare the index I determined for contralateral limbs. Thus, for example, if oedema is suspected in the left arm, the index derived for the left arm $I_{leftarm}$ can be compared to the index derived for the right arm $I_{rightarm}$. In this instance, with similar limbs being used, similar index values should be obtained, and accordingly, an index ratio $IR=I_{leftarm}/I_{rightarm}$ should have a value of one. If the value differs by more than a predetermined amount, this indicates that oedema is likely, and accordingly, the index ratio can be compared to predetermined ranges to determine the presence, absence or degree of oedema, as described above.

In the event that the oedema is potentially bilateral, then it is not possible to compare indices derived for similar limbs, and accordingly indices of different limbs are compared at step 1090. Again this is typically achieved by generating an index ratio $IR=I_{arm}/I_{leg}$ and comparing the index ratio IR to threshold values to allow an indication of the presence, absence or degree of oedema to be determined at step 1050.

This is possible, as, for a healthy subject, there is generally a degree of similarity of intra- and extra-cellular fluid levels, even between different body segments. Thus, for example, if the subject is suffering from a condition other than oedema, which causes a general change in the ratio of extra- to intra-cellular fluid, then this should affect all body segments roughly equally. As a result, assuming that neither body segment has tissue oedema, then the index ratio IR should remain relatively constant for a given individual.

It will be appreciated that in the event that the properties of each body segment are equal, then the index ratio should have a value in the region of 1. Typically however, minor variations in tissue will occur between different body segments, and this can be accounted for in one of two ways.

In one example, the index ratio IR can be compared to a predetermined range that takes into account for variations between body segments that are not attributable to tissue oedema. It will therefore be appreciated that the range is therefore typically set to take into account the difference in index ratio IR between different body portions in a number of different subjects. This range can therefore be set based on data collected from a number of healthy subjects, previous analysis for the subject, or the like.

The value of the index ratio IR will also depend on the body segments that have been selected and accordingly, in general a different range will be selected for the comparison depending on the body segments under consideration.

The index ratio IR may also depend on a number of factors, such as the subject's age, weight, sex and height, and again a respective range can be selected based on these factors.

It will be appreciated from this, that the predetermined ranges to which the index ratio is compared may also be selected from references if available.

In one example, in addition to performing the above described analysis, the processing system 200 can also operate to determine limb volumes for each of the subject's limbs, from the radiation attenuation measurements, using this to attempt to detect the presence or absence of lymphodema. In general, the limb volume is related to level of fluid contained therein, and accordingly, the presence of lymphodema will typically result in differing limb sizes. However, this method of detection is not generally as sensitive as the impedance based method described above. Accordingly, if the processing system 200 detects using lymphodema using the impedance based method, but not using the volumetric analysis, this indicates that the lymphodema is at an early stage.

Such accurate detection of early stage lymphodema allows for more successful treatment, and in particular allows progression of the condition to be halted through the use of pressure bandages and message. This results in a vastly improved quality compared to subjects that progress to full stage lymphodema.

The above described system can also be used for visceral fat detection. In particular, the fluid levels within a subject can be used to determine an indication of the subject's subcutaneous fat mass. By combining this with a total fat mass derived from the radiation attenuation measurements, this allows a subject's visceral fat mass to be determined.

In the case of performing visceral fat detection, the impedance of body segments such as the limbs are of little interest. Accordingly, it is generally preferred to take impedance measurements relating to the subject's torso only. In one example, this can be achieved by using the electrode arrangements of FIG. 6A or 6B to obtain measurements for the entire body, and then subtracting impedance contributions due to the limbs, as derived using the electrode arrangements shown in FIGS. 6C and 6D.

However, the requirement to perform measurements on multiple body segments compounds any errors in the measurement process and hence reduces the accuracy. Additionally, in the event that the subject is suffering from lymphoedema, this can also further reduce the accuracy by impacting on the fluid levels measured for the limbs. Accordingly, it is typical to take specific impedance measurements of the subject's torso, which in one example can be performed using the electrode arrangement shown in FIGS. 11A to 11E.

Figure 11A:
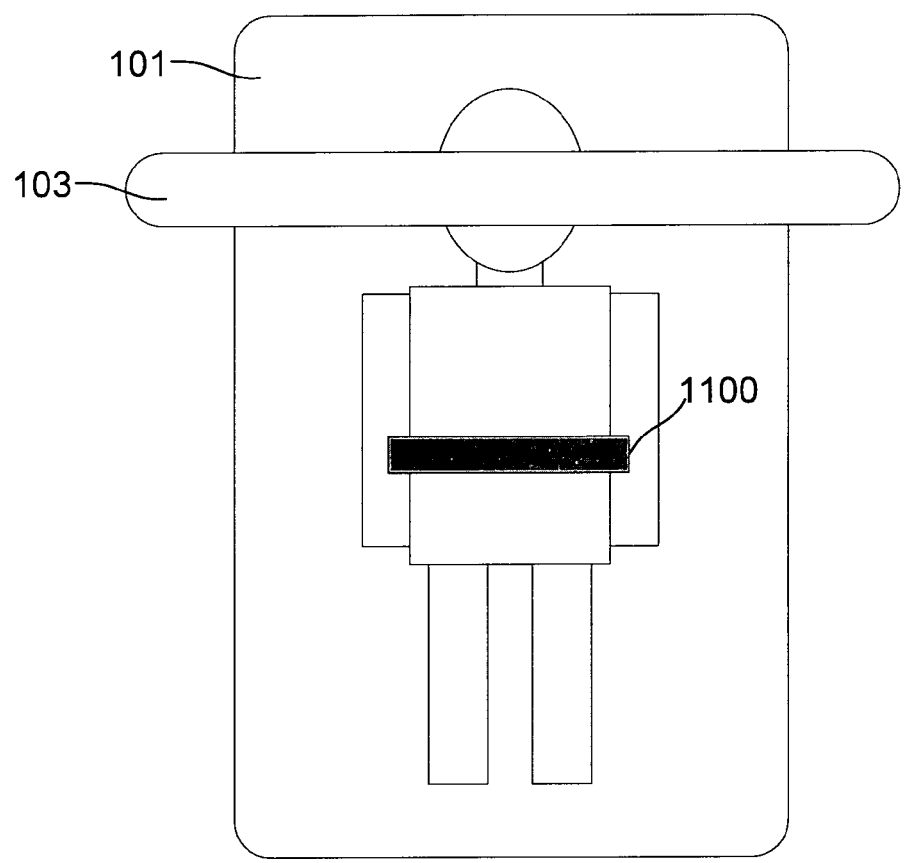
FIGS. 11A to 11G are schematic diagrams of an examples of an electrode arrangement used in detecting visceral fat levels.
Figure 11B:
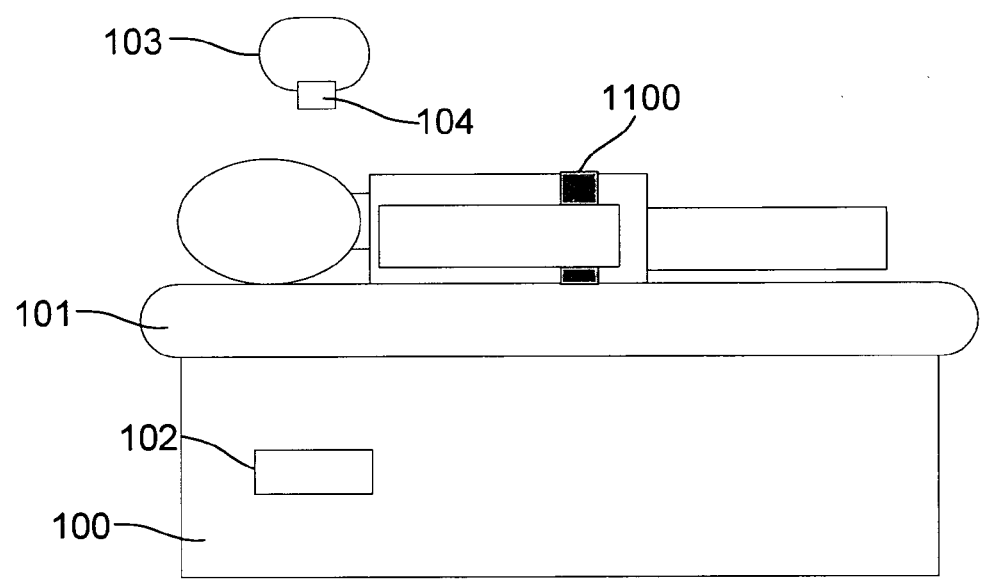
Figure 11C:
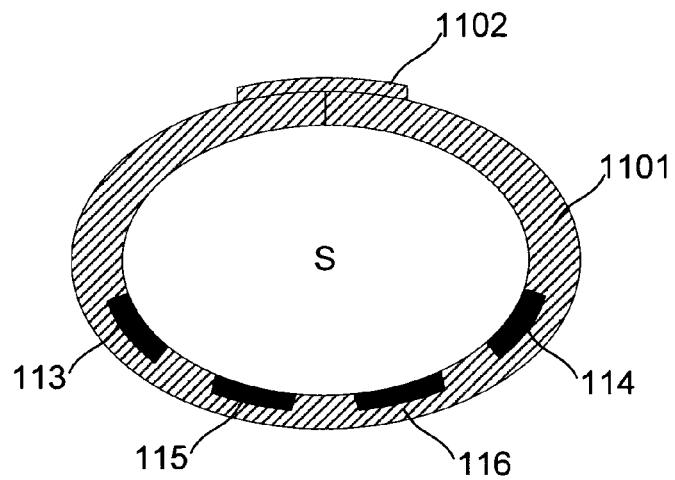

In this example, the apparatus includes a band electrode 1100 that is positioned around the subject's abdomen in use. The band electrode 1100 is generally formed from a substrate 1101 having metallic electrodes 113, 114, 115, 116 provided thereon. The band electrode 1100 typically includes a closing mechanism such as a velcro strip 1102, allowing the band to be held in place with the electrodes 113, 114, 115, 116 resting against the subject's abdomen, as shown in FIG. 11C. In order to ensure good electrical contact between the subject and the electrodes, conductive gel may be applied to the electrodes before use.

Whilst the band may be formed from a rigid material, generally the band is a flexible material allowing the band to be more easily attached to the subject, and allowing the band to be used with subjects having a different range of torso sizes. In a further example, the band substrate 1101 is formed from an inflatable member formed in a similar to a blood pressure cuff. In this example, the band is loosely attached to the subject using the velcro strap, before being inflated, with the inflation process urging the electrodes 113, 114, 115, 116 against the subject's abdomen, in turn helping to ensure good electrical contact.

In this example the electrodes 113, 114, 115, 116 may be connected to leads 213, 214, 215, 216, in any appropriate manner, as will be described for example in more detail below, thereby allowing impedance measurements to be performed.

In the example shown in FIG. 11C the band includes four electrodes, 113, 114, 115, 116, with the current electrodes 113, 114 positioned outwardly compared to the voltage sensing electrodes 115, 116. The electrodes 113, 114, 115, 116, are also generally spaced so as to be positioned across the front abdomen of the subject.

Figure 11D:
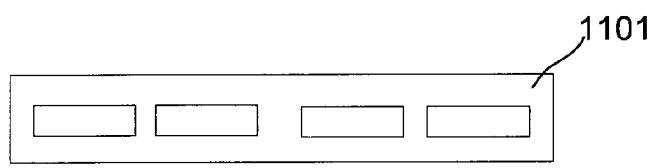
Figure 11E:
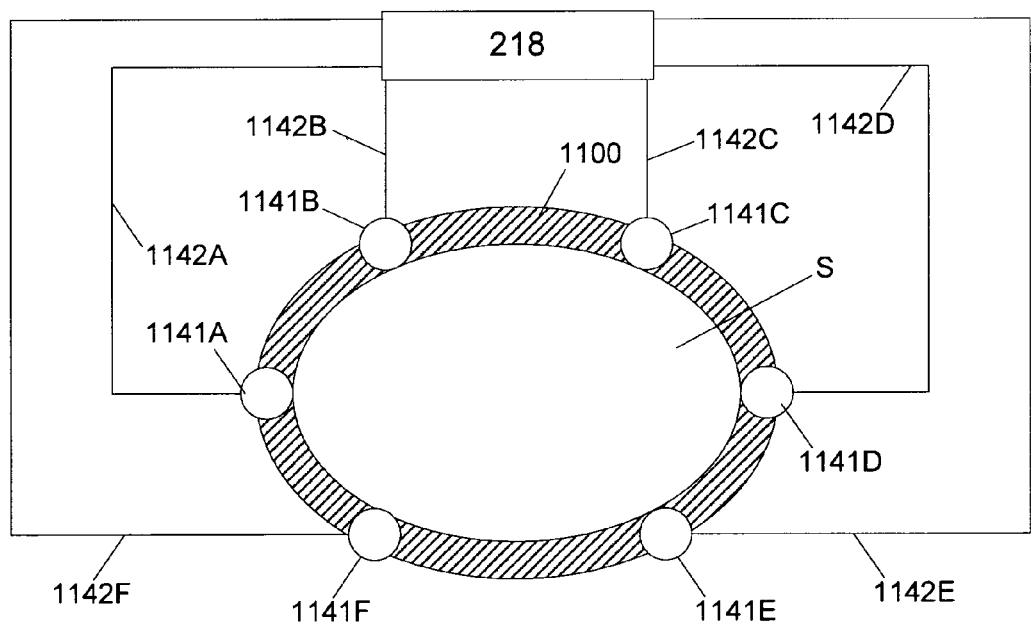
Figure 11F:
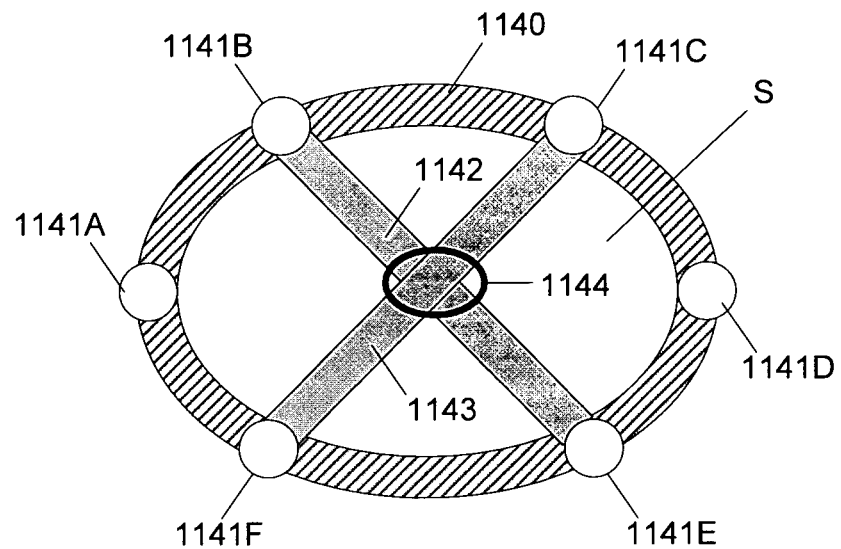

However, in an alternative example shown in FIG. 11F additional electrodes may be used, with the electrodes being spaced along the entire length of the substrate, such that the electrodes are spaced circumferentially around the subject S.

In this example, the band electrode includes a number of electrodes 1141A, . . . 1141F provided thereon, each of which may be used as a current or voltage electrode. To achieve this, the electrodes 1141A, . . . 1141F are connected to the switching device 218 via respective leads 1142A, . . . 1142F, allowing each of the electrodes 1141A, . . . 1141F to be selectively connected to the signal generator 111, and the sensor 112 as required. This in turn allows different segments of the subject's thoracic cavity to be measured.

Figure 11G:
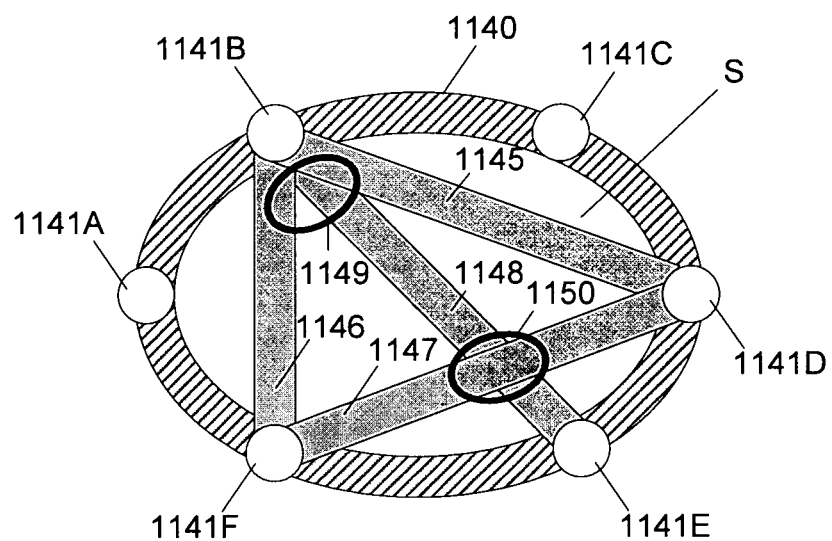

Thus, for example, in FIG. 11G, the current supply is applied to the electrodes 1141A, 1141D so that the electrodes 1141A, 1141D act as the current supply electrodes 113, 114. The induced voltage can then be measured using each of the other electrodes 1141C, 1141D, 1141E, 1141F, with the potentials being measured with respect to a common reference potential thereby allowing the potential measured at each electrode to be compared.

For the electrode configuration shown in FIG. 11G, it is apparent that the potentials generated at the electrodes 1141B, 1141F and similarly at the electrodes 1141C, 1141E will be identical, assuming a symmetrical impedance response for the subject's thoracic cavity. This allows comparison of the potentials between the electrodes, 1141C, 1141F, and between the electrodes 1141B, 1141E, as indicated at 1143, 1142 respectively.

By comparing the results of these comparisons, this allows the potential in a thoracic cavity segment 1144 to be determined, which in turn allows the processing system 200 to determine impedance values for the cavity segment 1144 at step 1530.

It will be appreciated that when alternative electrode configurations are used, as shown for example in FIG. 11H, this allows different potential comparisons to be performed, which in turn allows the impedance of different thoracic cavity segments to be performed. Thus, for example, in the configuration shown in FIG. 11H, the electrodes 1141A, 1141C are used as the current supply electrodes, with potentials being measured at the electrodes 1141B, 1141D, 1141E, 1141F. This allows potential differences between the electrodes 1141B, 1141D; 1141B, 1141F; 1141D, 1141F; 1141B, 1141E, to be determined, as shown at 1145; 1146; 1147; 1148, thereby allowing impedance values to be determined for the cavity segments 1149, 1150.

Accordingly, this technique can utilise each possible electrode configuration, in other words with each possible pair of the electrodes 1141A, ..., 1141F being used for current supply, allowing the impedance of a number of different cavity segments to be measured.

The measured impedance values are indicative of fat levels within the subject's abdomen, and include a component that is indicative of subcutaneous fat levels. In particular, because the abdominal subcutaneous fat layer thickness is strongly correlated with the abdominal electrical impedance, this results in a strong correlation between the measured impedance values and the level of subcutaneous fat. Accordingly, by performing a suitable analysis of the measured impedance values and/or impedance parameter values derived therefrom, this allows an indication of the levels of subcutaneous fat to be determined.

In addition to this, DEXA measurements can be utilised to provide an indication of total fat levels within the abdomen region. By combining this information with the indications of subcutaneous fat levels in the abdomen, this allows an indication of the subject's visceral fat levels to be derived.

Figure 12A:
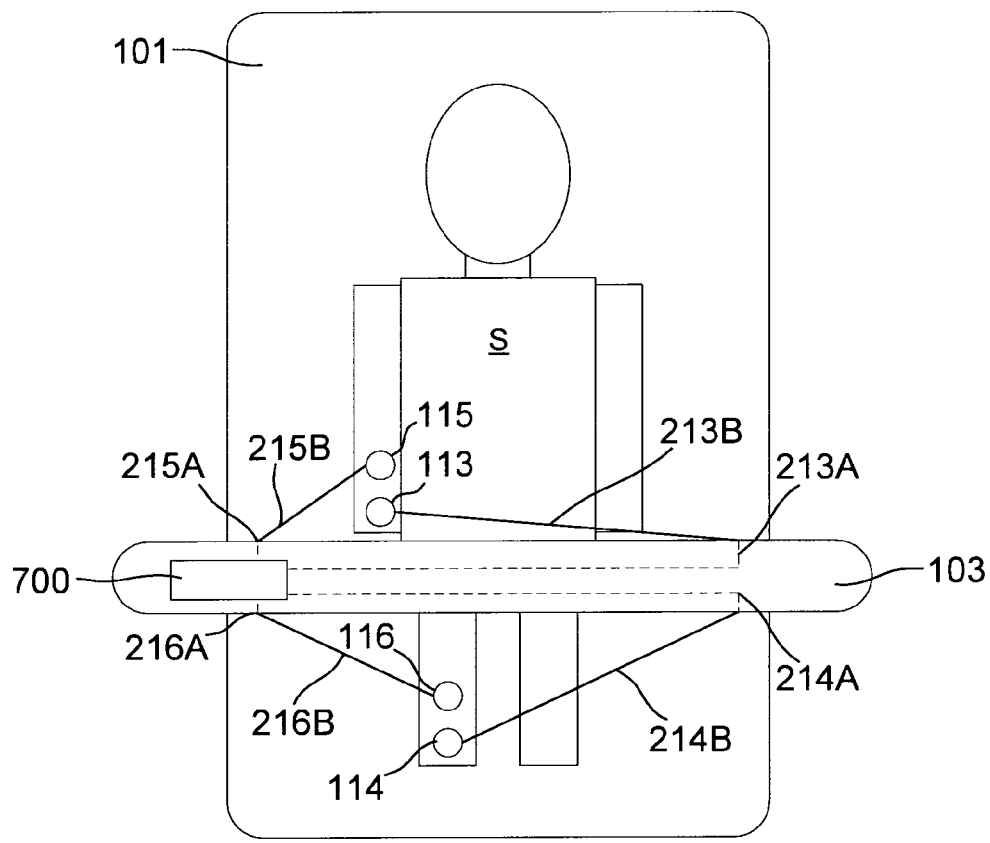
FIGS. 12A and 12B are schematic diagrams of plan and side views of a second example of a lead configuration for use in the apparatus of FIGS. 1A and 1B.
Figure 12B:
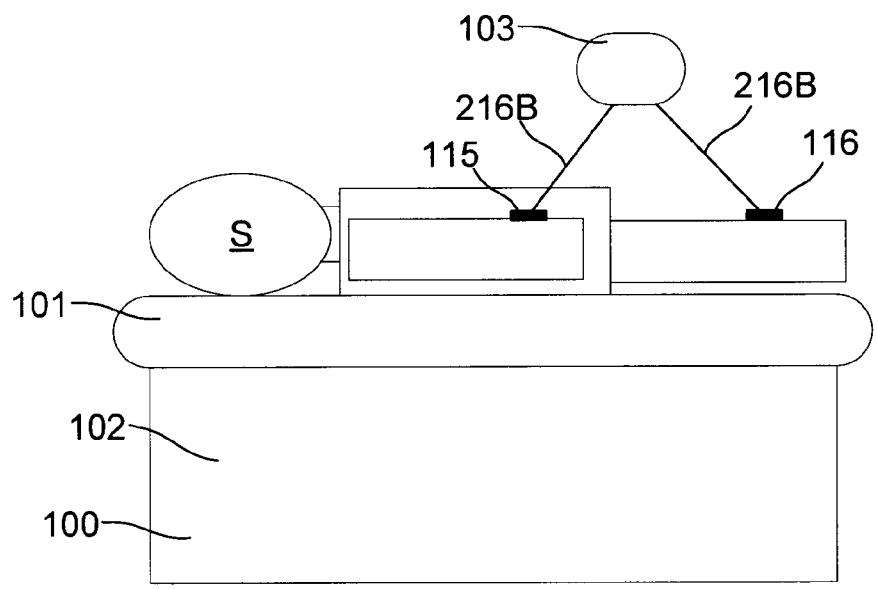

An alternative lead arrangement will now be described with reference to FIGS. 12A and 12B.

In this example, the embedded leads 213A, 214A, 215A, 216A are integrated into the arm 103, with the external leads 213B, 214B, 215B, 216B extending from respective locations in the arm, allowing them to be connected to the electrodes 113, 114, 115, 116, as shown. Again, in this example, the electrodes 113, 114 and the corresponding leads 213, 214 are omitted from FIG. 12B for clarity purposes.

In this example, it is typical for the leads to remain disconnected from the electrodes during the radiation attenuation measurement procedure. This has two main purposes. Firstly, if the leads were connected as the arm 103 moves along the length of the support surface 101, this would result in lead movement, which could effect both connections to the electrodes and lead integrity. Secondly, this allows the leads to be stored, for example by having the leads retracted into the arm 103. This allows the leads to be positioned so that they are not provided between the radiation source 102 and the detector 104, during the radiation attenuation measurement, thereby preventing the leads from interfering with the measurements.

A further issue that should be considered is that preferably the arm 103 should be consistently positioned between measurements on a given subject. In particular, the position of the arm 103 will have an impact on lead geometry, which as will be described in more detail below, can have an impact on errors induced by capacitive and inductive effects. Accordingly, ensuring that the arm 103 is positioned consistently, and in particular, is provided at the same position each time measurements are made on an individual, helps ensure that any errors are at least consistent between subsequent measurements. This in turn allows the errors to be accounted for, particularly when a longitudinal measurement procedure is performed.

An alternative electrode configuration will now be described with reference to FIGS. 13A to 13E.

In this example, the electrodes 114, 116 are integrated into a foot plate 1300. The foot plate is formed from an insulating substrate 1301, having metallic plates provided in the shape of a foot to form the electrodes 114, 116. In this example, the current electrode 114 is shaped to contact the ball of the subject's foot, whilst the voltage sensing electrode 114 is positioned to contact the heel, allowing the subject's foot to rest against the electrodes 114, 116 in use. The electrodes 114, 116 are connected to the connector 700, via the embedded leads 214A, 216A, in a manner similar to that described above with respect to FIGS. 7A and 7B.

Figure 13A:
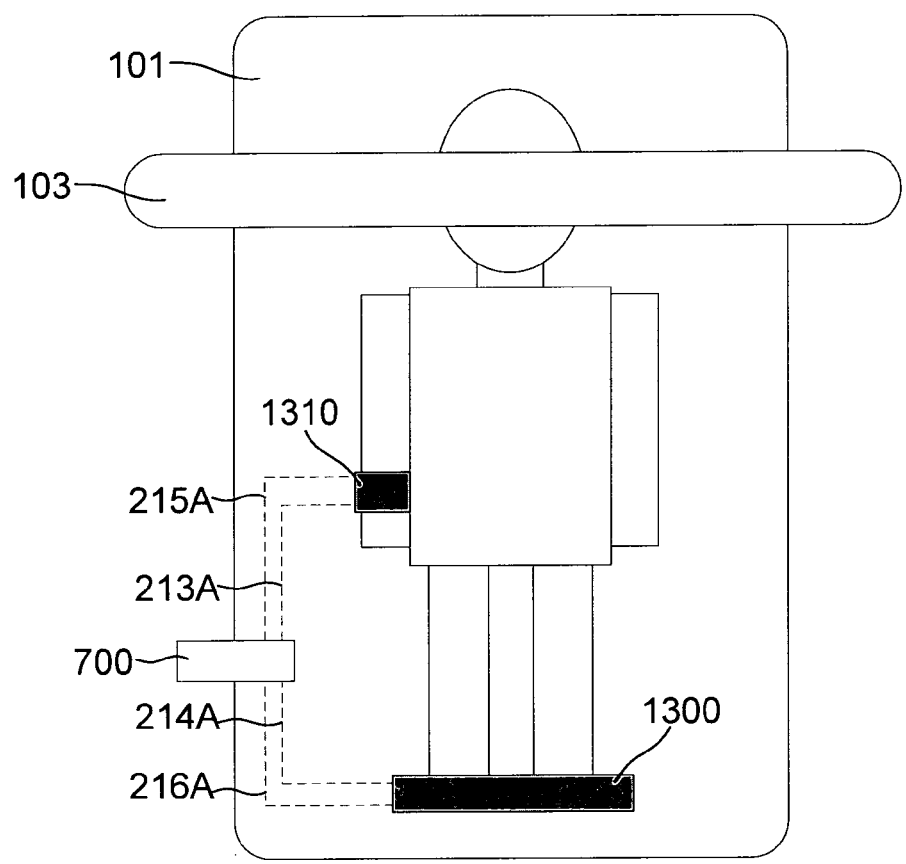
FIGS. 13A and 13B are schematic diagrams of plan and side views of an example of electrode configuration for use in the apparatus of FIGS. 1A and 1B.
Figure 13B:
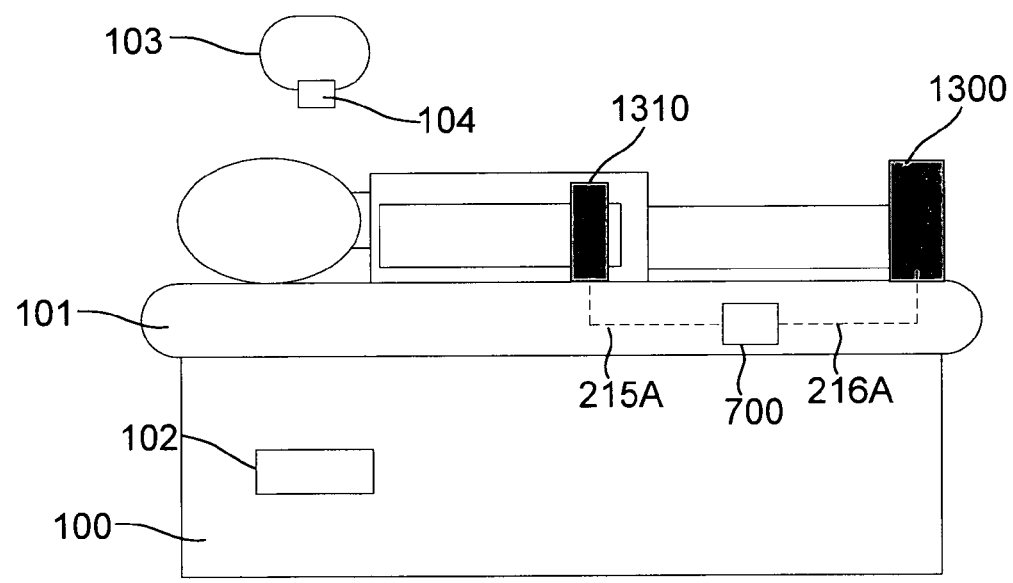

In one example, a respective set of electrodes 114, 116 in the form of shaped metal plates can be provided for each foot. In this example, each set of electrodes 114, 116, could be connected to a respective set leads 214A, 216A, (although only one such set is shown in FIG. 13A for clarity) allowing a number of different electrode configurations to be provided, as described for example in FIGS. 6A to 6D. Alternatively, a single set of electrodes may be provided corresponding to either the subject's left or right foot, depending on the preferred implementation.

In use, in order to ensure good electrical contact between the subject and the electrodes 114, 116, conductive gel may be applied to the electrodes 114, 116 before use.

Use of a foot plate 1300 in this manner has a number of benefits. Firstly, it avoids having to attach electrodes to the subject. Secondly, the foot plate 1300 can act as a guide, ensuring that the subject is correctly positioned on the support surface 101, which can help ensure accuracy of measurements, particularly with the radiation attenuation measurement procedure.

In this example, the electrodes 113, 115 are integrated into a cuff 1110, shown in more detail in FIGS. 11D and 11E. The cuff 1310 is formed from an insulating substrate 1311, having metallic electrodes 113, 115 provided thereon. The cuff includes a closing means, such as a Velcro strip 1312, allowing the cuff to be held in place around a subject's wrist, with the underside of the wrist resting against the electrodes 113, 115 in use. In order to ensure good electrical contact between the subject and the electrodes 113, 115, conductive gel may be applied to the electrodes 113, 115 before use.

In one example, the cuff substrate is formed from a rigid material, in which case a hinge may be required to allow the cuff to be opened and positioned on the subject. Alternatively, as in the case of the current example, the substrate can be flexible, allowing the cuff to be more easily attached to the subject, and allowing the cuff to be used with subject having a range of different body and limb sizes. In a further example, the cuff substrate is formed from an inflatable member similar to that of a blood pressure cuff. In this example, the cuff can be loosely attached to the subject, for example, using the velcro strap, before being inflated. The process of subsequent inflation ensures that the electrodes 113, 115 are urged against the subject, which in turn helps ensure good electrical contact.

The electrodes are again connected to the connector 700, via the embedded leads 213A, 215A, in a manner similar to that described above with respect to FIGS. 7A and 7B. Whilst only a single cuff 1310 is shown in FIG. 13A, this is again for clarity purposes only, and a respective cuff may be provided for each wrist.

Use of a cuff 1310 in this manner has a number of benefits. Firstly, it avoids having to attach separate electrodes to the subject. Secondly, the cuff 1300 can act as a guide, ensuring that the subject is correctly positioned on the support surface 101, which can help ensure accuracy of measurements, particularly with the radiation attenuation measurement procedure. The cuff will also tend to encourage the subject to remain stationary during the radiation attenuation measurement procedure, thereby enhancing accuracy of the measurements.

It will be appreciated that cuffs similar to the cuffs 1310 could be used to attaching electrodes 114, 116 to the subject's ankle, instead of using the foot plate 1300. Similarly, the cuffs 1310 could be replaced by a hand plate, similar to the foot plate 1300 described above.

Figure 14A:
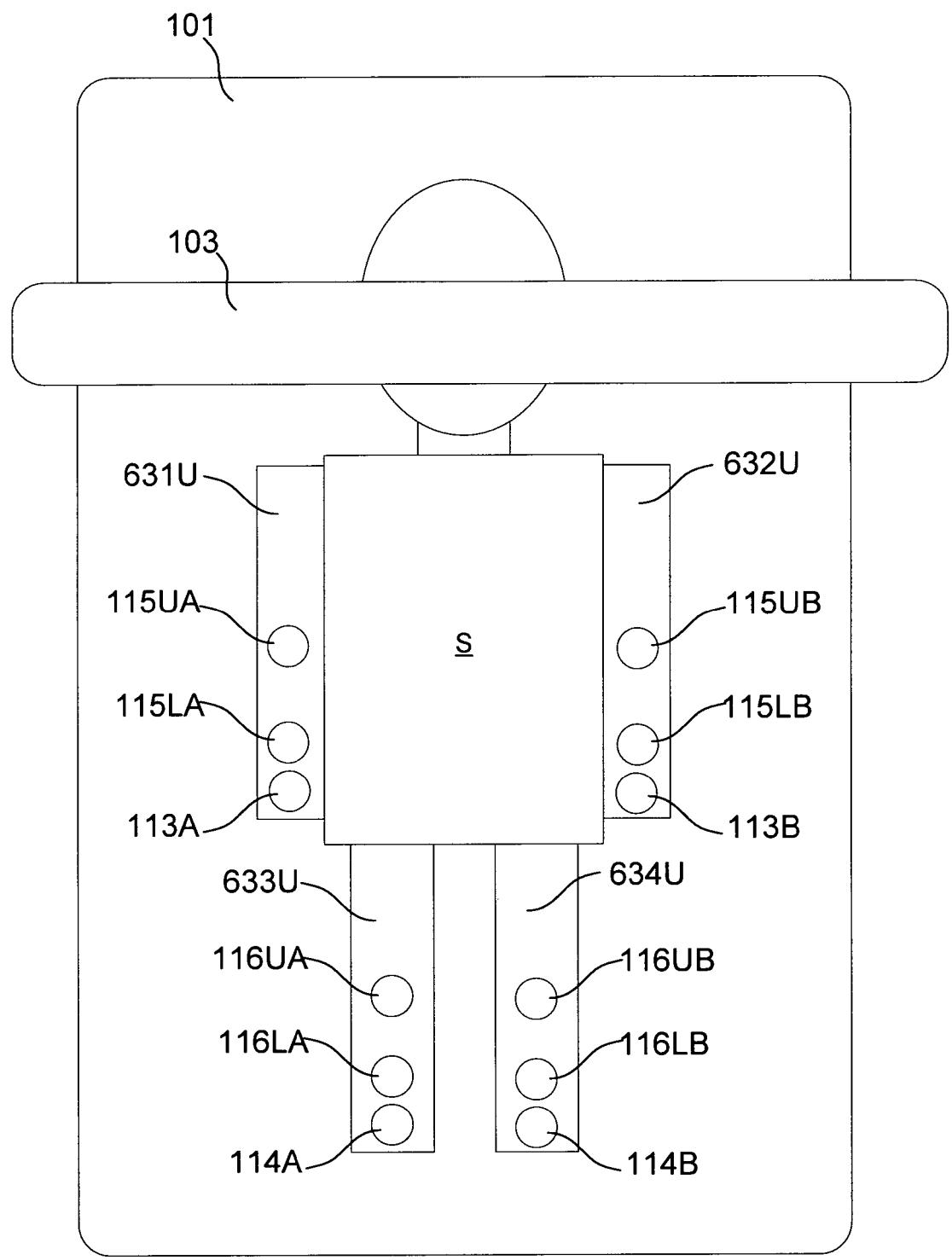
Figure 14B:
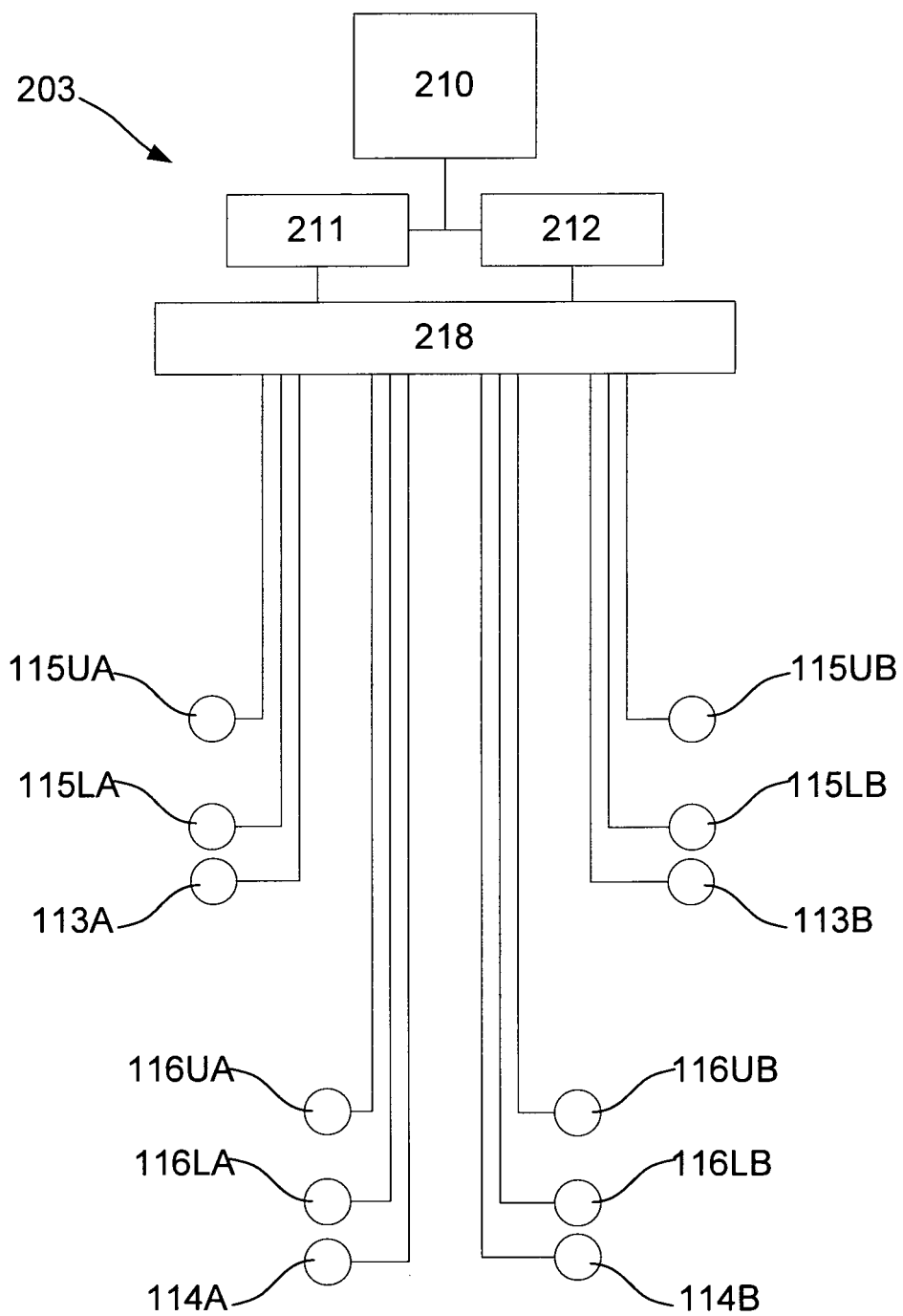

A further example electrode configuration and associated apparatus will now be described with reference to FIGS. 14A and 14B.

In this example, when the electrodes are initially connected to the subject, each of the electrodes required to perform the necessary impedance measurements are provided. In the example of FIG. 14A, electrodes are provided to allow for both half-limb and full limb segmental analysis to be performed, and this is therefore similar to the arrangement of FIG. 6E. In this example however, two sets of electrodes designated by the suffixes A and B are used to allow measurements to be performed for the subject's contralateral limbs.

Thus, in this example, the arm 631 includes a current electrode 113A, with a voltage measuring electrode 115LA provided on the wrist and a second voltage measuring electrode 115UA provided on the elbow. Similarly the arm 632 includes a current electrode 113B, with a voltage measuring electrode 115LB provided on the wrist and a second voltage measuring electrode 115UB provided on the elbow. The legs 633, 634 similarly include current electrodes 114A, 114B, with voltage measuring electrodes 116LA, 116LB on the ankles, and voltage measuring electrodes 116UA, 116UB positioned on the knees.

Each of these electrodes is attached to the measuring device 203, via a respective set of leads. These leads are not shown in FIG. 12A for clarity purposes, but it will be appreciated that the electrodes may be connected to the subject S via any of the lead arrangements described above.

In use, when the measuring device 293 is performing an impedance measuring procedure, the controller 201 will determine the body segments, such as limbs or half limbs, against which measurements are to be made. The controller 203 then uses the switching device 218 to selectively interconnect the current electrodes 113A, 113B, 114A, 114B to the signal generator 111 and the voltage sensing electrodes 115LA, 115UA, 115LB, 115UB, 116LA, 116LB, 116UA, 116UB to the sensor 112.

In this example, the measuring device 203 can include respective multiple leads allowing the respective electrodes used in the measurement procedure to be selected by suitable control of the switching device 218.

This allows the controller 210 to be used to select particular electrode configurations allowing different segments of the subject S to be measured in accordance with settings stored as part of the profiles. Accordingly, in use the operator can simply connect the electrodes as shown, and then allow the measurement process to be controlled by the controller 210, thereby ensuring all required measurements are collected correctly.

A further example of apparatus for analysis of a subject's bioelectric impedance will now be described with reference to FIG. 15.

As shown the apparatus includes a measuring device 1500 including a processing system 1502, connected to one or more signal generators 1517A, 1517B, via respective first leads 1523A, 1523B, and to one or more sensors 1518A, 1518B, via respective second leads 1525A, 1525B. As in the example of FIG. 2, the connection may be via a switching device, such as a multiplexer, although this is not essential.

In use, the signal generators 1517A, 1517B are coupled to two first electrodes 1513A, 1513B, which therefore act as drive electrodes to allow signals to be applied to the subject S, whilst the one or more sensors 1518A, 1518B are coupled to the second electrodes 1515A, 1515B, which therefore act as sense electrodes.

The signal generators 1517A, 1517B and the sensors 1518A, 1518B may be provided at any position between the processing system 1502 and the electrodes 1513A, 1513B, 1515A, 1515B, and may therefore be integrated into the measuring device 1500. However, in one example, the signal generators 1517A, 1517B and the sensors 1518A, 1518B are integrated into an electrode system, or another unit provided near the subject S, with the leads 1523A, 1523B, 1525A, 1525B connecting the signal generators 1517A, 1517B and the sensors 1518A, 1518B to the processing system 1502.

It will be appreciated that the above described system is a two channel device, with each channel being designated by the suffixes A, B respectively. The use of a two channel device is for the purpose of example only, as will be described in more detail below.

An optional external interface 1502 can be used to couple the measuring device 1500, via wired, wireless or network connections, to one or more peripheral devices 1504, such as an external database or computer system, barcode scanner, or the like. The processing system 1502 will also typically include an I/O device 1505, which may be of any suitable form such as a touch screen, a keypad and display, or the like.

Figure 2:
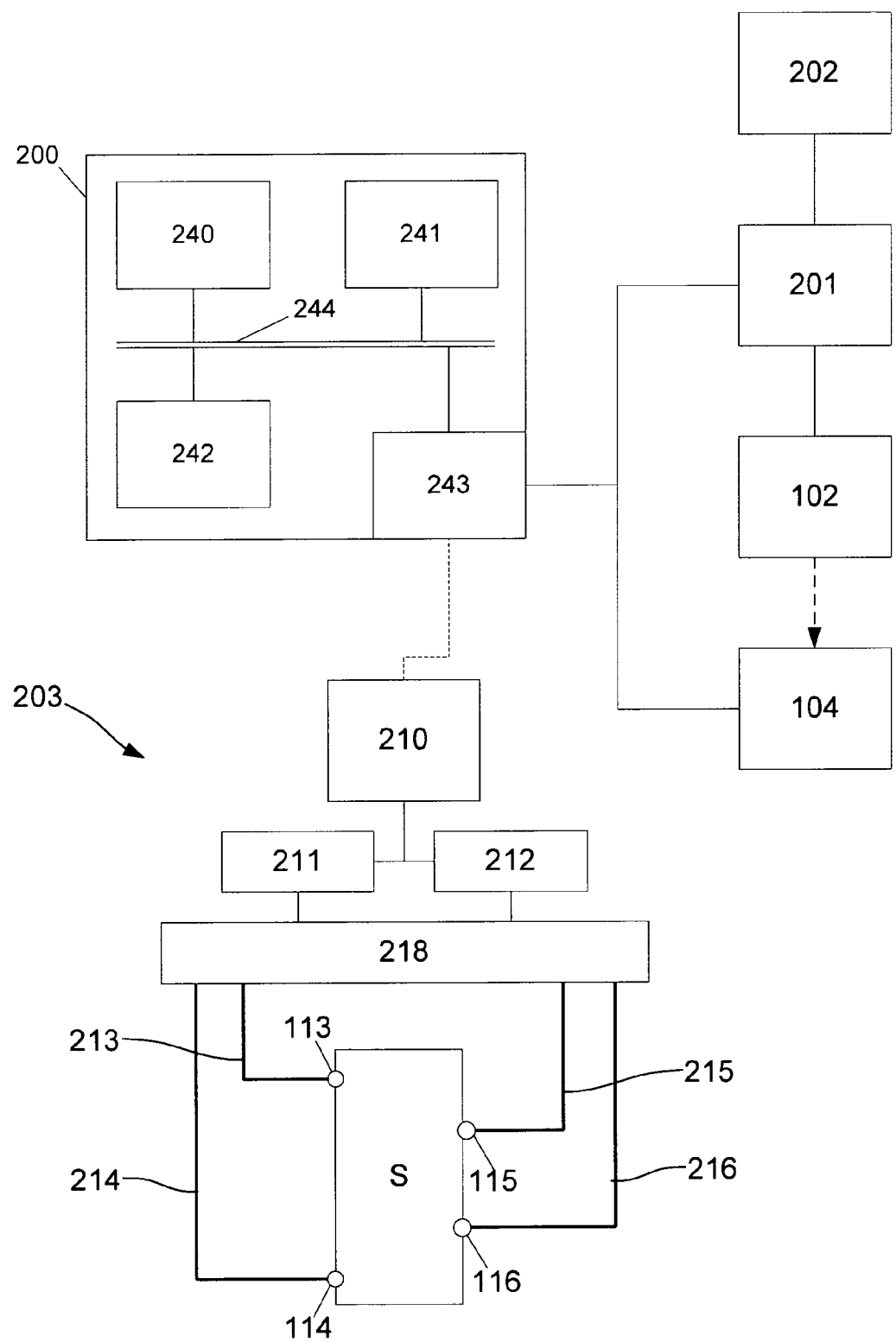
FIG. 2 is a schematic diagram of the control system of the apparatus of FIGS. 1A and 1B.

In use, the processing system 1502 functions in a similar manner to the controller 210 of FIG. 2, and is therefore adapted to generate control signals, which cause the signal generators 1517A, 15178 to generate one or more alternating signals, such as voltage or current signals of an appropriate waveform, which can be applied to a subject S, via the first electrodes 1513A, 1513B. The sensors 1518A, 1518B then determine the voltage across or current through the subject S, using the second electrodes 1515A, 1515B and transfer appropriate signals to the processing system 1502.

Accordingly, it will be appreciated that the processing system 1502 may be any form of processing system which is suitable for generating appropriate control signals and at least partially interpreting the measured signals to thereby determine the subject's bioelectrical impedance, and optionally determine other information such as the presence, absence or degree of oedema, or the like.

The processing system 1502 may therefore be a suitably programmed computer system, such as a laptop, desktop, PDA, smart phone or the like. Alternatively the processing system 1502 may be formed from specialised hardware, such as an FPGA (field programmable gate array), or a combination of a programmed computer system and specialised hardware, or the like, as will be described in more detail below.

In use, the first electrodes 1513A, 1513B are positioned on the subject to allow one or more signals to be injected into the subject S. The location of the first electrodes will depend on the segment of the subject S under study. Thus, for example, the first electrodes 1513A, 1513B can be placed on the thoracic and neck region of the subject S to allow the impedance of the chest cavity to be determined for use in cardiac function analysis. Alternatively, positioning electrodes on the wrist and ankles of a subject allows the impedance of limbs and/or the entire body to be determined, for use in oedema analysis, or the like.

Once the electrodes are positioned, one or more alternating signals are applied to the subject S, via the first leads 1523A, 1523B and the first electrodes 1513A, 1513B. The nature of the alternating signal will vary depending on the nature of the measuring device and the subsequent analysis being performed.

For example, the system can use Bioimpedance Analysis (BIA) in which a single low frequency signal is injected into the subject S, with the measured impedance being used directly in the assessment of oedema. In contrast Bioimpedance Spectroscopy (BIS) devices perform impedance measurements at multiple frequencies over a selected frequency range. Whilst any range of frequencies may be used, typically frequencies range from very low frequencies (4 kHz) to higher frequencies (15000 kHz). Similarly, whilst any number of measurements may be made, in one example the system can use 256 or more different frequencies within this range, to allow multiple impedance measurements to be made within this range.

Thus, the measuring device 1500 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically and/or differentially arranged, with each of the signal generators 1517A, 1517B being independently controllable, to allow the potential across the subject to be varied.

A potential difference and/or current is measured between the second electrodes 1515A, 1515B. In one example, the voltage is measured differentially, meaning that each sensor 1518A, 1518B is used to measure the potential at each second electrode 1515A, 1515B and therefore need only measure half of the potential as compared to a single ended system.

The acquired signal and the measured signal will be a superposition of potentials generated by the human body, such as the ECG (electrocardiogram), potentials generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as correlating the signal. This can be achieved by multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

In the case of BIS, impedance or admittance measurements are determined from the signals at each frequency by comparing the recorded voltage and the current through the subject. The demodulation algorithm can then produce an amplitude and phase signal at each frequency.

As part of the above described process, the distance between the second electrodes may be measured and recorded. Similarly, other parameters relating to the subject may be recorded, such as the height, weight, age, sex, health status, any interventions and the date and time on which they occurred. Other information, such as current medication, may also be recorded. This can then be used in performing further analysis of the impedance measurements, so as to allow determination of the presence, absence or degree of oedema, to assess body composition, or the like.

The accuracy of the measurement of impedance can be subject to a number of external factors. These can include, for example, the effect of capacitive coupling between the subject and the surrounding environment, as well as between the leads and the subject, which will vary based on factors such as lead construction, lead configuration, subject position, or the like. Additionally, there are typically variations in the impedance of the electrical connection between the electrode surface and the skin (known as the "electrode impedance"), which can depend on factors such as skin moisture levels, melatonin levels, or the like. A further source of error is the presence of inductive coupling between different electrical connections within the leads, or between the leads themselves.

Such external factors can lead to inaccuracies in the measurement process and subsequent analysis and accordingly, it is desirable to be able to reduce the impact of external factors on the measurement process.

As certain external factors, such as parasitic capacitances and inductive coupling, will affect the signals within each of the leads, it is preferable to perform the impedance measurements in such a way that the applied signal results in a symmetrical voltage about the sensing electrodes. The reason for this is that if the voltages sensed at the electrodes are unsymmetrical (a situation referred to as an "imbalance"), then differences in the magnitude of signals within the leads can lead to differing effects due to noise and interference.

For example, an imbalance will result in smaller voltage signals in one of the sets of leads, which can be more adversely effected by noise and other external effects. Thus, if this voltage is sufficiently small, it can be swamped by voltages arising due to inductive effects, or the like. Additionally, larger voltages in one of the leads can lead to larger parasitic capacitances and inductive coupling associated with that respective lead. These effects can therefore lead to a reduced accuracy for any resulting calculated impedance.

The presence of an imbalance, where the potential across the subject is not symmetrical with respect to the effective centre of the subject, leads to a "common mode" signal, which is effectively a measure of the signal at the subject that is unrelated to the subject's impedance.

To help reduce this effect, it is therefore desirable for signals to be applied to the subject so that they result in a symmetrical voltage about the sensing electrodes. This typically means that the reference voltage of the measurement apparatus will be close to the effective centre point of the subject, as considered relative to the electrode placement.

In one example, a symmetrical voltage about the sensing electrodes can be achieved by using a symmetrical voltage source, such as a differential bidirectional voltage drive scheme, which applies a symmetrical voltage to each of the drive electrodes 1513A, 1513B. However, this is not always effective if the electrode impedances for the two drive electrodes 1513A, 1513B are unmatched, which is typical in a practical environment.

In one example, the apparatus overcomes this by adjusting the differential drive voltages applied to each of the drive electrodes 1513A, 1513B, to compensate for the different electrode impedances, and thereby restore the desired symmetry of the voltage at the sense electrodes 1515A, 1515B. This process is referred to herein as balancing and in one example, helps reduce the magnitude of the common mode signal, and hence reduce current losses caused by parasitic capacitances associated with the subject.

The degree of imbalance, and hence the amount of balancing required, can be determined by monitoring the signals at the sense electrodes 1515A, 1515B, and then using these signals to control the signal applied to the subject via the drive electrodes 1513A, 1513B. In particular, the degree of imbalance can be calculated using the voltages detected at the sense electrodes 1515A, 1515B.

In one example, the voltages sensed at each of the sense electrodes 1515A, 1515B are used to calculate a first voltage, which is achieved by combining or adding the measured voltages. Thus, the first voltage can be an additive voltage (commonly referred to as a common mode voltage or signal) which can be determined using a differential amplifier.

In this regard, a differential amplifier is typically used to combine two sensed voltage signals $V_a$, $V_b$, to determine a second voltage, which in one example is a voltage differential $V_a - V_b$ across the points of interest on the subject, which is used in conjunction with a measurement of the current flow through the subject to derive impedance values. However, differential amplifiers typically also provide a "common mode" signal $(V_a + V_b)/2$, which is a measure of the common mode voltage.

Whilst some differential amplifiers include a common mode rejection capability, this is generally of only finite effect and typically reduces in effectiveness at higher frequencies, so a large common mode signal will produce an error signal superimposed on the differential signal.

By determining the magnitude of the common mode signal, the applied voltages can then be adjusted, for example by adjusting the relative magnitude and/or phase of the applied signal, to thereby minimise the common mode signal and substantially eliminate any imbalance.

An example of the operation of the apparatus of FIG. 15 to perform this will now be described with reference to FIG. 16.

At step 1600, a signal is applied to the subject S, via the first electrodes 1513A, 1513B, with the voltage signals measured across the subject S being determined at step 1610. This will typically be achieved using the techniques outlined above.

At step 1620, any imbalance is determined by the processing system 1502 using the first voltage derived from the potentials measured at each of the second electrodes 1515A, 1515B, which in one example represents a common mode signal At step 1630, the measuring device 1500 optionally adjusts the signal applied to the subject S, so as to reduce the imbalance and hence the magnitude of any common mode signal. Thus, the signal applied at either one of the first electrodes 1513A, 1513B can be adjusted, for example by increasing or decreasing the relative signal magnitudes and/or altering the relative signal phases, so as to balance the signal within the subject and centralise the position of the reference potential within the subject, relative to the electrode positioning.

At step 1640, the measuring device can then determine the signal applied to the subject and the potentials measured at the electrodes 1513A, 1513B, thereby allowing an impedance to be determined at step 1650.

As the position of the reference is impedance dependent, then the position of the reference potential within the subject, and hence the imbalance will typically vary depending on the frequency of the applied signal. Accordingly, in one example, it is typical to determine the imbalance and adjust the applied signal at each applied frequency. However, this may depend on the preferred implementation.

Figure 17:
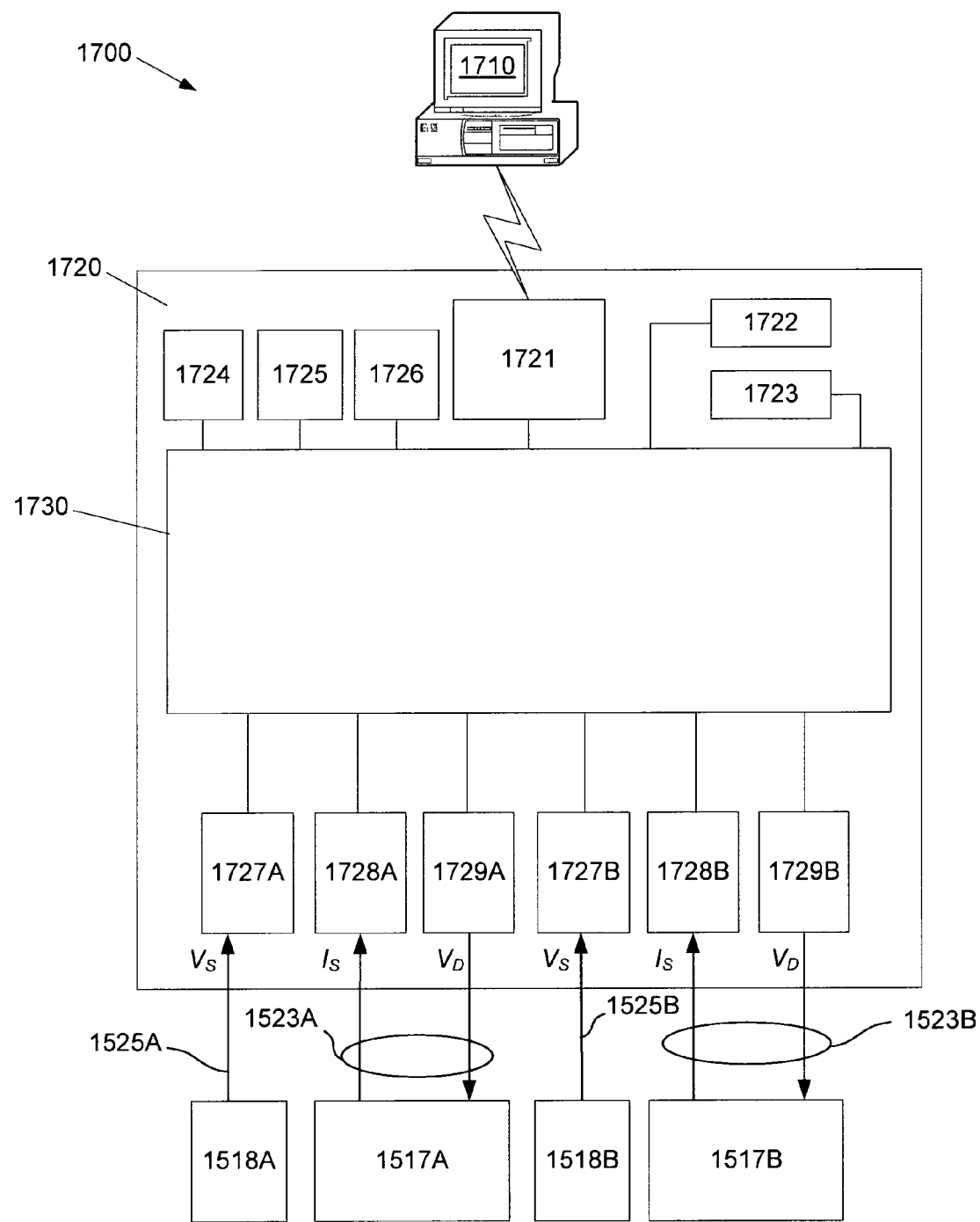
FIG. 17 is a schematic diagram of a second example of an impedance measuring device.

A specific example of the apparatus will now be described in more detail with respect to FIG. 17.

In this example, the measuring system 1700 includes a computer system 1710 and a separate measuring device 1720. The measuring device 1720 includes a processing system 1730 coupled to an interface 1721 for allowing wired or wireless communication with the computer system 1710. The processing system 1730 may also be optionally coupled to one or more stores, such as different types of memory, as shown at 1722, 1723, 1724, 1725, 1726.

In one example, the interface is a Bluetooth stack, although any suitable interface may be used. The memories can include a boot memory 1722, for storing information required by a boot-up process, and a programmable serial number memory 1723, that allows a device serial number to be programmed. The memory may also include a ROM (Read Only Memory) 1724, flash memory 1725 and EPROM (Electronically Programmable ROM) 1726, for use during operation. These may be used for example to store software instructions and to store data during processing, as will be appreciated by persons skilled in the art.

A number of analogue to digital converters (ADCs) 1727A, 1727B, 1728A, 1728B and digital to analogue converters (DACs) 1729A, 1729B are provided for coupling the processing system 1730 to the sensors 1518A, 1518B and the signal generators 1517A, 1517B, as will be described in more detail below.

A controller, such as a microprocessor, microcontroller or programmable logic device, may also be provided to control activation of the processing system 1730, although more typically this is performed by software commands executed by the processing system 1730.

Figure 18:
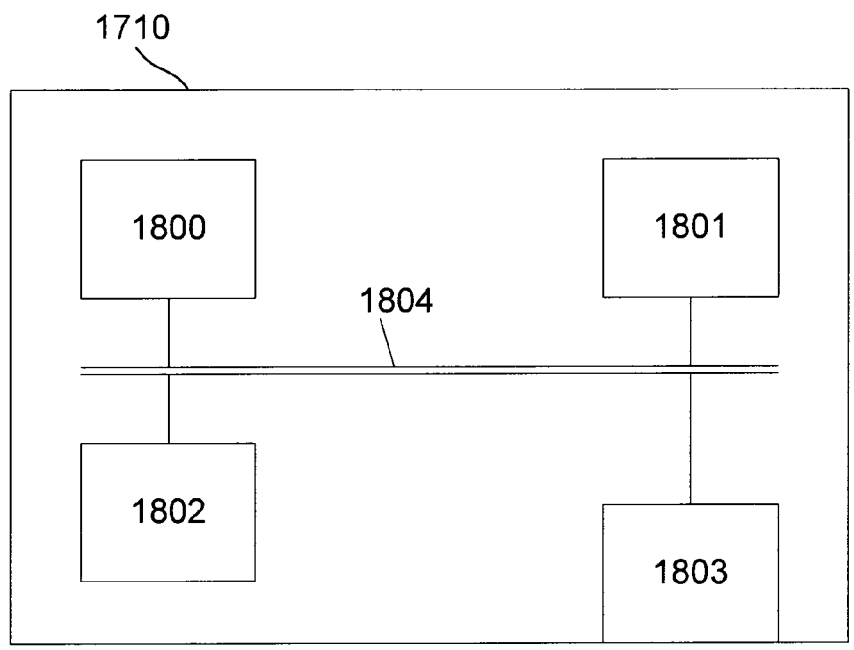
FIG. 18 is a schematic diagram of an example of a computer system.

An example of the computer system 1710 is shown in FIG. 18. In this example, the computer system 1710 includes a processor 1800, a memory 1801, an input/output device 1802 such as a keyboard and display, and an external interface 1803 coupled together via a bus 1804, as shown. The external interface 1803 can be used to allow the computer system to communicate with the measuring device 1720, via wired or wireless connections, as required, and accordingly, this may be in the form of a network interface card, Bluetooth stack, or the like.

In use, the computer system 1710 can be used to control the operation of the measuring device 1720, although this may alternatively be achieved by a separate interface provided on the measuring device 1700. Additionally, the computer system can be used to allow at least part of the analysis of the impedance measurements to be performed.

Accordingly, the computer system 1710 may be formed from any suitable processing system, such as a suitably programmed PC, Internet terminal, lap-top, hand-held PC, smart phone, PDA, server, or the like, implementing appropriate applications software to allow required tasks to be performed.

In contrast, the processing system 1730 typically performs specific processing tasks, to thereby reduce processing requirements on the computer system 1710. Thus, the processing system typically executes instructions to allow control signals to be generated for controlling the signal generators 1517A, 1517B, as well as the processing to determine instantaneous impedance values.

In one example, the processing system 1730 is formed from custom hardware, or the like, such as a Field Programmable Gate Array (FPGA), although any suitable processing module, such as a magnetologic module, may be used.

In one example, the processing system 1730 includes programmable hardware, the operation of which is controlled using instructions in the form of embedded software instructions. The use of programmable hardware allows different signals to be applied to the subject S, and allows different analysis to be performed by the measuring device 1720. Thus, for example, different embedded software would be utilised if the signal is to be used to analyse the impedance at a number of frequencies simultaneously as compared to the use of signals applied at different frequencies sequentially.

The embedded software instructions used can be downloaded from the computer system 1710. Alternatively, the instructions can be stored in memory such as the flash memory 1725 allowing the instructions used to be selected using either an input device provided on the measuring device 1720, or by using the computer system 1710. As a result, the computer system 1710 can be used to control the instructions, such as the embedded software, implemented by the processing system 1730, which in turn alters the operation of the processing system 1730.

Additionally, the computer system 1710 can operate to analyse impedance determined by the processing system 1730, to allow biological parameters to be determined.

Figure 4:
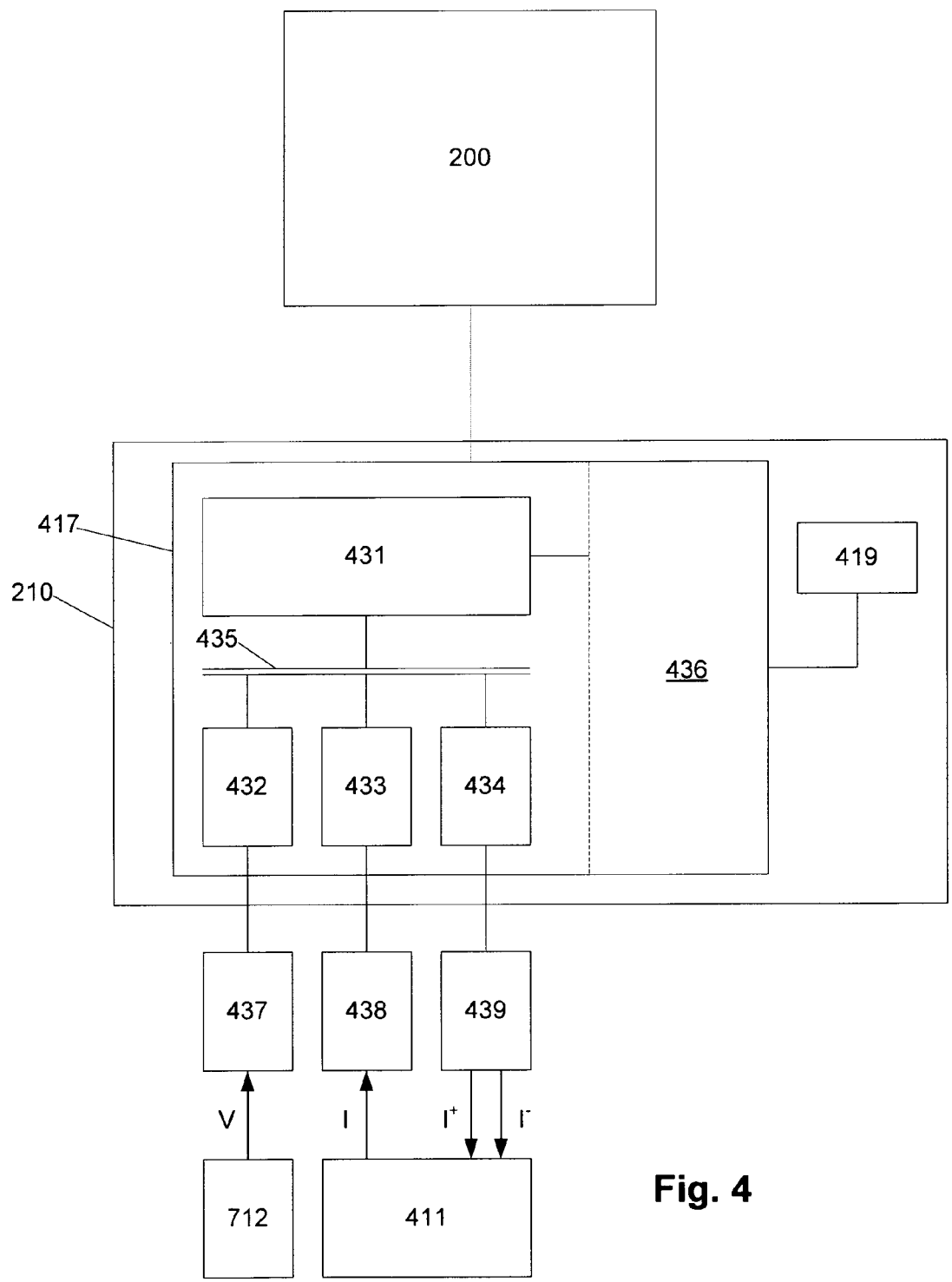
FIG. 4 is a schematic diagram of an example of the measuring device of FIG. 2.

As in the example of FIG. 4, whilst an alternative arrangement with a single processing system may be used, the division of processing between the computer system 1710 and the processing system 1730 can provide some benefits.

Firstly, the use of the processing system 1730 allows the custom hardware configuration to be adapted through the use of appropriate embedded software. This in turn allows a single measuring device to be used to perform a range of different types of analysis.

Secondly, this vastly reduces the processing requirements on the computer system 1710. This in turn allows the computer system 1710 to be implemented using relatively straightforward hardware, whilst still allowing the measuring device to perform sufficient analysis to provide interpretation of the impedance. This can include for example generating a "Wessel" plot, using the impedance values to determine parameters relating to cardiac function, as well as determining the presence or absence of lymphoedema.

Thirdly, this allows the measuring device 1720 to be updated. Thus for example, if an improved analysis algorithm is created, or an improved current sequence determined for a specific impedance measurement type, the measuring device can be updated by downloading new embedded software via flash memory 1725 or the external interface 1721.

In use, the processing system 1730 generates digital control signals, which are converted to analogue voltage drive signals $V_D$ by the DACs 1729, and transferred to the signal generators 1517. Analogue signals representing the current of the drive signal $I_D$ applied to the subject and the subject voltage $V_S$ measured at the second electrodes 1515A, 1515B, are received from the signal generators 1517 and the sensors 1518 and are digitised by the ADCs 1727, 1728. The digital signals can then be returned to the processing system 1730 for preliminary analysis.

In this example, a respective set of ADCs 1727, 1728, and DACs 1729 are used for each of two channels, as designated by the reference numeral suffixes A, B respectively. This allows each of the signal generators 1517A, 1517B to be controlled independently and for the sensors 1518A, 1518B to be used to detect signals from the electrodes 1515A, 1515B respectively. This therefore represents a two channel device, each channel being designated by the reference numerals A, B.

In practice, any number of suitable channels may be used, depending on the preferred implementation. Thus, for example, it may be desirable to use a four channel arrangement, in which four drive and four sense electrodes are provided, with a respective sense electrode and drive electrode pair being coupled to each limb. In this instance, it will be appreciated that an arrangement of eight ADCs 1727, 1728, and four DACs 1729 could be used, so each channel has respective ADCs 1727, 1728, and DACs 1729. Alternatively, other arrangements may be used, such as through the inclusion of a multiplexing system for selectively coupling a two-channel arrangement of ADCs 1727, 1728, and DACs 1729 to a four channel electrode arrangement, as will be appreciated by persons skilled in the art.

Figure 19:
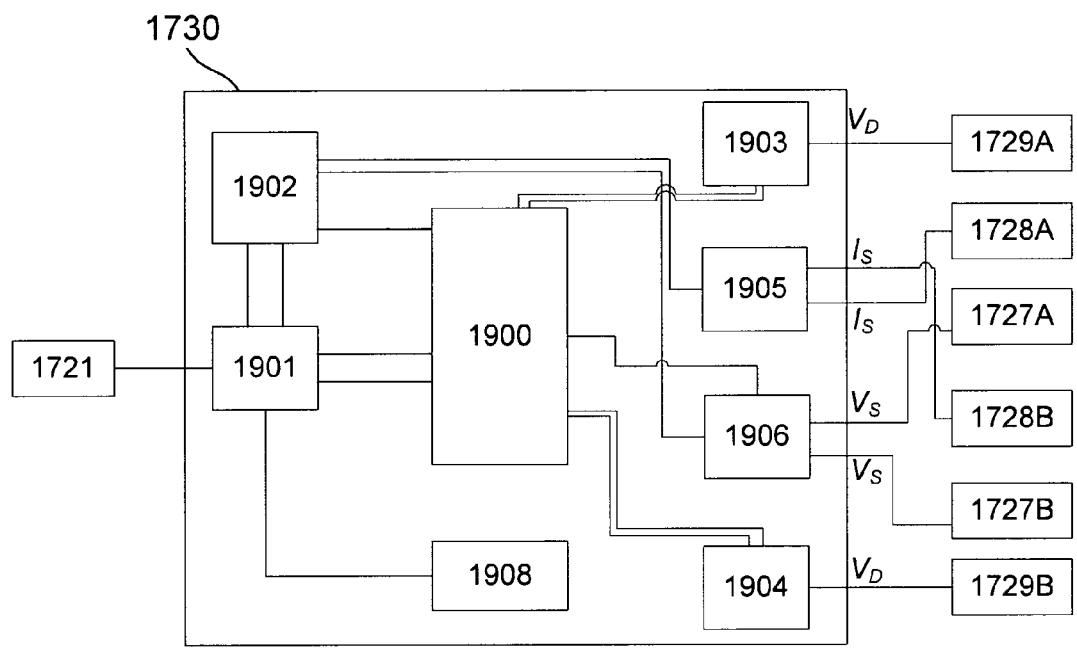
FIG. 19 is a schematic of an example of the functionality of the processing system of FIG. 17.

An example of the functionality implemented by the processing system 1730 will now be described with reference to FIG. 19. In this example the processing system 1730 implements the functionality using appropriate software control, although any suitable mechanism may be used.

In this example the processing system 1730 includes a timing and control module 1900, a messaging module 1901, an analysis module 1902, sine wave look up tables (LUTs) 1903, 1904, a current module 1905, and a voltage module 1906.

In use, the processing system 1730 receives information representing the frequency and amplitude of signals to be applied to the subject S from the computer system 1710, via the external interface 1721. The timing and control module 1900 uses this information to access the LUTs 1903, 1904, which in turn cause a digital sine wave signal to be produced based on the specified frequency and amplitude. The digital voltage signals are transferred to the DAC's 1729A, 1729B, to thereby allow analogue voltage drive signals $V_D$ to be produced.

Measured analogue voltage and current signals $V_S$, $I_S$ are digitised by the ADC's 1727, 1728 and provided to the current and voltage modules 1905, 1906. This allows the processing system 1730 to determine the current flow by having the current module 1905 determine the total current flow through the subject using the two current signals $I_S$, with an indication of this being provided to the analysis module 1902. The voltage module 1906, which is typically in the form of a differential voltage amplifier, or the like, operates to determine a differential voltage, which is also transferred to the analysis module 1902, allowing the analysis module to determine impedance values using the current and differential voltage signals.

In addition to this, the voltage module 1906 determines an common mode voltage (i.e. a common mode signal), which is returned to the timing and control module 1900. This allows the timing and control module 1900 to determine any imbalance in the voltage sensed at the subject, which as mentioned above is indicative of the device reference potential not being positioned centrally within the subject with respect to the electrodes.

If the degree of imbalance is unacceptable, the timing and control module 1900 can adjust the relative amplitude and/or phase of the sine waves representing the voltage drive signals $V_D$ as will be described below, allowing a new imbalance to be determined.

Once the imbalance is determined to be acceptable the timing and control module 1900 can provide an indication of this to the analysis module 1902, allowing this to use appropriate analysis, such as phase quadrature extraction, to determine a ratio and phase difference for the measured impedance, based on the current flow through the subject and the differential voltage signals. The ratio and phase can then be transferred to the messaging module 1910 allowing an indication of measured impedance to be provided to the computer system 1710 via the interface 1721.

The processing system 1730 may also implement a signal level fault detection module 1908. This monitors the magnitude of signals applied to the subject to determine if these are within acceptable threshold levels. If not, the fault detection module 1908 can cause a message to be transferred to the computer system 1710 to allow the process to be halted or to allow an alert to be generated.

Figure 20A:
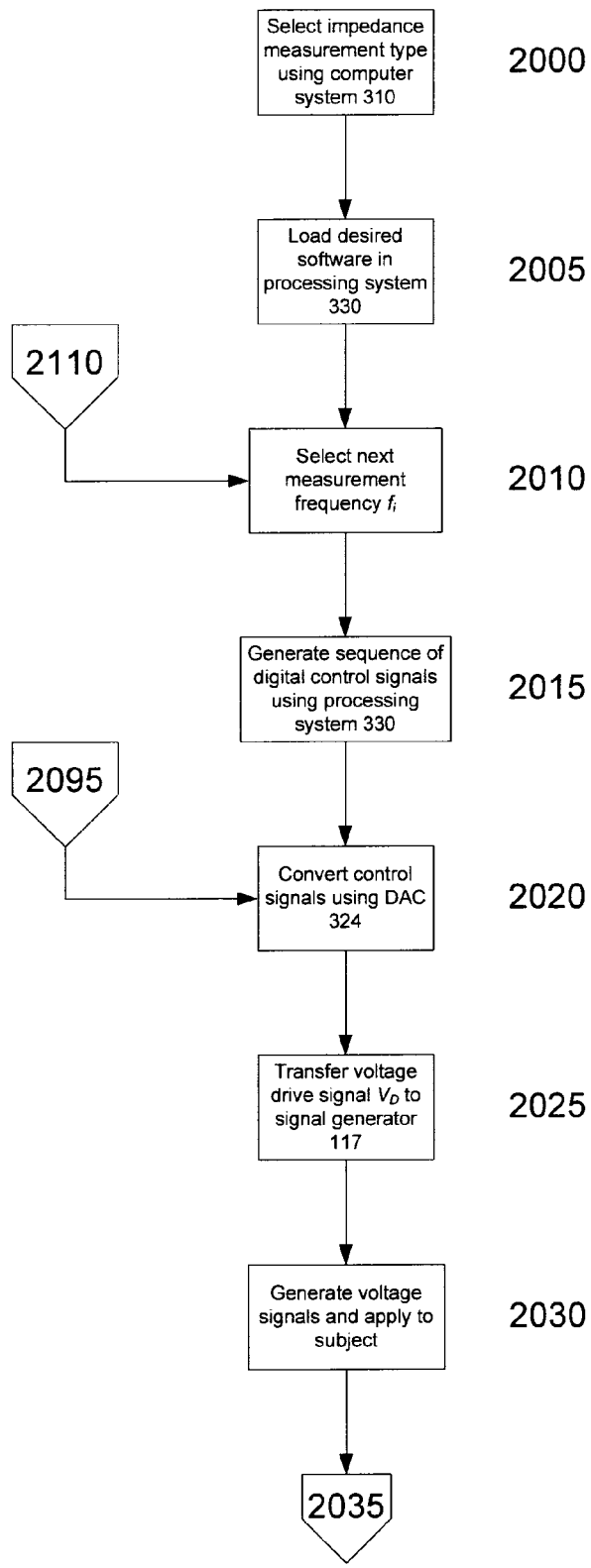
FIGS. 20A to 20C are a flowchart of a second example of a process for performing impedance measurements.
Figure 20B:
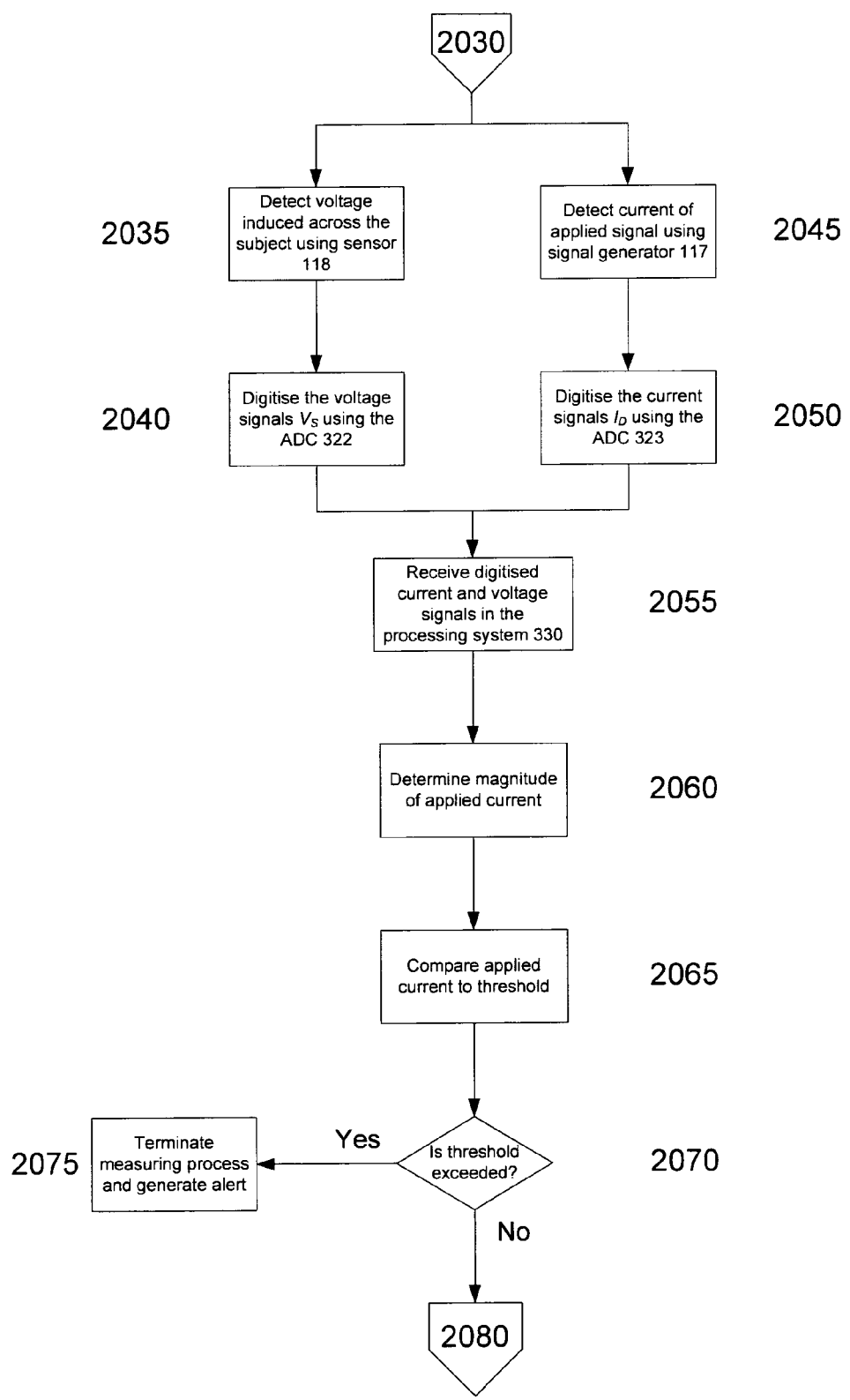
Figure 20C:
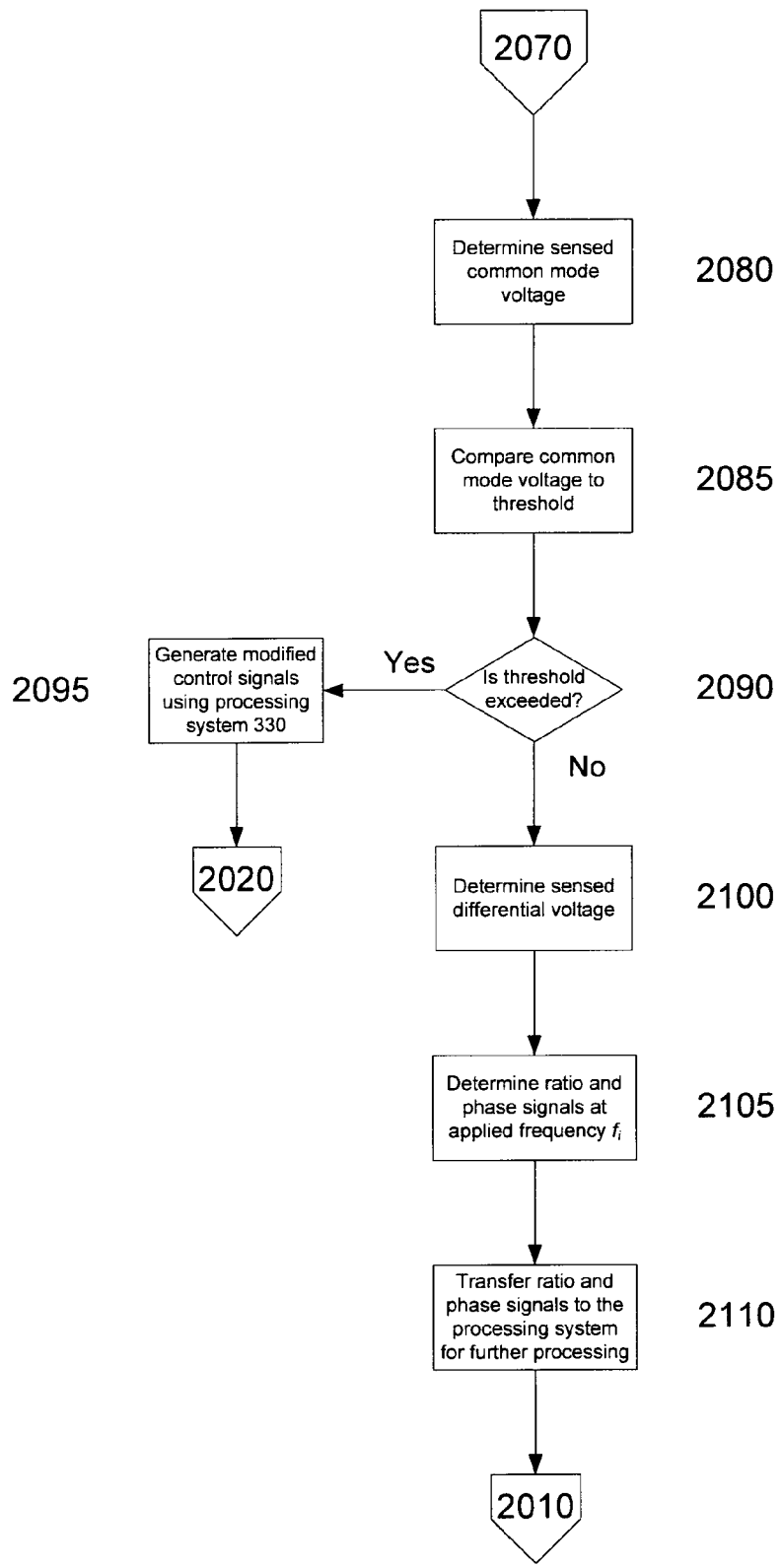

An example of the process for performing impedance measurements will now be described with reference to FIG. 20A to 20C.

At step 2000 the computer system 1710 is used to select an impedance measurement type, with this triggering the computer system 1710 to cause desired instructions, such as embedded software, to be implemented by the processing system 1730. It will be appreciated that this may be achieved in a number of manners, such as by downloading required embedded software from the computer system 1710 to the processing system 1730 or alternatively by having the processing system 1730 retrieve relevant embedded software from internal memory or the like.

At step 2010 the computer system 1710 or the processing system 1730 selects a next measurement frequency $f_i$, allowing the processing system 1730 to generate a sequence of digital voltage control signals at step 2015, as described above. The digital control signals are converted to analogue voltage signals $V_D$ using the DACs 1729A, 1729B at step 2020, allowing the analogue control signals to be provided to each of the voltage sources 1517A, 1517B at step 2025. At this point each voltage source 1517A, 1517B generates respective voltage signals and applies these to the subjects at step 2030, via the respective drive electrodes 1513A, 1513B.

At step 2035 the voltage induced across the subject is detected via the sense electrodes, 1515A, 1515B, using the sensors 1518A, 1518B, with the sensed voltage signals $V_S$ being digitised by the corresponding ADC 1727A, 1727B at step 2040. At step 2045, simultaneously with this, the current applied to the subject $I_S$, by way of application of the voltage signal, is measured using the signal generators 1517A, 1517B. An indication of the current injected into the subject $I_S$ is transferred to the ADCs 1728A, 1728B for digitisation at step 2050.

At step 2055 the digitised current and voltage signals $I_S$, $V_D$ are received by the processing system 1730 allowing the processing system 1730 to determine the magnitude of the applied current at step 2060. This may be performed using the current module 1905 in the above described functional example of FIG. 19, allowing the fault detection module 1908 to compare the total current flow through the subject to a threshold at step 2065. If it is determined that the threshold has been exceeded at step 2070 then the process may terminate with an alert being generated at step 2075.

This situation may arise, for example, if the device is functioning incorrectly, or there is a problem with connections of electrodes to the subject, such as if one is not in correct electrical contact with the subject's skin. Accordingly, the alert can be used to trigger a device operator to check the electrode connections and/or device operation to allow any problems to be overcome. It will be appreciated, that any suitable form of corrective action may be taken such as attempting to restart the measurement process, reducing the magnitude of the current through the subject, or the like.

At step 2080 the processing system 1730 operates to determine an common mode voltage based on the voltage potential sensed at each of the electrodes 1515A, 1515B, and this is typically achieved using the voltage processing module 1906 in the above functional example. The common mode voltage or common mode signal is then used to determine any imbalance at step 2085.

At step 2090 an assessment is made as to whether the imbalance is acceptable, and it will be appreciated that this may be achieved in any one of a number of ways, such as by comparing the amplitude of the common mode signal to a threshold, or the like. The threshold will generally be previously determined and stored in one of the memories 1724, 1725, 1726, for example during device manufacture or calibration.

In the event that the imbalance is deemed to not be acceptable, then at step 2095 the processing system 1730 modifies the digital control signals to reduce the imbalance. This is typically achieved by having the processing system 1730 implement an algorithm that adjusts the applied signal to maintain the common mode voltage at the centre of the body as close to the electronics reference or ground potential as possible. This is generally achieved by adjusting the amplitude and/or phase of the voltage signals applied to the subject, using the algorithm. The nature of this adjustment will depend on the nature of the imbalance, as will be appreciated by persons skilled in the art.

The process can then return to step 2020 to allow the modified control signals to be converted to analogue signals using DACs 1724, with a modified voltage signal being applied to one or each of the electrodes 1513A, 1513B. This process is repeated until an acceptable offset is achieved.

Once an acceptable balance is achieved, the processing system 1730 operates to determine the differential voltage sensed across the subject at step 2100. In the functional example described above with respect to FIG. 19, this can be achieved using the differential voltage module 1906.

At step 2105 the processing module 1730 operates to determine ratio and phase signals, representing the impedance of the subject S, at the applied frequency $f_i$ using the current and differential voltage signals. In the above functional example, this can be performed using the analysis module, and some form of signal analysis, such as phase quadrature analysis, depending on the preferred implementation. At step 2110, an indication of the ratio and phase signals are sent to the computer system 1710 for further processing.

Once this is completed the process may return to step 2010 to allow the process to be repeated at a next measurement frequency $f_i$ otherwise if all required frequencies are complete, the measurement process can terminate, allowing the computer system 1710 to analyse the impedance measurements, and determine required information, such as any biological indicators, impedance parameters, or the like. The manner in which this is achieved will depend on the type of analysis being performed.

Accordingly, it will be appreciated that by repeating the above described process this allows a number of impedance measurements to be performed over a range of different frequencies. Furthermore, prior to at least one, and more typically, to each measurement, a check can be performed to ensure that the common mode of the subject and the device are approximately matched, thereby reducing inaccuracies in the measurement procedure.

Figure 21:
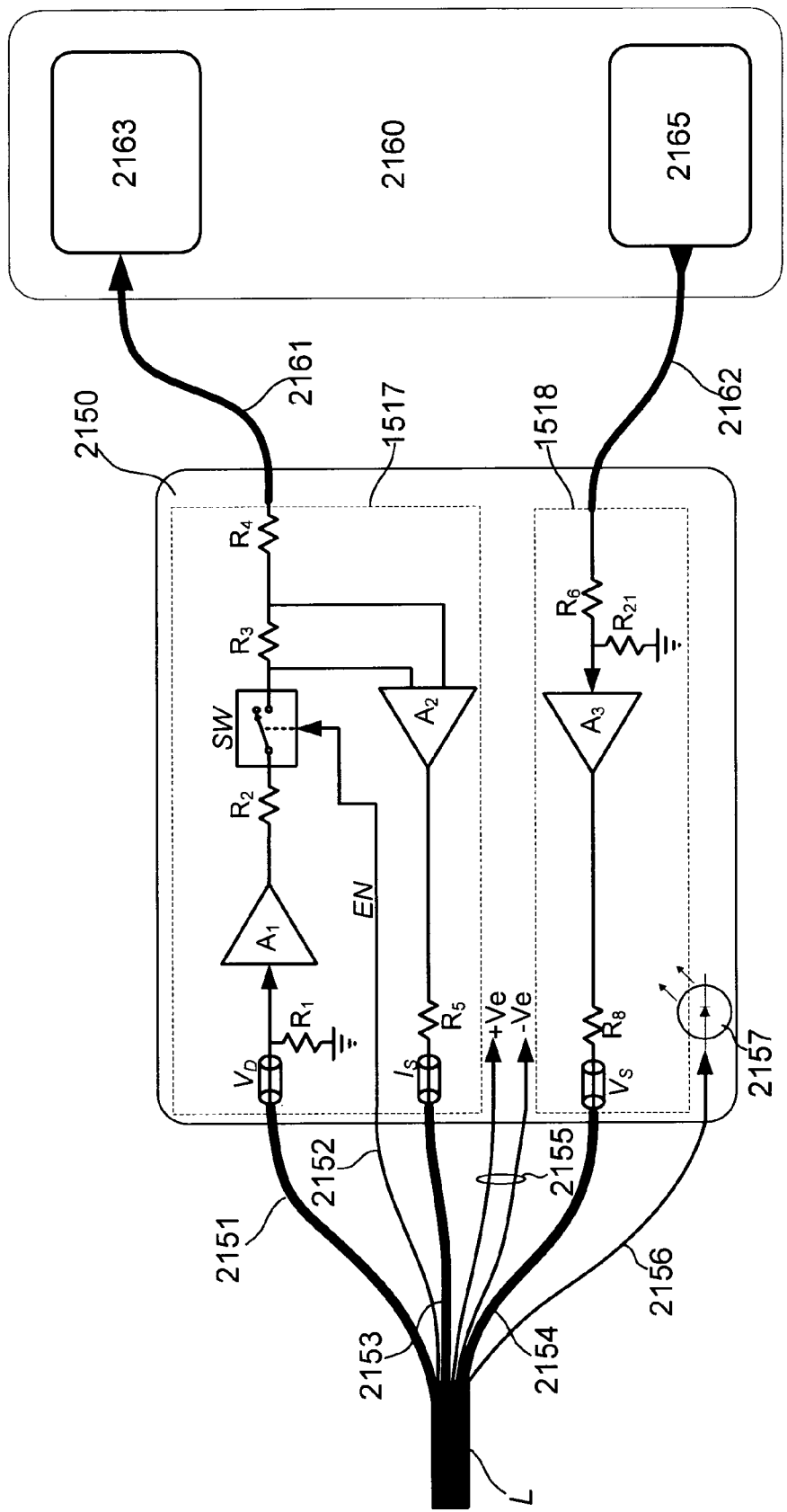
FIG. 21 is a schematic diagram of an example of an electrode system incorporating a signal generator and a sensor.

FIG. 21 is an example of an electrode system for a single one of the channels, which incorporates both a drive electrode 1513 and sense electrode 1515.

The electrode system incorporates a first substrate 2150, such as a printed circuit board (PCB), or the like, having the respective signal generator 1517 and sensor 1518 mounted thereon. The general functionality of the signal generator 1517 and sensor 1518 are represented by the components shown. In practice a greater number of components may be used in a suitable arrangement, as would be appreciated by persons skilled in the art, and the components shown are merely intended to indicate the functionality of the signal generator and the sensor 1517, 1518.

The substrate 2150 and associated components may be provided in a suitable housing to protect them during use, as will be appreciated by persons skilled in the art.

The signal generator 1517 and the sensor 1518 are also coupled via respective cables 2161, 2162 to conductive pads 2163, 2165, which may be mounted on a second substrate 2160, and which form the first and second electrodes 1513, 1515, respectively. It will be appreciated that in use, the cables 2161, 2162 may include clips or the like, to allow the conductive pads to be easily replaced after use. As will be appreciated, the conductive pads 2163, 2165 are typically formed from a silver pad, having a conductive gel, such as silver/silver chloride gel, thereon. This ensures good electrical contact with the subject S.

The conductive pads 2163, 2165 may be mounted on the substrate 2160, so as to ensure that the conductive pads 2163, 2165 are positioned a set distance apart in use, which can help ensure measurement consistency. Alternatively the conductive pads 2163, 2165 can be provided as separate disposable conductive pads, coupled to the first substrate 2150 by cables 2161, 2162. Other suitable arrangements may also be used.

In one example, the substrate 2160 is formed from a material that has a low coefficient of friction and/or is resilient, and/or has curved edges to thereby reduce the chances of injury when the electrodes are coupled to the subject.

In this example, the signal generator 1517 includes an amplifier $A_1$ having an input coupled to a cable 2151. The input is also coupled to a reference potential, such as ground, via a resistor $R_1$. An output of the amplifier $A_1$ is connected via a resistor $R_2$, to a switch SW, which is typically a CMOS (complementary metal-oxide semiconductor) switch that is used to enable the voltage source. The switch SW is controlled via enabling signals EN received from the processing system 1730 via a cable 2152.

The switch SW is in turn coupled via two resistors $R_3$, $R_4$, arranged in series, and then, via the cable 2161, to the conductive pad 2163. A second amplifier $A_2$ is provided with inputs in parallel with the first of the two series resistor $R_3$ and with an output coupled via a resistor $R_5$, to a cable 2153.

Figure 15:
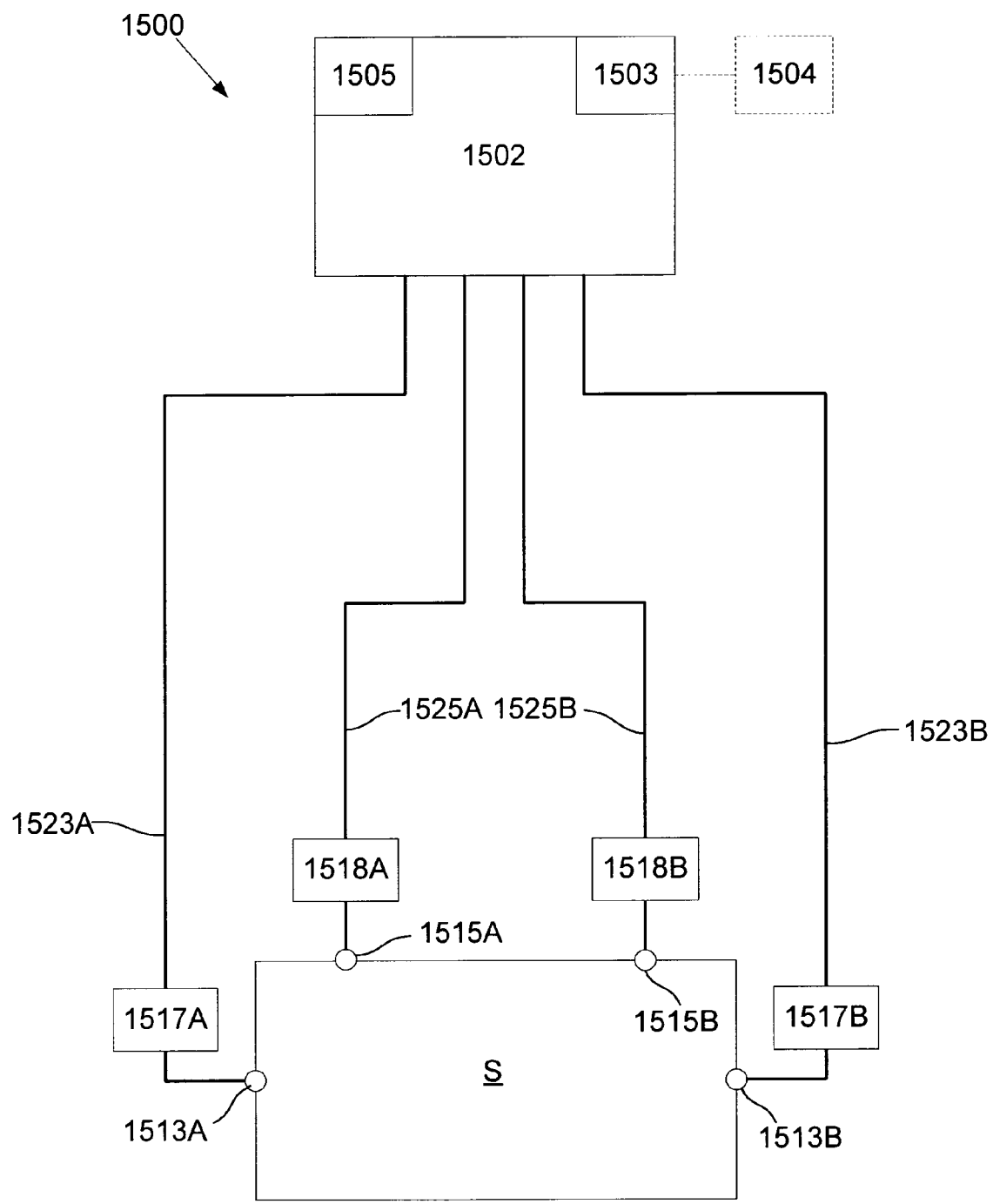
FIG. 15 is a schematic diagram of an example of an impedance measuring device.
Figure 16:
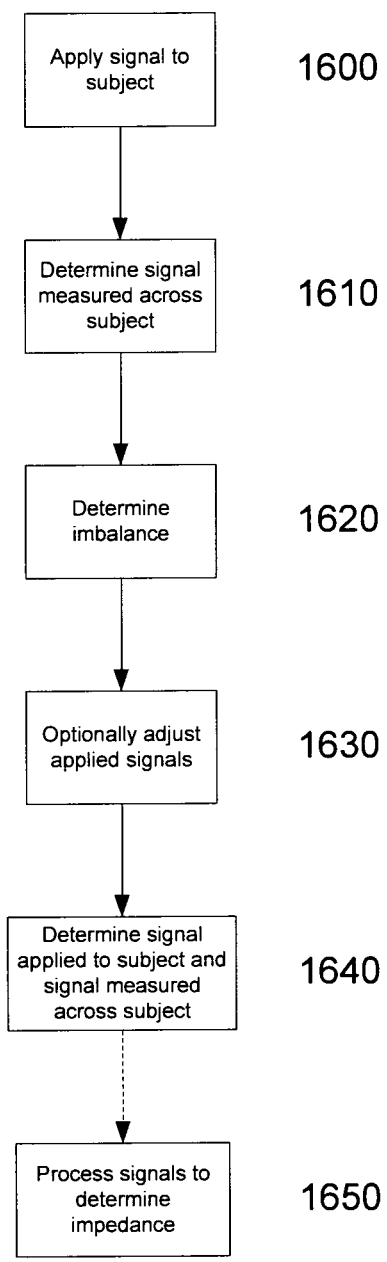
FIG. 16 is a flowchart of an example of a process for performing impedance measuring.

It will be appreciated from the above that the cables 2151, 2152, 2153 therefore form the lead 1523 of FIG. 15. A range of different resistor values may be used, but in one example, the resistors have values of $R_1=R_2=R_5=50\Omega$, and $R_3=R_4=1500\Omega$.

The sensor 1518 generally includes an amplifier $A_3$ having an input connected via a resistor $R_6$, to the cable 2162. The input is also coupled via a resistor $R_7$, to a reference potential such as a ground. An output of the amplifier $A_3$ is coupled to a cable 2154, via a resistor $R_7$.

It will be appreciated from the above that the cable 2154 therefore forms the lead 1525 of FIG. 15. A range of different resistor values may be used, but in one example, the resistors have values of $R_6=1500\Omega$, $R_7=10$ M$\Omega$ and, $R_8=50\Omega$.

Optional power cables 2155 can be provided for supplying power signals +Ve, −Ve, for powering the signal generator 1517 and the sensor 1518, although alternatively an on board power source such as a battery, may be used. Additionally, a cable 2156 may be provided to allow an LED 2157 to be provided on the substrate 2150. This can be controlled by the processing system 1730, allowing the operating status of the electrode system to be indicated.

In use, the amplifier $A_1$ operates to amplify the analogue voltage drive signal $V_D$ and apply this to the subject S via the cable 2161, so that the applied potential drives a current through the subject S. It will be appreciated that in use, this will only occur if the switch SW is in a closed position and the switch SW can therefore be placed in an open position to isolate the voltage source from the subject S.

The current of the signal being applied to the subject S is detected and amplified using the amplifier $A_2$, with the amplified current signal $I_S$ being returned to the processing system 1730, along the cable 2153 and via the ADC 1728.

Similarly, the sensor 1518 operates by having the amplifier $A_3$ amplify the potential detected at the second electrode 1515, returning the amplified analogue voltage signal $V_S$ along the cable 2154, to the ADC 1727.

The cables 2151, 2152, 2153, 2154, 2155, 2156 may be provided in a number of different configurations depending on the preferred implementation. In one example, each of the cables 2151, 2152, 2153, 2154, 2155, 2156 are provided in a single lead L, although this is not essential, and the cables could be provided in multiple leads.

As briefly mentioned above, when separate leads 1523, 1525, are used for the voltage signal $V_S$ and the current signal $I_S$, then inductive coupling between the leads 1523, 1525 can result in EMFs being induced within the leads 1523, 1525. The magnitude of the EMF is dependent on the degree of coupling between the leads 1523, 1525 and hence their physical separation, and also increases in proportion to the frequency and amplitude of the current signal $I_S$.

The EMF induced within the leads 1523, 1525 results in an effective EMF across the input of the sensor 1518. As a result, a component of the sensed voltage signal $V_S$ is due to the induced EMF, which in turn leads to inaccuracies in the determined voltage signal $V_S$ and the current signal $I_S$.

The effect of inductive coupling varies depending on the physical separation of the leads 1523, 1525. Accordingly, in one example, the effect of inductive coupling between leads can be reduced by physically separating the leads as much as possible. Thus, in one example, the cables 2151, 2152, 2153, 2154, 2155, 2156 are provided in separate physically separated leads. However, a problem with this arrangement is that the amount of inductive coupling will vary depending on the physical lead geometry, which can therefore vary between measurements. As a result, the magnitude of any inductive coupling can vary, making this difficult to account for when analysing the impedance measurements.

An alternative to using physically separate leads for each of the cables 2151, 2152, 2153, 2154, 2155, 2156 is to use a single combined lead L. The lead is formed so that the cables 2151, 2152, 2153, 2154, 2155, 2156 are held in a substantially constant relative physical configuration. In one example, the leads L are formed so as to provide a constant geometric arrangement by twisting each of the respective cables together. However, alternative fabrication techniques could be used such as making the leads from separate un-insulated shielded cables that are over moulded to maintain close contact.

As a result of the constant physical geometry, any EMF induced along the leads 1523, 1525 is substantially constant, allowing this to be accounted for during a calibration process.

Accordingly, when the measuring device 1720 is initially configured, and in particular, when the algorithms are generated for analysing the voltage and current signals $V_S$, $I_S$, to determine impedance measurements, these can include factors that take into account the induced EMF. In particular, during the configuration process, a measuring device 1720 can be used to take measurements from reference impedances, with the resulting calculations being used to determine the effect of the induced EMF, allowing this to be subtracted from future measurements.

A further source of errors can be caused by variations in the behavioural response of circuitry and other components used in the electrode system. For example, although similar components would be used on the electrode systems, manufacturing tolerances associated with the components, can mean that the components would exhibit different response to each other under the same external conditions. It will also be appreciated that the degree of variation may depend on the frequency at which a particular measurement is made.

Again however, any such variations can be accounted for during a calibration process by recording measurements from reference impedances over a number of different frequencies.

To allow the results of any such calibration to be taken into account during use, it can be useful to record the results of the calibration in such a manner as to allow these to be accessed by the measuring device 1500 in use. This can be achieved in any one of a number of manners.

Thus, for example, each lead set could have a respective identifier. A set of calibration data, indicative of deviations between the response of the lead set and an expected or idealised lead set can then be stored associated with the respective identifier. When the lead set is used with a measuring device 1500, the measuring device 1500 can determine the lead set identifier, either by way of manually input by an operator, or by automated detection of a suitable identifier provided as part of the electrode system. This then allows the measuring device 1500 to access calibration data, which could therefore be stored separately to the measuring device 1500, for example on a remote server.

As an alternative however, the calibration data could be stored on the electrode system itself, for example using a suitable memory, such as a EEPROM or the like. In this instance, an additional connection would be provided between the measuring device 1500 and the electrode system, thereby allowing the measuring device to poll the memory, and retrieve the calibration data stored thereon. This would in turn allow the calibration data to be taken into account when performing measurements.

Figure 22:
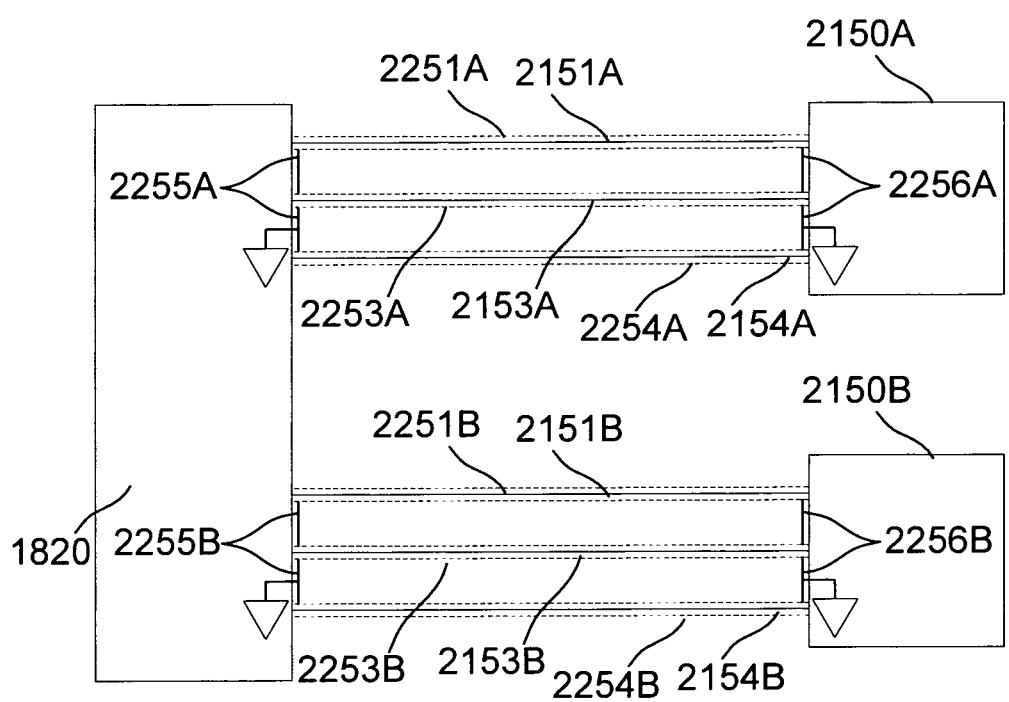
FIG. 22 is a schematic diagram of an example of lead connections between the measuring device and the electrode system of FIG. 21.

A further issue with the lead arrangement is that of capacitive coupling between the respective cables, as will now be described with respect to FIG. 22. For the purpose of this example, only cables 2151, 2153, 2154 are shown for clarity.

In this example, the measuring device 1720 is connected to the PCB's 2150A, 2150B to provide connections for each of the electrodes 1513A, 1513B, 1515A, 1515B. As also shown each of the cables 2151, 2153, 2154 have respective shielding 2251, 2253, 2254 provided thereon. The shielding is used to help prevent coupling between the respective cables 2151, 2153, 2154. It will therefore be appreciated that the cables 2151, 2153, 2154 are generally formed from a shielded wire core. In practice, the shielded cables may be 50Ω transmission lines, which minimize signal transmission distortion at high frequencies, thereby minimizing errors. In addition to this, the shields 2251, 2253, 2254 are typically interconnected at each end, to a reference potential such as a ground, via respective connections 2255, 2256.

The use of shielded and grounded cables in this fashion helps reduce the effect of capacitive coupling, helping to further reduce inaccuracies in obtained measurements.

Figure 23:
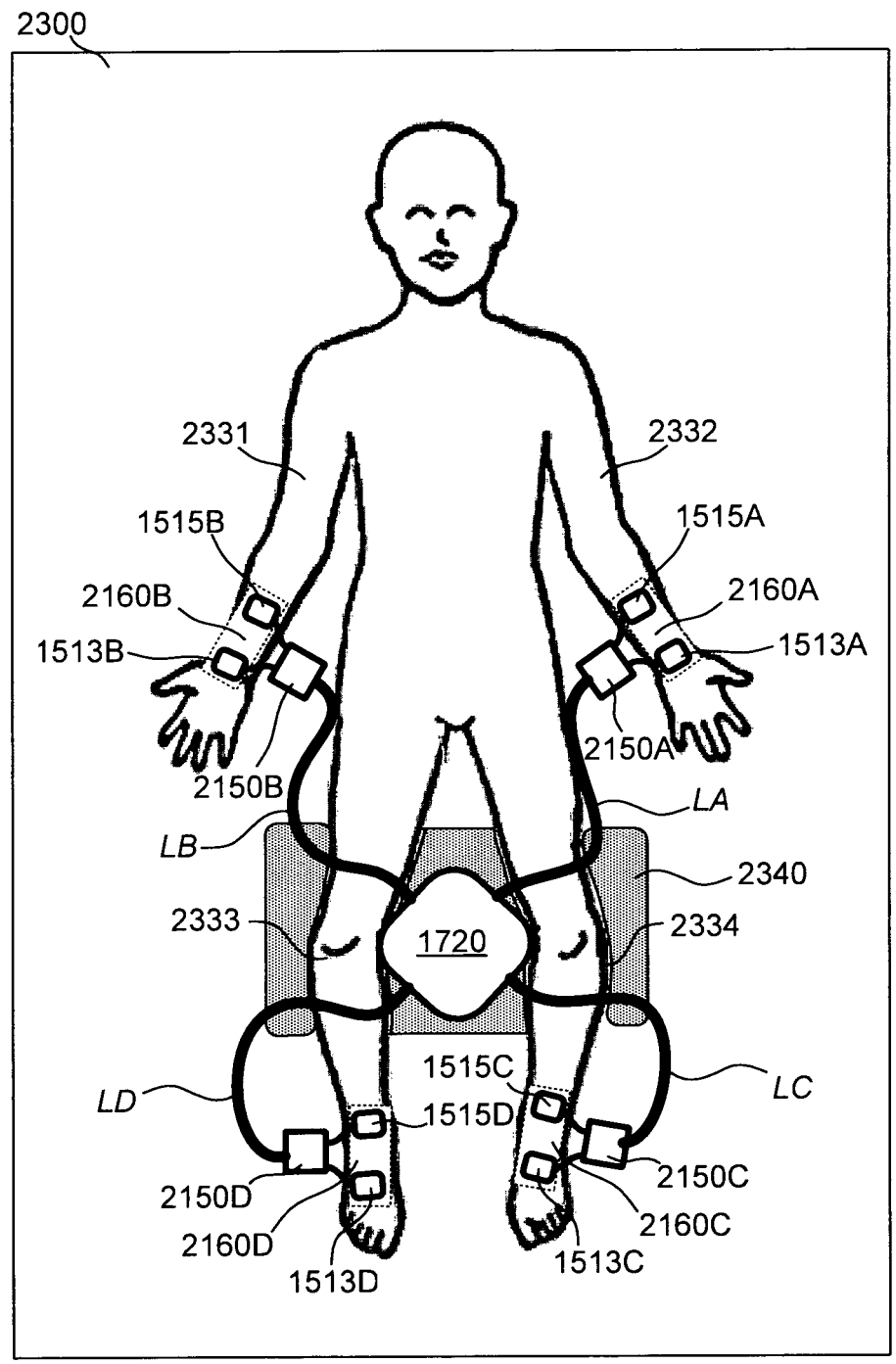
FIG. 23 is a schematic diagram of an example of a lead arrangement.

A further potential issue is that of inductive coupling between the different leads L, as well as capacitive coupling between the subject and the subject and the bed. In this regard, parasitic capacitances allow high frequency currents to bypass the intended current path through the body, resulting in measurement errors. To take this into account, in one example, the leads L for each electrode system can be physically separated as much as possible and/or provided in an arrangement that minimises lead length in use. An example of an arrangement for achieving this will now be described with respect to FIG. 23.

For the purpose of this example, the measuring system provides four measuring channels, designated by the suffixes A, B, C, D. It will be appreciated that this can be achieved by using a modified version of the measuring device 1720 of FIG. 17, in which further ADCs 1727, 1728 and DACs 1729 are provided as briefly described above.

In this example, the subject S is laying on a bed 2300, with arms 2331, 2332 positioned by the subject's side, and the legs 2333, 2334 resting on a support 2340, which incorporates the measuring device 1720. The support 940 may be any form of support, but is typically formed from molded foam, or the like, which arranges the subjects with the measuring device 1720 positioned substantially between the subject's knees. The measuring device 1720 is typically incorporated into the support both to ensure accurate location of the subject relative to the measuring device 1720, and also to protect the subject S from damage caused by rubbing or other impact with a housing of the measuring device 1720.

By providing a four channel arrangement, this allows a respective electrode system to be mounted to each of the subject's limbs. Thus, as shown, each limb 2331, 2332, 2333, 2334 has a respective substrate 2160 mounted thereon, to thereby provide a drive and sense electrode 1513, 1515 on each wrist and ankle. The electrodes 1513, 1515, are coupled to respective signal generators and sensors mounted on the substrates 2150, which are in turn coupled to the measuring device 1720 via respective leads LA, LB, LC, LD.

The leads are arranged so that each lead LA, LB, LC, LD extends away from the measuring device 1720 in different directions, thereby maximizing the physical separation of the leads and hence helping to reduce any inductive coupling therebetween.

Additionally, the leads LA, LB, LC, LD are preferably adapted to extend perpendicularly from both the measuring device 1720 and the subject S, to thereby further reduce the effects of capacitive coupling.

Furthermore, by having the measuring device 1720 positioned near the subject's knee, this places the measuring device 1720 approximately equi-distant between the subject's knees and ankles.

Thus, by arranging the measuring device 1720 towards the lower end of the bed 900, this reduces the length of leads LA, LB, LC, LD needed to place the electrodes on the wrist and ankle of the subject S, whilst maintaining substantially equal lead lengths which helps further reduce both inductive and capacitive coupling effects. In this regard, the EMF originating from any inductive coupling effect is proportional to the relevant lead length. Similarly, capacitive coupling between the leads (ground) and the subject S, which can create current shunt paths, is also minimized.

It will be appreciated that in this arrangement, by having four first electrodes and four second electrodes positioned on the limbs, this allows a range of different limb and/or whole body impedance measurements to be performed as described above.

During the measurement procedure, in general only two of the channels will be used at any one time. To achieve this, the other channels will be disabled through use of the respective switch SW, which forms part of the electrode system.

Figure 24:
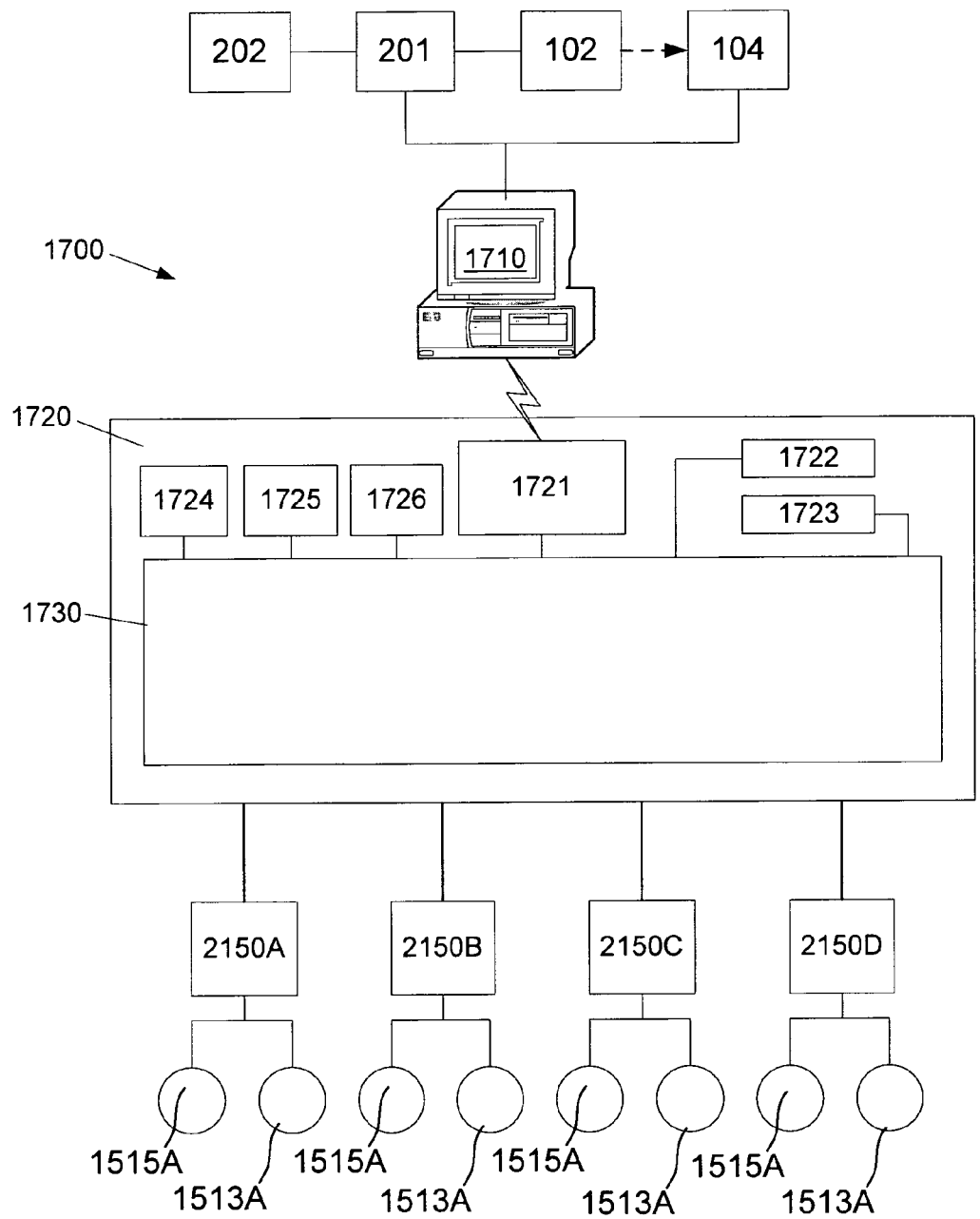
FIG. 24 is a schematic diagram of an example of the apparatus of FIG. 2 incorporating the impedance measuring device of FIG. 17.

It will be appreciated that the above described impedance measurement apparatus and method variations described above with respect to FIGS. 15 to 23 could be utilised in conjunction with the apparatus and methods of FIGS. 1 to 14 to provide further enhanced measurements. In this arrangement, as shown in FIG. 24, the computer system 1710 is used to control the measuring device 1720 of FIG. 15, instead of the measuring device 203 of FIG. 2, as well as the DEXA measuring system including the signal generator 201 and detector 104. Thus, the computer system 1710 can replace the processing system 200, with the measuring device 1720 being placed on the support surface 101 using an arrangement similar to that shown in FIG. 23, so that the measuring device 1720 replaces the measuring device 203. In this instance, when impedance measurements are performed at step 330, this can be achieved using the process of FIG. 16.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that features from different examples above may be used interchangeably where appropriate. Furthermore, whilst the above examples have focussed on a subject such as a human, it will be appreciated that the measuring device and techniques described above can be used with any animal, including but not limited to, primates, livestock, performance animals, such race horses, or the like.

The above described processes can be used for diagnosing the presence, absence or degree of a range of conditions and illnesses, including, but not limited to oedema, lymphodema, body composition, visceral fat detection, or the like.

It will also be appreciated that the term impedance measurement covers admittance and other related measurements.

The claims defining the invention are as follows:

1. A method for use in determining a presence, absence or degree of lymphoedema using a processing system, comprising the steps of:
    a) performing at least one radiation attenuation measurement; wherein the processing system uses a signal generator to control a radiation source for performing the radiation attenuation measurement;
    b) determining limb volumes for a subject using a determined radiation attenuation; wherein a detector measures an intensity of transmitted radiation and returns the intensity of transmitted radiation to the processing system for determination of limb volumes for the subject;
    c) performing at least one impedance measurement; wherein the processing system uses a controller to control a signal generator and sensor for performing the at least one impedance measurement;
    d) determining fluid levels in the subject using a determined impedance measurement wherein the controller returns the at least one impedance measurement to the processing system, or wherein the controller returns at least one derived impedance parameter value to the processing system for determining fluid levels in the subject; and,
    e) using the processing system to determine an indication of the presence, absence or degree of lymphoedema by:
        i) using the limb volumes to detect the presence or absence of lymphoedema;
        ii) using the fluid levels to detect the presence, absence or degree of lymphoedema; and,
        iii) detecting that lymphoedema is at an early stage if lymphoedema is detected using the fluid levels but not using the limb volumes.

2. The method according to claim 1, further comprising: performing the radiation attenuation measurement by:
    a) exposing the subject to radiation from the radiation source; and,
    b) determining the attenuation of radiation transmitted through the subject.

3. The method according to claim 2, further comprising:
    a) causing the radiation source to scan along a length of the subject; and,
    b) receiving an indication of radiation attenuation from a detector.

4. The method according to claim 1, further comprising: performing the impedance measurement by:
    a) applying one or more electrical signals to the subject using a first set of electrodes;
    b) determining an indication of electrical signals measured across a second set of electrodes applied to the subject; and,
    c) determining from the indication and the one or more applied signals, the fluid levels.

5. The method according to claim 1, further comprising:
    a) determining at least one measurement procedure to be performed; and,
    b) performing the radiation attenuation and impedance measurements in accordance with the determined measurement procedure.

6. The method according to claim 5, further comprising:
    a) selecting instructions corresponding to the measurement procedure; and
    b) transferring the instructions to a second processing system, the second processing system being for:
        i) generating, using the instructions, control signals, the control signals being used to apply one or more signals to the subject;
        ii) receiving an indication of the one or more signals applied to the subject;

iii) receiving an indication of one or more signals measured across the subject; and
iv) performing, using the instructions, at least preliminary processing of the indications to thereby allow impedance values to be determined.

7. The method according to claim 5, further comprising:
a) determining at least one electrode arrangement associated with the determined measurement procedure;
b) displaying a representation indicative of the electrode arrangement; and,
c) performing the impedance measurement once the electrodes have been arranged in accordance with the displayed representation.

8. The method according to claim 1, wherein fluid levels are indicative of at least one of:
a) an index based on the ratio of extra- to intra-cellular fluid;
b) an index based on an impedance parameter value;
c) an intracellular fluid volume; and,
d) an extracellular fluid volume.

9. The method according to claim 1, further comprising:
a) comparing the fluid levels to at least one of:
i) a predetermined reference;
ii) fluid levels determined for at least one other body segment;
iii) previously determined fluid levels; and,
b) determining an indication of the presence, absence or degree of oedema using the results of the comparison.

10. The method according to claim 9, wherein the reference comprises at least one of:
a) a predetermined threshold;
b) a tolerance determined from a normal population;
c) a predetermined range; and,
d) fluid levels previously determined for the subject.

11. The method according to claim 1, further comprising:
a) determining a first measured impedance indicative of a measured impedance for a first half of a first limb;
b) determining a second measured impedance indicative of a measured impedance for a second half of the first limb;
c) determining a third measured impedance indicative of a measured impedance for the first limb;
d) determining a derived impedance indicative of an impedance for the first half of the first limb using the second and third measured impedances; and,
e) comparing the first measured impedance and the derived impedance.

12. The method according to claim 11, further comprising:
a) determining if any electrodes are incorrectly positioned in accordance with the results of the comparison of the first measured impedance and the derived impedance; and,
b) generating an indication of any incorrectly positioned electrodes.

13. The method according to claim 1, further comprising:
a) determining a measured impedance value for at least one body segment;
b) for each body segment, and using the measured impedance values, determining at least one impedance parameter value; and,
c) using each determined impedance value to determine the fluid levels.

14. The method according to claim 13, further comprising:
a) determining at least one impedance parameter value using each determined impedance value; and, b) determining the fluid levels using the at least one impedance parameter value.

15. The method according to claim 13, further comprising:
a) determining a plurality of measured impedance values for each body segment, each measured impedance value being measured at a corresponding measurement frequency; and,
b) determining impedance parameter values based on the plurality of measured impedance values.

16. The method according to claim 13, wherein the parameter values include $R_0$ and $R_\infty$, wherein:
a) $R_0$ is the resistance at zero frequency; and,
b) $R_\infty$ is the resistance at infinite frequency.

17. The method according to claim 16, further comprising:
a) monitoring changes over time for at least one of:
i) $R_0$;
ii) $R_\infty$; and
iii) a difference between $R_0$ and $R_\infty$; and
b) a vector indication of an impedance measurement.

18. The method according to claim 16, further comprising:
a) determining values for parameters $R_0$ and $R_\infty$ from the measured impedance values; and,
b) determining the indicator by calculating the index (I) using the equation:

$$I = \frac{R_\infty}{R_0 - R_\infty}.$$

19. The method according to claim 16, further comprising: determining the parameter values using the equation:

$$Z = R_\infty + \frac{R_0 - R_\infty}{1 + (j\omega\tau)^{(1-\alpha)}}$$

where:
Z is the measured impedance at angular frequency ω,
τ is a time constant, and
α has a value between 0 and 1.

20. The method according to claim 1, further comprising: determining the fluid levels as an extracellular fluid volume using the equation:

$$ECV_{Segment} = C_{Segment}\rho_{Segment}\left(\frac{L^2_{Segment}}{R_{Segment}}\right)$$

Where ECV=Extracellular fluid volume
$C_{Segment}$=Geometry constant which is 1 for an arm or leg and 4 for the thoracic cavity
$L_{Segment}$=Length of the segment in cm
$R_{Segment}$=Resistance of the segment in Ohm
$\rho_{Segment}$=Resistivity coefficient which is nominally 47 Ohm/cm.

21. The method according to claim 20, further comprising: determining the extracellular fluid volume for the entire body using the equation:

$$ECV_{Total} = 2(ECV_{arm} + ECV_{leg}) + ECV_{trunk}.$$

22. The method according to claim 1, further comprising: performing the at least one impedance measurement by:

a) applying a first signal to the subject;
b) determining an indication of a second signal measured across the subject;
c) determining an imbalance using the indication of the second signal;
d) determining a modified first signal in accordance with the imbalance; and,
e) applying the modified first signal to the subject to thereby allow at least one impedance measurement to be performed.

23. The method according to claim 22, further comprising: determining the modified first signal so as to minimize the imbalance.

24. The method according to claim 1, wherein the method is performed using an apparatus comprising:
a) at least two electrode systems, each electrode system comprising:
  i) a signal generator for applying a first signal to be applied to the subject;
  ii) a sensor for sensing a second signal across the subject;
  iii) a first electrode for coupling the signal generator to the subject; and,
  iv) a second electrode for coupling the sensor to the subject; and,
b) a measuring device for controlling the electrode systems to allow impedance measurements to be performed; and,
c) at least two leads for connecting the measuring device to the electrode systems, and wherein the leads are arranged to at least one of:
  i) extend from the measuring device in different directions to thereby reduce inductive coupling therebetween; and,
  ii) minimize the lead length.

25. Apparatus for use in determining a presence, absence or degree of lymphoedema, comprising a processing system for:
a) performing at least one radiation attenuation measurement; wherein the processing system is coupled to a signal generator to control a radiation source for performing the radiation attenuation measurement;
b) determining limb volumes for a subject using a determined radiation attenuation; wherein the processing system is coupled to a detector and wherein the detector determines a transmitted radiation measurement and returns the transmitted radiation measurement to the processing system for determination of limb volumes for the subject;
c) performing at least one impedance measurement wherein the processing system is coupled to a controller to control a signal generator and sensor for performing the at least one impedance measurement;
d) determining fluid levels in the subject using a determined impedance measurement; wherein the controller returns the at least one impedance measurement to the processing system, or wherein the controller returns at least one derived impedance parameter value to the processing system for determining fluid levels in the subject; and
e) determining an indication of the presence, absence or degree of lymphoedema by the processing system by:
  i) using the limb volumes to detect the presence or absence of lymphoedema;
  ii) using the fluid levels to detect the presence, absence or degree of lymphoedema; and,
f) detecting that lymphoedema is at an early stage if lymphoedema is detected by the processing system using the fluid levels but not using the limb volumes.

26. The apparatus according to claim 25, further comprising: a drive system that moves the radiation source and detector relative to the subject, to thereby expose the subject to the radiation.

27. The apparatus according to claim 25, further comprising:
a) a support surface for supporting the subject; and,
b) one or more leads at least partially embedded within the support surface, the leads being for use in performing the impedance measurement procedure.

28. The apparatus according to claim 25, further comprising:
a) an arm for supporting a detector; and,
b) one or more leads at least partially embedded within the arm, the leads being for performing the impedance measurement procedure.

29. The apparatus according to claim 27, wherein the leads are radiolucent.

30. The apparatus according to claim 25, further comprising: electrodes provided as part of at least one of:
a) a foot plate;
b) a hand plate;
c) a band electrode; and,
d) a cuff.

31. The apparatus according to claim 25, wherein:
the signal generator is configured to apply one or more electrical signals to the subject using a first set of electrodes; and further comprising:
a sensor for measuring electrical signals measured across a second set of electrodes; and wherein,
a) the controller is configured for:
  i) controlling the signal generator; and,
  ii) determining the indication of the measured electrical signals.

32. The apparatus according to claim 31, wherein the controller performs the steps of:
a) receiving instructions from the processing system;
b) generating, using the instructions, control signals, the control signals being used to apply one or more signals to the subject;
c) receiving an indication of the one or more signals applied to the subject;
d) receiving an indication of one or more signals measured across the subject; and
e) performing, using the instructions, at least preliminary processing of the indications to thereby allow impedance values to be determined.

33. The apparatus according to claim 25, wherein the processing system performs the impedance measurements by:
a) applying a first signal to the subject;
b) determining an indication of a second signal measured across the subject;
c) determining an imbalance using the indication of the second signal;
d) determining a modified first signal in accordance with the imbalance; and
e) applying the modified first signal to the subject to thereby allow at least one impedance measurement to be performed.

34. The apparatus according to claim 25, further comprising: leads for connecting a measuring device to an electrode system, the electrode system comprising a signal generator and a sensor, and the leads comprising:

a) at least two connections for connecting the measuring device and the signal generator, and the measuring device and the sensor; and,
b) a shield for each of the at least two connections, the shields being electrically connected, and connected to a reference potential in each of the measuring device and the electrode system.

35. The apparatus according to claim 25, further comprising:
a) at least two electrode systems, each electrode system comprising:
   i) a signal generator for applying a first signal to be applied to the subject;
   ii) a sensor for sensing a second signal across the subject;
   iii) a first electrode for coupling the signal generator to the subject; and,
   iv) a second electrode for coupling the sensor to the subject; and,
b) a measuring device for controlling the electrode systems to allow impedance measurements to be performed; and,
c) at least two leads for connecting the measuring device to the electrode systems, the leads being arranged to at least one of:
   i) extend from the measuring device in different directions to thereby reduce inductive coupling therebetween; and,
   ii) minimize the lead length.

* * * * *